(12) United States Patent
Yasugi et al.

(10) Patent No.: US 9,243,077 B2
(45) Date of Patent: Jan. 26, 2016

(54) DERIVATIVE OF HYALURONIC ACID MODIFIED WITH AMINO-CARBOXYLIC ACID

(75) Inventors: Tomoko Yasugi, Shizuoka (JP); Yoshihiro Tampo, Shizuoka (JP); Kenji Yasugi, Shizuoka (JP); Tai Hirakura, Shizuoka (JP); Tsuyoshi Shimoboji, Shizuoka (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 9 days.

(21) Appl. No.: 14/002,919

(22) PCT Filed: Mar. 2, 2012

(86) PCT No.: PCT/JP2012/055421
§ 371 (c)(1),
(2), (4) Date: Sep. 3, 2013

(87) PCT Pub. No.: WO2012/118189
PCT Pub. Date: Sep. 7, 2012

(65) Prior Publication Data
US 2013/0338352 A1    Dec. 19, 2013

(30) Foreign Application Priority Data
Mar. 3, 2011    (JP) .................... 2011-046749

(51) Int. Cl.
*C08B 37/08* (2006.01)
*A61K 31/728* (2006.01)
*A61K 47/48* (2006.01)

(52) U.S. Cl.
CPC .......... *C08B 37/0072* (2013.01); *A61K 31/728* (2013.01); *A61K 47/4823* (2013.01)

(58) Field of Classification Search
None
See application file for complete search history.

(56) References Cited

U.S. PATENT DOCUMENTS

| 4,937,270 A * | 6/1990 | Hamilton et al. ............ 514/777 |
| 2007/0031503 A1 | 2/2007 | Hirakura et al. |
| 2007/0134334 A1 | 6/2007 | Hahn et al. |
| 2009/0082266 A1 | 3/2009 | Nakamura et al. |
| 2009/0148534 A1 | 6/2009 | Yasugi et al. |
| 2011/0212901 A1 | 9/2011 | Akiyoshi et al. |

FOREIGN PATENT DOCUMENTS

| EP | 1757314 A1 | 2/2007 |
| JP | 200181103 U | 5/1989 |
| JP | H02-273176 A | 11/1990 |
| JP | H0585942 A | 4/1993 |
| JP | 2002519481 A | 7/2002 |
| JP | 2003518167 A | 6/2003 |
| WO | 9206714 A1 | 4/1992 |
| WO | 9220349 A1 | 11/1992 |
| WO | 9929839 A1 | 6/1999 |
| WO | 0001733 A1 | 1/2000 |
| WO | 0016818 A1 | 3/2000 |
| WO | 0105434 A2 | 1/2001 |
| WO | 0146265 A1 | 6/2001 |
| WO | 0160412 A2 | 8/2001 |
| WO | 2005023906 A1 | 3/2005 |
| WO | 2005054301 A1 | 6/2005 |
| WO | 2005054302 A1 | 6/2005 |
| WO | 2006028110 A1 | 3/2006 |
| WO | 2006095775 A1 | 9/2006 |
| WO | 2010053140 A1 | 5/2010 |
| WO | 2010145821 A1 | 12/2010 |
| WO | 2011148116 A2 | 12/2011 |

OTHER PUBLICATIONS

Bergman, K. et al "Hyaluronic acid derivatives prepared in aqueous media . . . " Biomacromolecules (2007) vol. 8, pp. 2190-2195.*
Oh, E. et al "Target specific and long-acting delivery of protein . . . " J. Controlled Release (2010) vol. 141, pp. 2-12.*
Lee, J. et al "Hyaluronic acid-paclitaxel conjugate micelles . . . " Bioconj. Chem. (2008) vol. 19, pp. 1319-1325.*
Kurisawa, M. et al "Injectable biodegradable hydrogels . . . " Chem. Commun. (2005) pp. 4312-4314.*
Young, J. et al "Preparation of cross-linked hyaluronic acid film . . . " (2004) J. Biomater. Sci. Polym. Ed. (2004) vol. 15, No. 6, pp. 767-780. Abstract Only.*
Paul Bulpitt et al, "New Strategy for chemical modification of hyaluronic acid: Preparation of functionalized derivatives and their use in the formation of novel biocompatible hydrogels" Journal Biomedical Materials Research. John Wiley and Sons, Inc. 47:2:152-169 (Mar. 1999).
European Search Report, dated Oct. 16, 2014, in corresponding European application No. EP12752403.
Bergman, Kristoffer et al., "Hyaluronic Acid Derviatives Prepared in Aqueous Media by Triazine-activated Amidation", Biomacromolecules, vol. 8, No. 7, pp. 2190-2195, 2007.
Chen, Rongjun et al., "The Role of Hydrophobic Amino Acid Grafts in the Enhancement of Membrane-Disruptive Activity of Ph-Responsive Pseudo-Peptides", Biomaterials, vol. 30, pp. 1954-1961, 2009.
Godbey, W.T. et al., "Poly(Ethylenimine) and Its Role in Gene Delivery", Journal of Controlled Release, vol. 60, pp. 149-160, 1999.
Haensler, Jean et al., "Polyamidoamine Cascade Polymers Mediate Efficient Transfection of Cells in Culture", Bioconjugate Chemicals, vol. 4, pp. 372-379, 1993.
Ishida, Tatsuhiro et al., "Accelerated Clearance of a Second Injection of Pegylated Lipsosomes in Mice", International Journal of Pharmceutics, vol. 255, pp. 167-174, 2003.

(Continued)

*Primary Examiner* — Leigh C Maier
(74) *Attorney, Agent, or Firm* — Browdy and Neimark, PLLC

(57) ABSTRACT

The present invention provides a hyaluronic acid derivative comprising disaccharide units of Formula (I), and a hyaluronic acid derivative/drug conjugate wherein one or more drugs are conjugated to the hyaluronic acid derivative.

11 Claims, 37 Drawing Sheets

(56) References Cited

OTHER PUBLICATIONS

Jiang, Ge et al., "Hyaluronic Acid-Polyethyleneimine Conjugate for Target Specific Intracellular Delivery of siRNA", Biopolymers, vol. 89, No. 7, pp. 635-642, 2008.

Lee, Hyukjin et al., "Target-Specific Intracellular Delivery of siRNA Using Degradable Hyaluronic Acid Nanogels", Journal of Controlled Release, vol. 119, pp. 245-252, 2007.

Maclaughlin, Fiona C., et al., "Chitosan and Depolymerized Chitosan Oligomers as Condensing Carriers for In Vivo Plasmid Delivery", Journal of Controlled Release, vol. 56, pp. 259-272, 1998.

Midoux, Patrick et al., "Efficient Gene Transfer by Histidylated Polylysine/PDNA Complexes", Bioconjugate Chemicals, vol. 10, pp. 406-411, 1999.

Murthy, Niren et al., "The Design and Synthesis of Polymers for Eukaryotic Membrane Disruption", Journal of Controlled Release, vol. 61, pp. 137-143, 1999.

Rozema, David B. et al., "Endosomolysis by Masking of a Membrane-Active Agent (EMMBA) for Cytoplasmic Release of Macromolecules", Bioconjugate Chemicals, vol. 14, pp. 51-57, 2003.

Sakaguchi, Naoki et al., "Preparation of PH-Sensitive Poly(Glycidol) Derivatives With Varying Hydrophobicities: Their Ability to Sensitize Stable Liposomes to PH", Bioconjugate Chemicals, vol. 19, pp. 1040-1048, 2008.

Schante, Carole et al., "Synthesis of N-Alanyl-Hyaluronamide With High Degree of Substitution for Enhanced Resistance to Hyaluronidase-Mediated Digestion", Carbohydrate Polymers, vol. 86, pp. 747-752, 2011.

Schante, Carole E. et al., "Improvement of Hyaluronic Acid Enzymatic Stability by the Grafting of Amino-Acids", Carbohydrate Polymers, vol. 87, pp. 2211-2216, 2012.

Thomas, James L. et al., "Polyelectrolyte-Sensitized Phospholipid Vesicles", Accounts of Chemical Research, vol. 25, pp. 336-342, 1992.

Vives, Eric et al., "A Truncated HIV-1 TAT Protein Basic Domain Rapidly Translocates Through the Plasma Membrane and Accumulates in the Cell Nucleus", The Journal of Biological Chemistry, vol. 272, No. 25, pp. 16010-16017, 1997.

Wu, George Y. et al., "Receptor-Mediated In Vitro Gene Transformation by a Soluble DNA Carrier System", The Journal of Biological Chemistry, vol. 262, No. 10, pp. 4429-4432, 1987.

Zelphati, Olivier et al., "Intracellular Delivery of Proteins With a New Lipid-Mediated Delivery System", The Journal of Biological Chemistry, vol. 276, No. 37, pp. 35103-35110, 2001.

Ishida, Tatsuhiro et al., "Accelerated Clearance of Pegylated Liposomes in Rats After Repaeated Injections", Journal of Controlled Release, vol. 88, pp. 35-42, 2003.

* cited by examiner

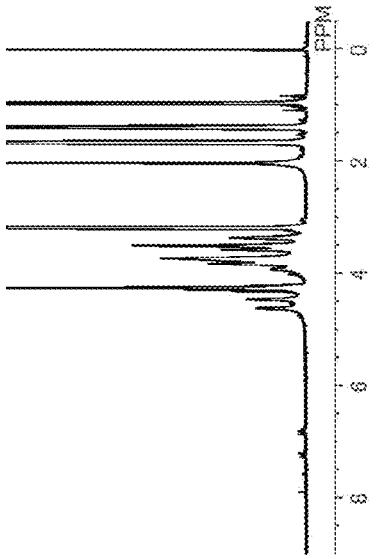
FIG. 2  Example 1-3
         HA-FL/TBA
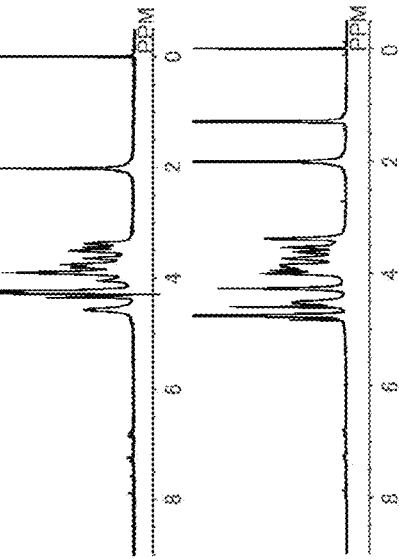
FIG. 3-2  Example 1-4-2
          HA-Ser/FL (upper), HA-Ser-OEt/FL (lower)
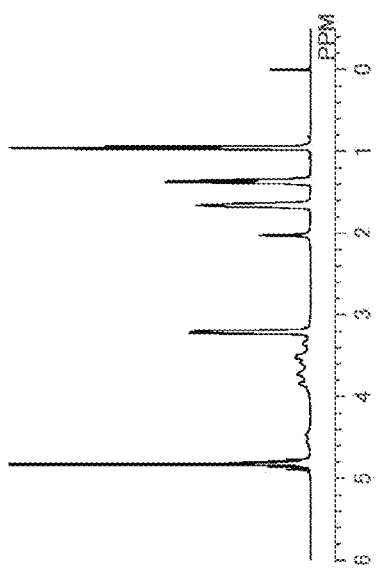
FIG. 1  Example 1-2
        HA-TBA
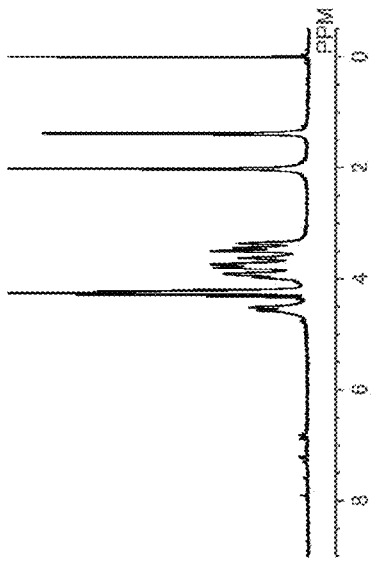
FIG. 3-1  Example 1-4-1
          HA-Ala/FL

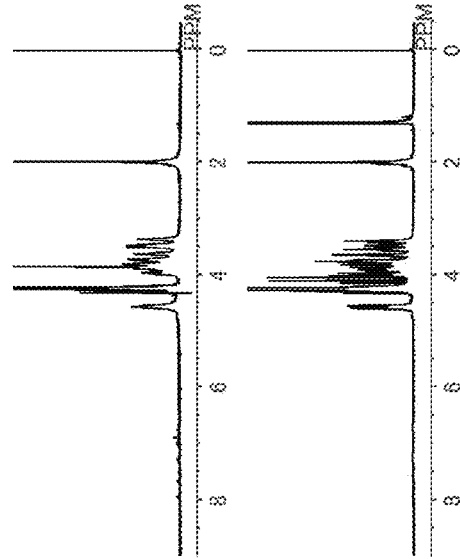
FIG. 3-3  Example 1-4-3  HA-Glu/Fl
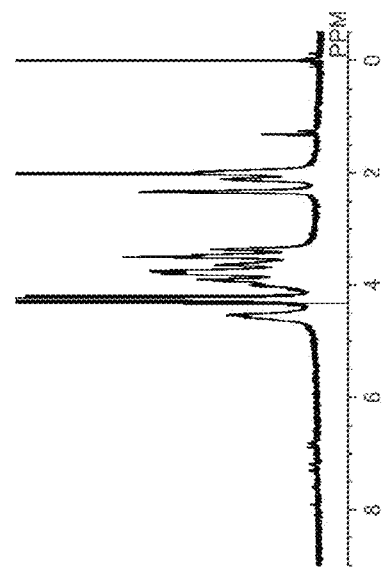
FIG. 3-4  Example 1-4-4  HA-Gly/Fl (upper), HA-Gly-OEt/Fl (lower)
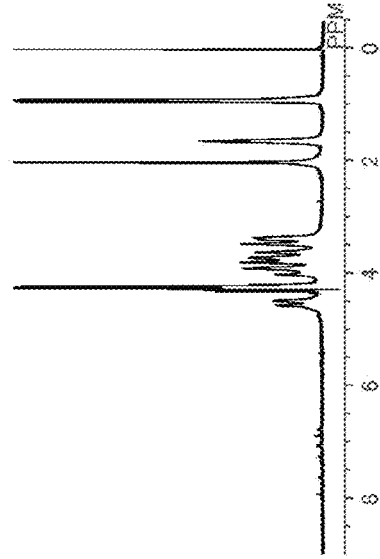
FIG. 3-5  Example 1-4-5  HA-Val/Fl
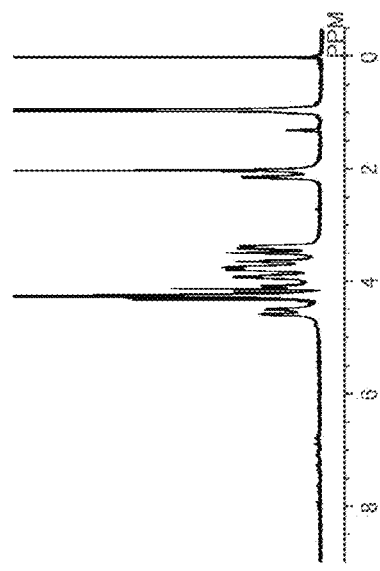
FIG. 3-6  Example 1-4-6  HA-Leu/Fl

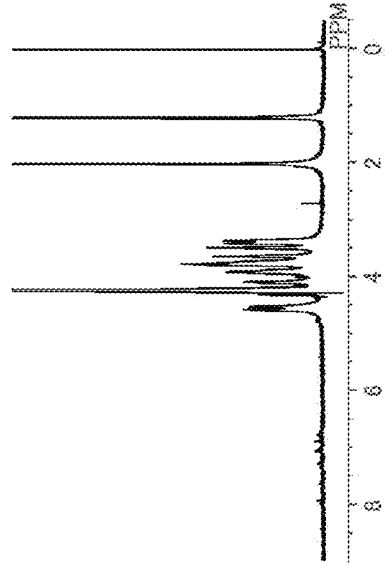
FIG. 3-8   Example 1-4-8   HA-Thr/FL
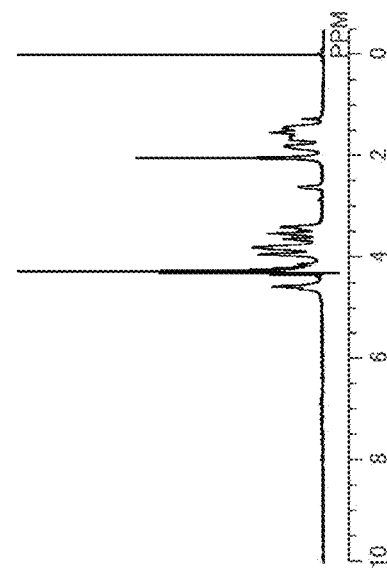
FIG. 3-10   Example 1-4-10   HA-cACHCA/FL
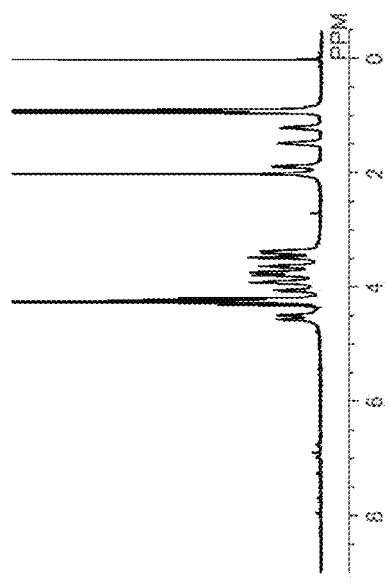
FIG. 3-7   Example 1-4-7   HA-Ile/FL
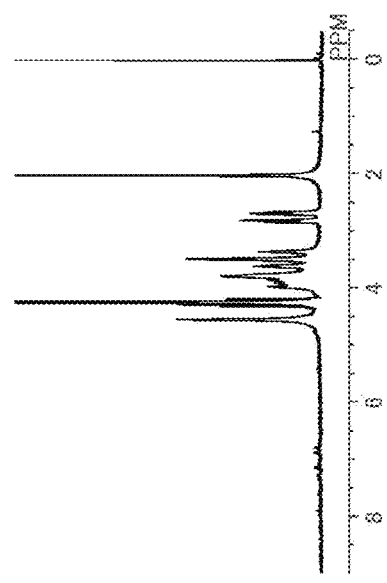
FIG. 3-9   Example 1-4-9   HA-Asp/FL

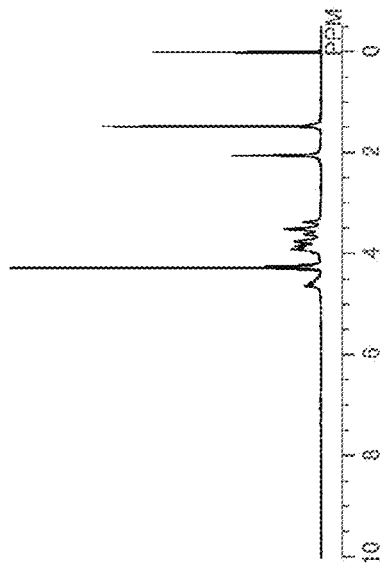
FIG. 3-11  Example 1-4-11  HA-IACHCA-OEt/FL
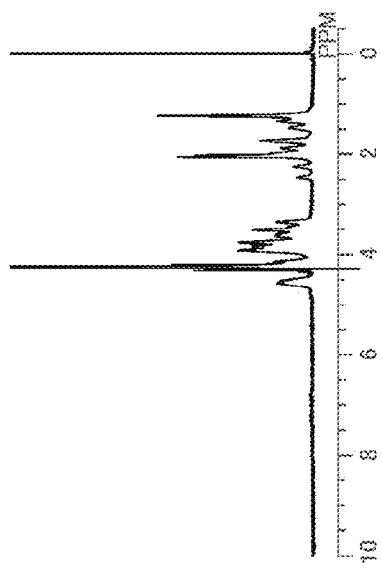
FIG. 3-12  Example 1-4-12  HA-Aib/FL
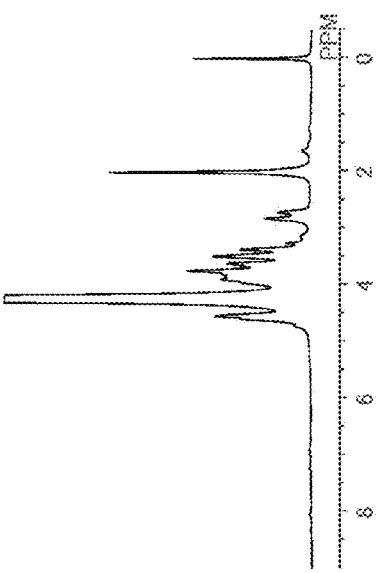
FIG. 3-13  Example 1-4-13  HA-ACBuCA-OEt/FL
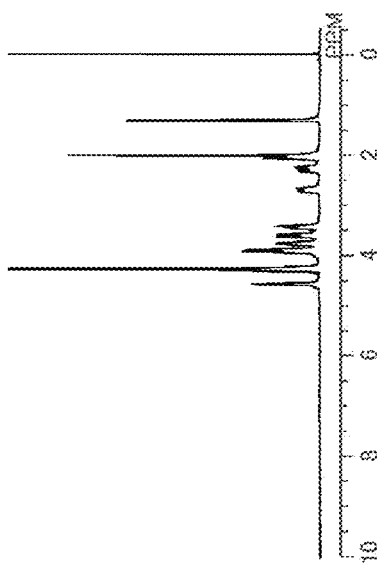
FIG. 3-14  Example 1-4-14  HA-Asn/Rh

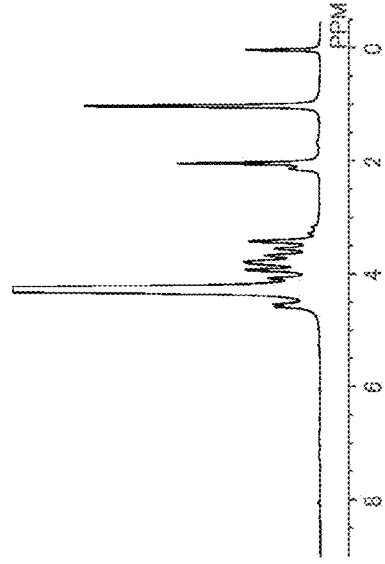
FIG. 3-15  Example 1-4-15
HA-Ala-NH₂/Rh
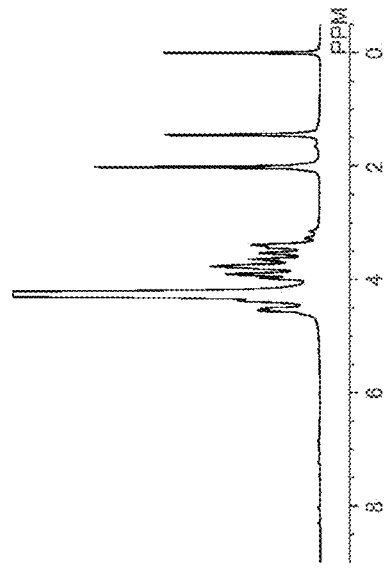
FIG. 3-16  Example 1-4-16
HA-Val-NH₂/Rh
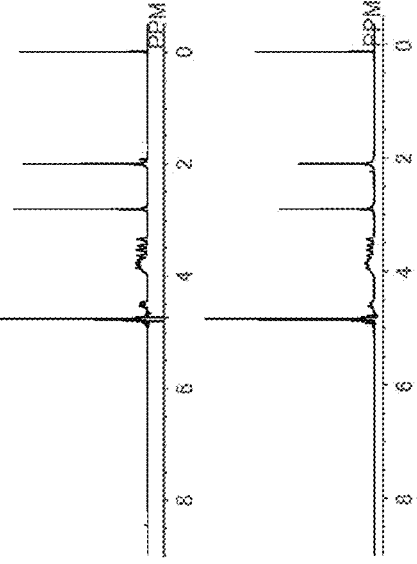
FIG. 3-17  Example 1-4-17
HA-Asn-NH₂/Rh
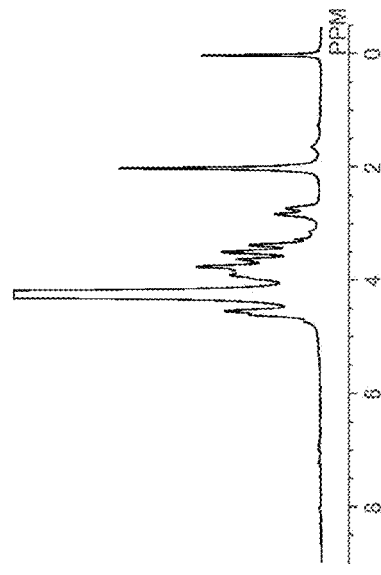
FIG. 3-18  Example 1-4-18
HA-Me (upper), HA-Me/Fl (lower)

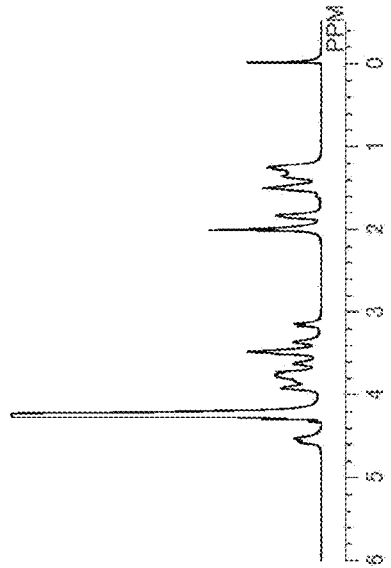
FIG. 4-1  Example 1-5-1  HA-AMCHCA
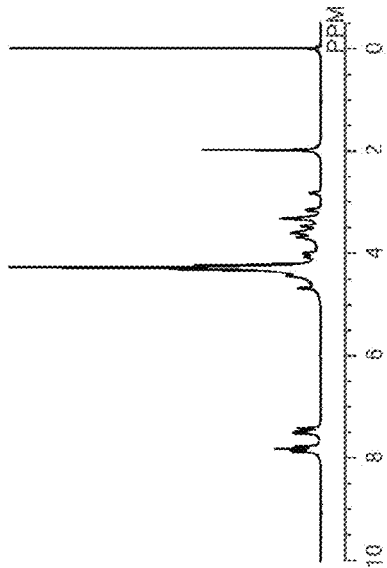
FIG. 4-3  Example 1-5-3  HA-NaI
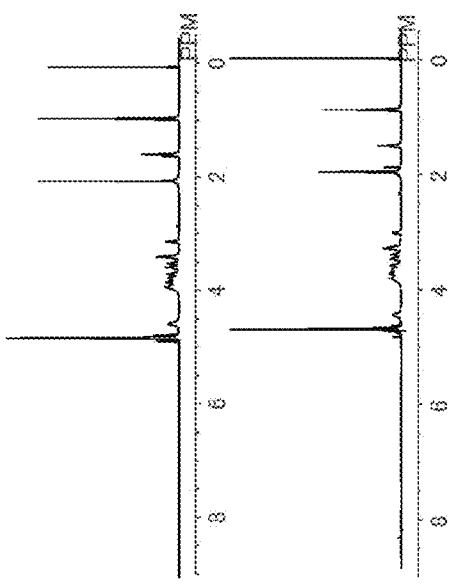
FIG. 3-19  Example 1-4-19  HA-Pr (upper), HA-Pr/FL (lower)
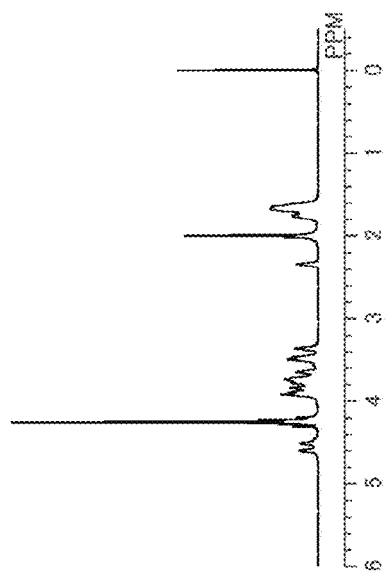
FIG. 4-2  Example 1-5-2  HA-pcACHCA

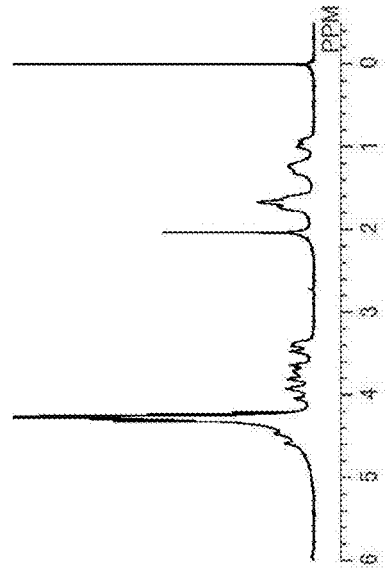
FIG. 4-5 Example 1-5-5 HA-Cha
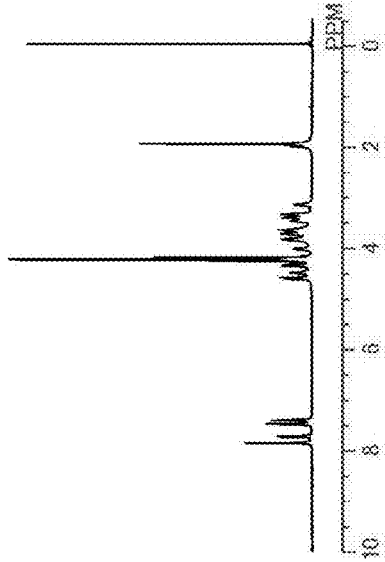
FIG. 4-7 Example 1-5-7 HA-3AMBA
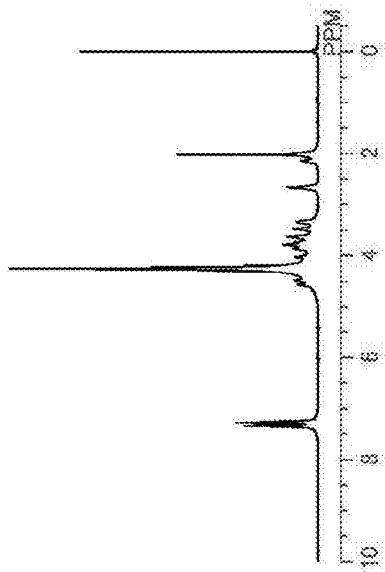
FIG. 4-4 Example 1-5-4 HA-APBA
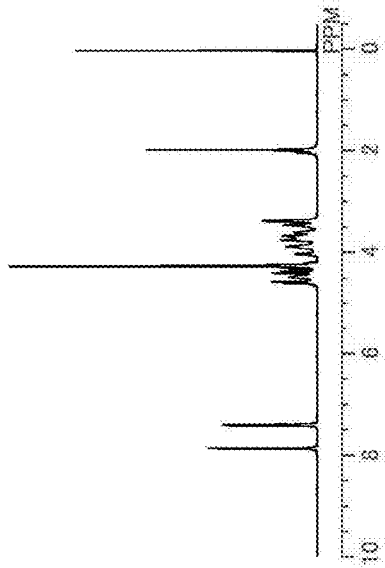
FIG. 4-6 Example 1-5-6 HA-AMBA

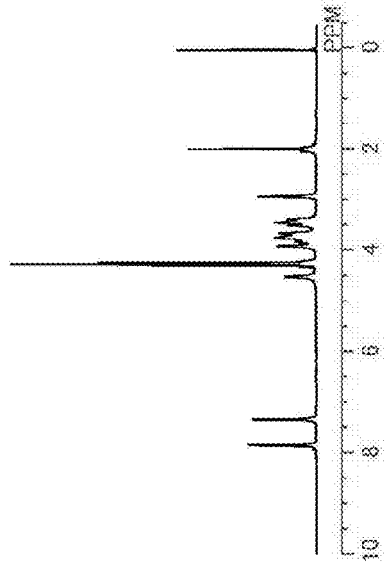
FIG. 4-8    Example 1-5-8
            HA-APhPA
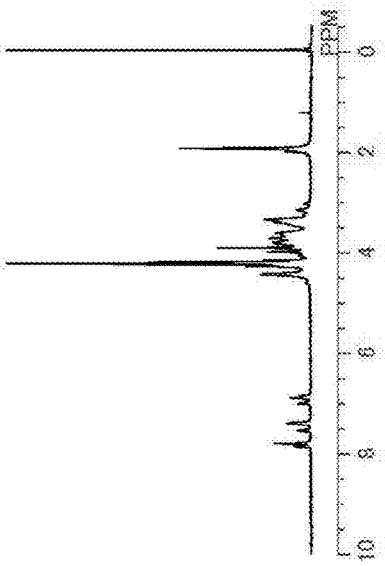
FIG. 4-9    Example 1-5-9
            HA-AEBA
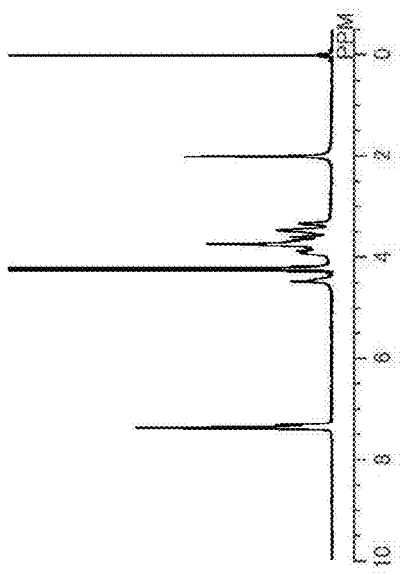
FIG. 4-10   Example 1-5-10
            HA-AMCIBA
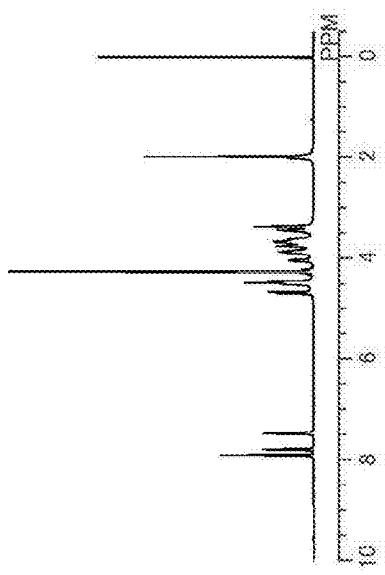
FIG. 4-11   Example 1-5-11
            HA-AMSA

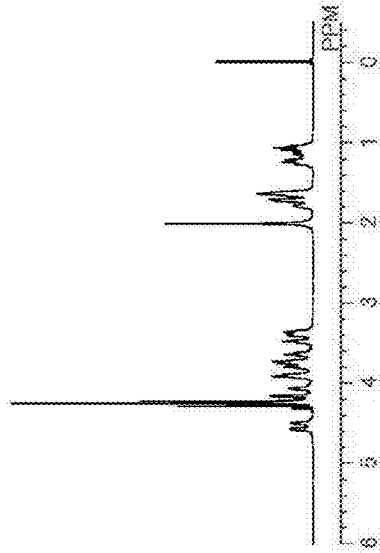
FIG. 4-13    Example 1-5-13
             HA-Chg
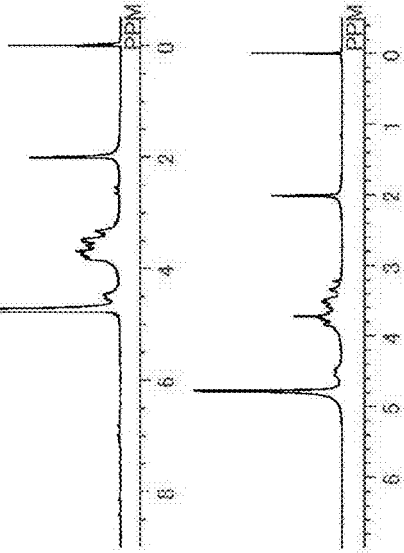
FIG. 5-1    Comparative Example 1-1-1
            HA-FL (upper),
            HA-EDOBEA with low modification degree (lower)
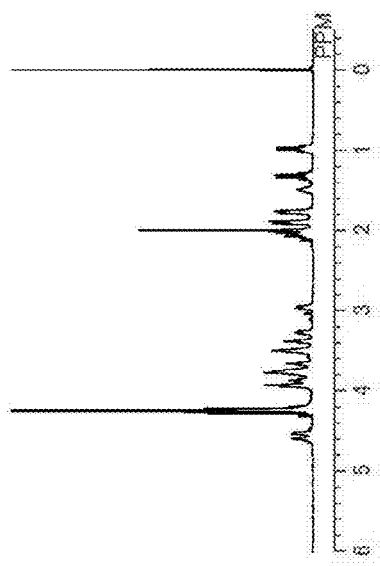
FIG. 4-12    Example 1-5-12
             HA-4AMCHCA
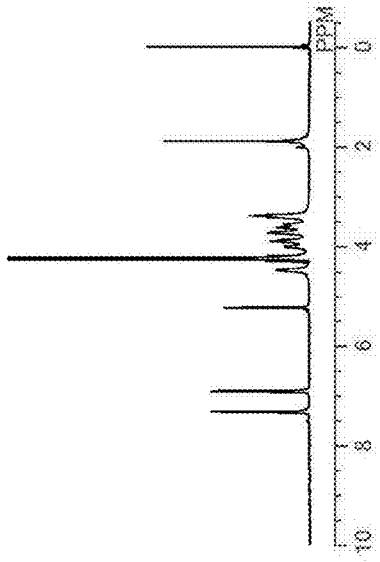
FIG. 4-14    Example 1-5-14
             HA-pHPhg

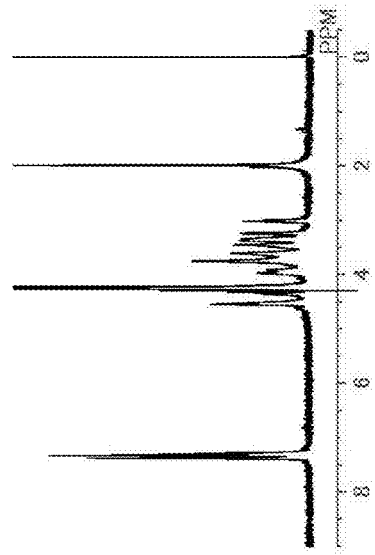
FIG. 5-2  Comparative Example 1-1-2
HA-EDOBEA-Ac/Fl (upper),
HA-EDOBEA with high modification degree (lower)
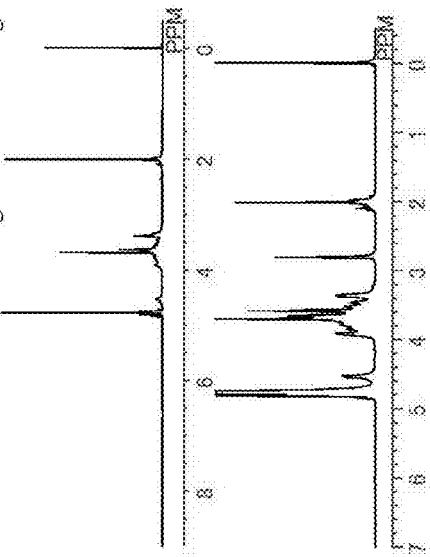
FIG. 5-3  Comparative Example 1-1-3
HA-Phe/Fl
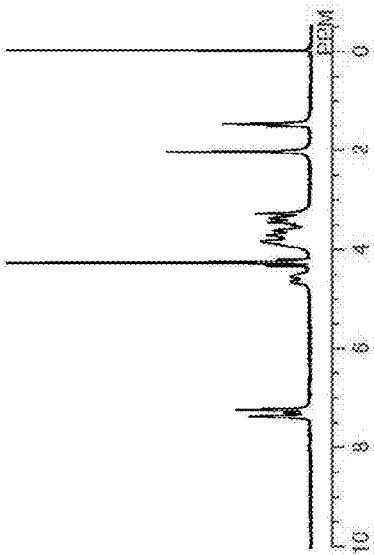
FIG. 5-4  Comparative Example 1-1-4
HA-Tyr/Fl
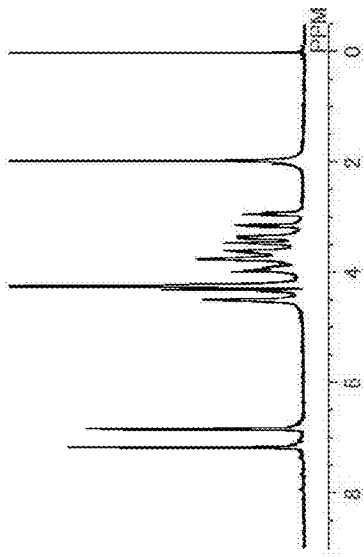
FIG. 5-5  Comparative Example 1-1-5
HA-MePhe/Fl

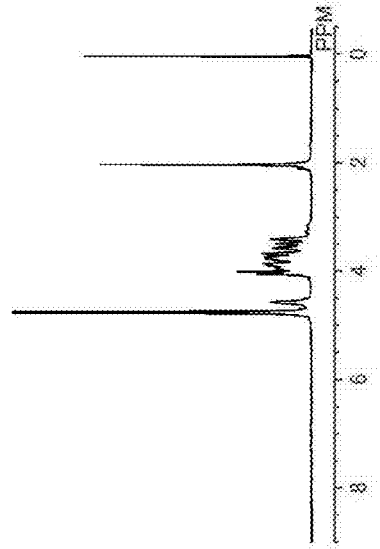
FIG. 5-6  Comparative Example 1-1-6
HA-Pro-OMe/FL
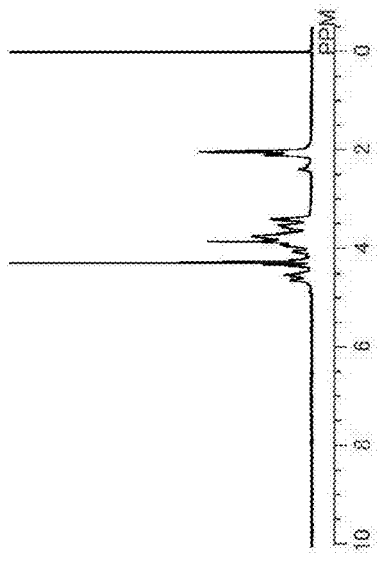
FIG. 5-7  Comparative Example 1-1-7
HA-Gly-NH₂/Rh
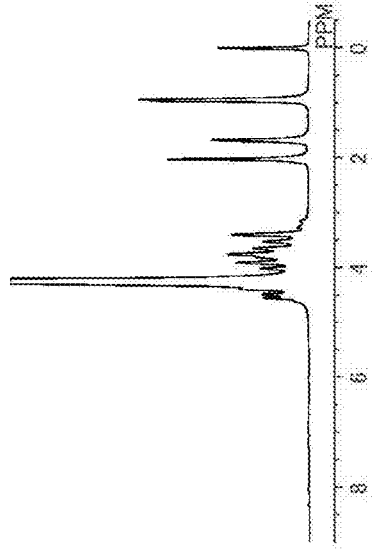
FIG. 5-8  Comparative Example 1-1-8
HA-Ser-NH₂/Rh
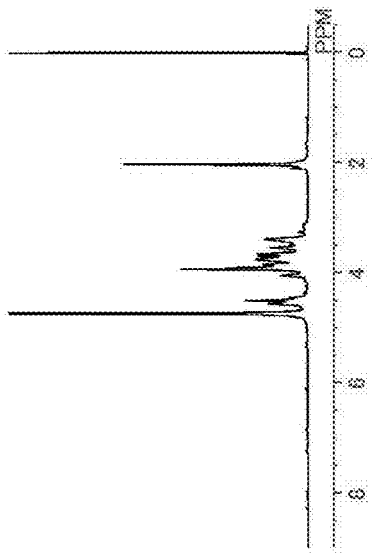
FIG. 5-9  Comparative Example 1-1-9
HA-Leu-NH₂/Rh

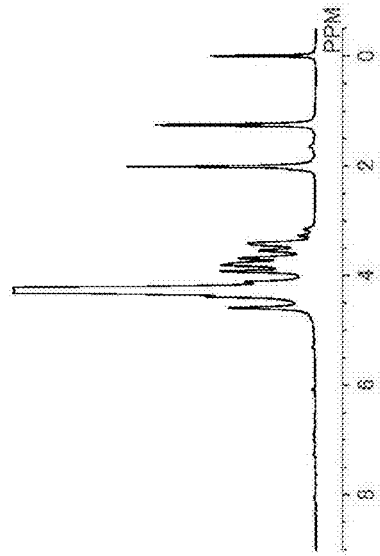
FIG. 5-10  Comparative Example 1-1-10
HA-Ile-NH₂/Rh
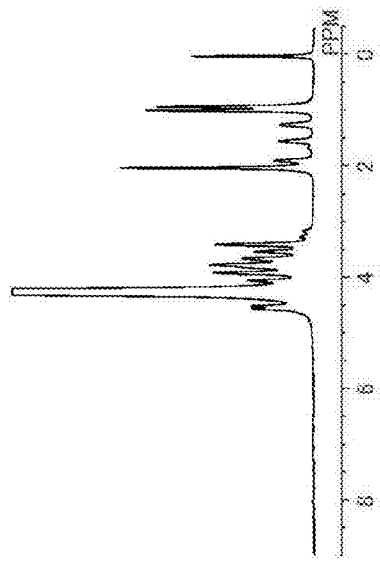
FIG. 5-11  Comparative Example 1-1-11
HA-Thr-NH₂/Rh
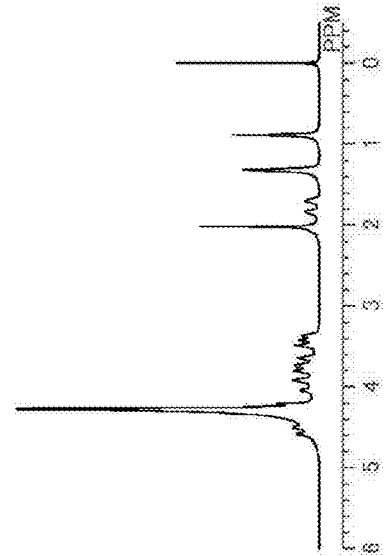
FIG. 5-12  Comparative Example 1-1-12
HA-Gln-NH₂/Rh
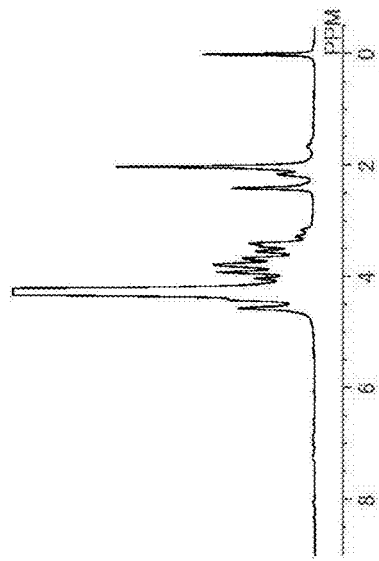
FIG. 6-1  Comparative Example 1-2-1
HA-Nle

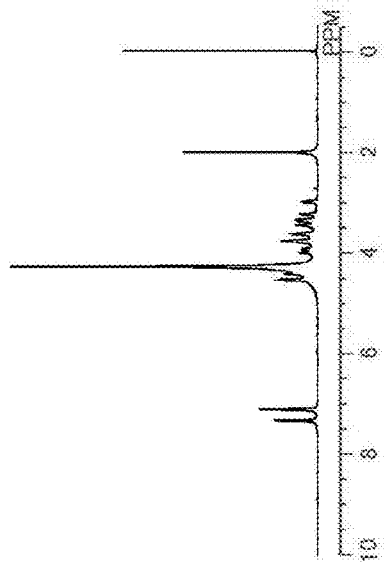
FIG. 6-2    Comparative Example 1-2-2
            HA-tLeu
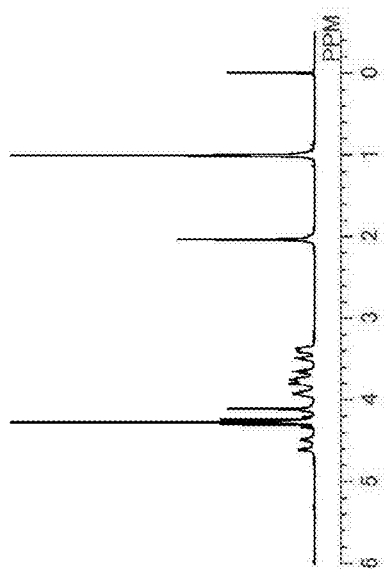
FIG. 6-3    Comparative Example 1-2-3
            HA-pFPhe
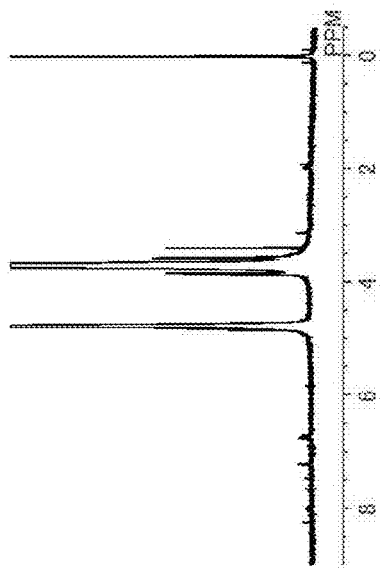
FIG. 6-4    Comparative Example 1-2-4
            HA-Phg
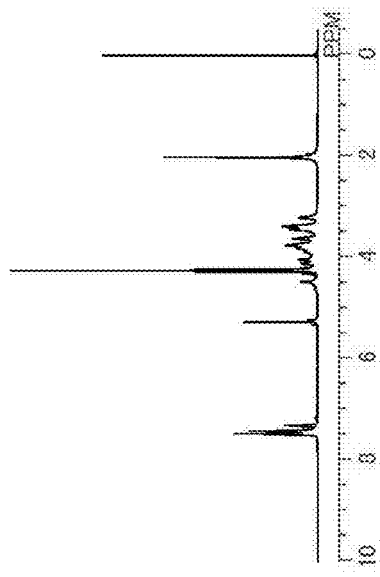
FIG. 7      Comparative Example 1-3
            PEG-FL FIG. 8  Example 3-2-2
Time courses of sample concentrations in rat plasma (group average; μg/mL)

| Ex. No.<br>Time after<br>dose (h) | 1-4-1<br>HA-Ala/FL | 1-4-2<br>HA-Ser/FL | 1-4-3<br>HA-Glu/FL | 1-4-4<br>HA-Gly/FL | 1-4-5<br>HA-Val/FL | 1-4-6<br>HA-Leu/FL | 1-4-7<br>HA-Ile/FL | 1-4-8<br>HA-Thr/FL | 1-4-9<br>HA-Asp/FL | 1-4-10<br>HA-<br>cAcHCA/FL | 1-4-11<br>HA-iAcHCA-<br>OEt/FL | 1-4-12<br>HA-Aib/FL | 1-4-13<br>HA-AcBuCA-<br>OEt/FL |
|---|---|---|---|---|---|---|---|---|---|---|---|---|---|
| 0.0833 | 509.27 | 487.25 | 430.40 | 371.75 | 428.23 | 469.33 | 536.32 | 399.01 | 448.19 | 430.65 | 433.85 | 398.04 | 423.97 |
| 2 | 367.09 | 341.71 | 305.54 | 275.36 | 278.60 | 316.35 | 333.18 | 284.64 | 298.66 | 286.51 | 299.38 | 280.16 | 316.17 |
| 7 | 261.01 | 267.23 | 220.92 | 234.70 | 241.32 | 250.15 | 263.39 | 251.23 | 234.66 | 224.89 | 210.06 | 231.64 | 267.37 |
| 24 | 207.98 | 196.04 | 105.97 | 135.21 | 143.21 | 140.86 | 141.37 | 168.15 | 103.54 | 163.92 | 158.41 | 155.24 | 200.69 |
| 48 | 136.66 | 120.60 | 29.29 | 98.54 | 101.59 | 102.12 | 95.52 | 122.62 | 39.61 | 121.97 | 111.63 | 124.03 | 159.18 |
| 72 | 108.44 | 93.63 | 7.11 | 68.70 | 73.86 | 70.21 | 66.27 | 94.72 | 12.00 | 93.08 | 76.08 | 90.86 | 121.59 |
| 168 | 27.47 | 29.59 | BLQ | 16.38 | 23.30 | 18.24 | 17.18 | 31.69 | BLQ | 29.52 | 20.62 | 29.50 | 44.44 |
| 240 | 2.10 | 3.41 | BLQ | 7.13 | 9.24 | 6.99 | 7.32 | 15.21 | BLQ | 8.32 | 7.03 | 4.99 | 22.04 |
| 336 | BLQ | BLQ | BLQ | 1.87 | 3.14 | 1.44 | 1.81 | 5.88 | BLQ | 3.21 | 1.36 | BLQ | 9.80 |
| LOQ | 1.2 | 1.2 | 1.2 | 1.2 | 1.2 | 1.2 | 1.2 | 1.2 | 1.2 | 1.2 | 1.2 | 1.2 | 1.2 |

| Ex. No.<br>Time after<br>dose (h) | 1-4-14<br>HA-Asn/Rh | 1-4-15<br>HA-Ala-<br>NH₂/Rh | 1-4-16<br>HA-Val-<br>NH₂/Rh | 1-4-17<br>HA-Asn-<br>NH₂/Rh | 1-4-18<br>HA-Me/FL | 1-4-19<br>HA-Pr/FL |
|---|---|---|---|---|---|---|
| 0.0833 | 390.30 | 418.16 | 370.98 | 373.53 | 469.81 | 543.44 |
| 2 | 206.99 | 214.62 | 154.76 | 171.68 | 270.29 | 379.55 |
| 7 | 165.19 | 154.87 | 115.79 | 117.97 | 224.48 | 262.91 |
| 24 | 106.56 | 96.66 | 67.95 | 78.46 | 146.32 | 159.37 |
| 48 | 62.86 | 58.98 | 43.88 | 47.19 | 96.93 | 105.20 |
| 72 | 47.13 | 40.55 | 32.15 | 36.01 | 75.15 | 91.62 |
| 168 | 13.01 | 11.14 | 7.78 | 9.16 | 27.36 | 34.51 |
| 240 | 4.21 | 3.74 | 4.10 | 3.19 | 14.87 | 17.41 |
| 336 | BLQ | 3.14 | 3.28 | BLQ | 9.76 | 10.53 |
| LOQ | 2.5 | 2.5 | 2.5 | 2.5 | 1.2 | 1.2 |

| Com.Ex.No.<br>Time after<br>dose (h) | 1-1-1<br>HA-FL | 1-1-2<br>HA-EDOBEA-<br>Ac/FL | 1-1-3<br>HA-Phe/FL | 1-1-4<br>HA-Tyr/FL | 1-1-5<br>HA-<br>MePhe/FL | 1-1-6<br>HA-Pro-<br>OMe/FL | 1-1-7<br>HA-Gly-<br>NH₂/Rh | 1-1-8<br>HA-Ser-<br>NH₂/Rh | 1-1-9<br>HA-Leu-<br>NH₂/Rh | 1-1-10<br>HA-Ile-<br>NH₂/Rh | 1-1-11<br>HA-Thr-<br>NH₂/Rh | 1-1-12<br>HA-Gln-<br>NH₂/Rh | 1-3<br>PEG-FL<br>(30kDa) |
|---|---|---|---|---|---|---|---|---|---|---|---|---|---|
| 0.0833 | 507.01 | 456.19 | 305.57 | 355.36 | 412.48 | 517.02 | 306.71 | 206.63 | 341.83 | 357.65 | 186.73 | 272.66 | 291.56 |
| 2 | 305.83 | 361.18 | 230.30 | 172.63 | 178.11 | 360.82 | 97.73 | 28.73 | 132.79 | 151.47 | 20.70 | 72.73 | 172.55 |
| 7 | 118.84 | 200.31 | 157.31 | 65.93 | 58.50 | 229.13 | 61.43 | 12.33 | 69.38 | 105.09 | 8.81 | 41.47 | 102.62 |
| 24 | BLQ | 251.73 | 37.47 | BLQ | 6.35 | 67.09 | 28.08 | 4.86 | 45.75 | 55.05 | 2.67 | 18.63 | 32.85 |
| 48 | BLQ | 181.50 | 3.27 | BLQ | BLQ | 9.58 | 16.44 | 3.09 | 26.06 | 35.57 | BLQ | 10.21 | 8.99 |
| 72 | BLQ | 142.96 | BLQ | BLQ | BLQ | 1.17 | 11.06 | BLQ | 18.29 | 22.74 | BLQ | 5.94 | 4.37 |
| 168 | BLQ | 58.21 | BLQ | BLQ | BLQ | BLQ | BLQ | BLQ | 5.19 | 5.89 | BLQ | BLQ | 1.28 |
| 240 | BLQ | - | BLQ | BLQ | BLQ | BLQ | BLQ | BLQ | 2.70 | 3.05 | BLQ | BLQ | 0.97 |
| 336 | BLQ | 24.81 | BLQ | BLQ | BLQ | BLQ | BLQ | BLQ | 2.23 | BLQ | BLQ | BLQ | 0.66 |
| LOQ | 1.2 | 1.2 | 2.5 | 2.5 | 1.2 | 1.2 | 2.5 | 2.5 | 2.0 | 2.0 | 2.0 | 2.0 | 0.5 |

*1) BLQ: Below LOQ
*2) --: No data available

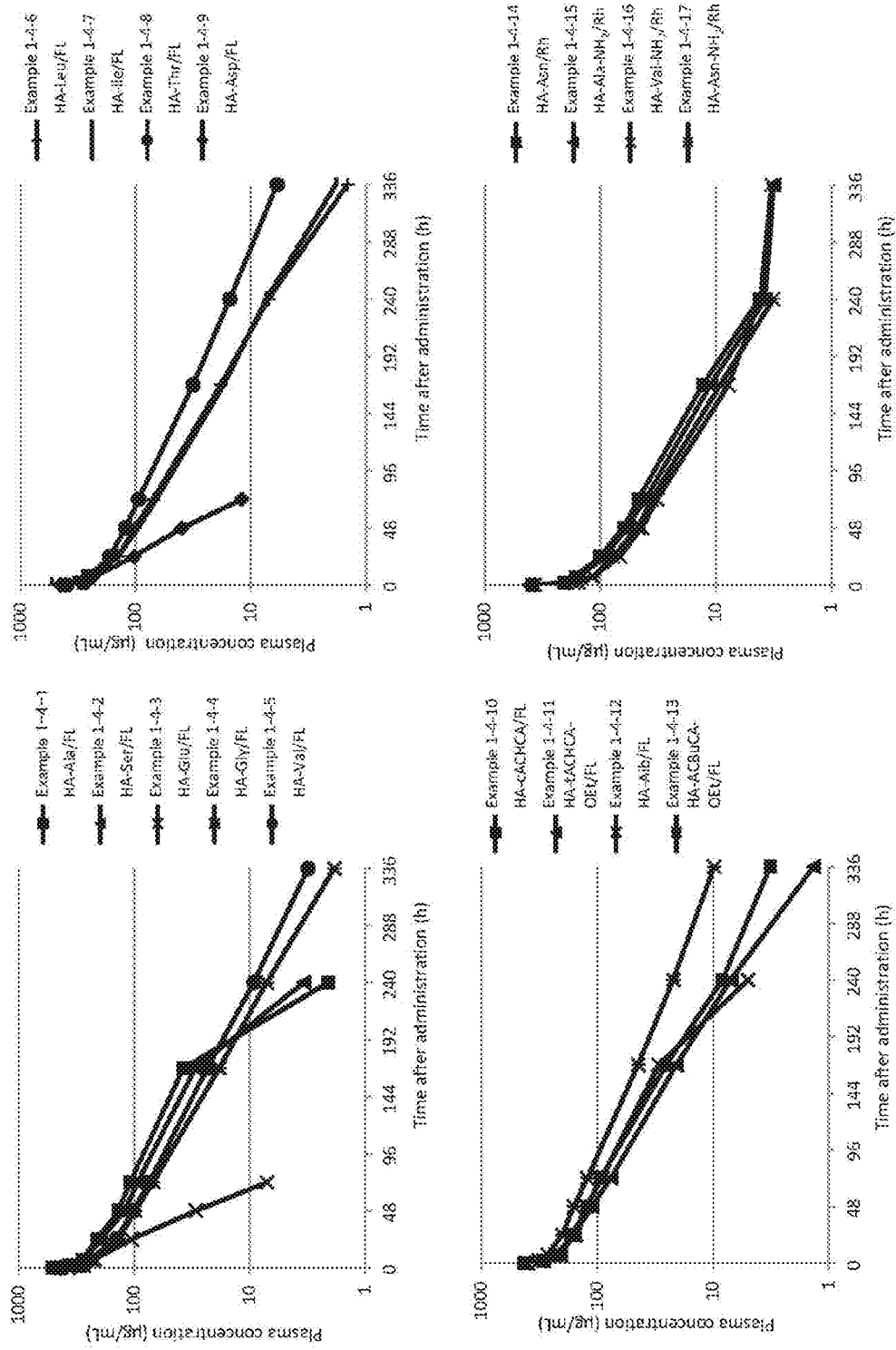
FIG. 9-1  Example 3-2-2  Time courses of sample concentrations in rat plasma (charts)

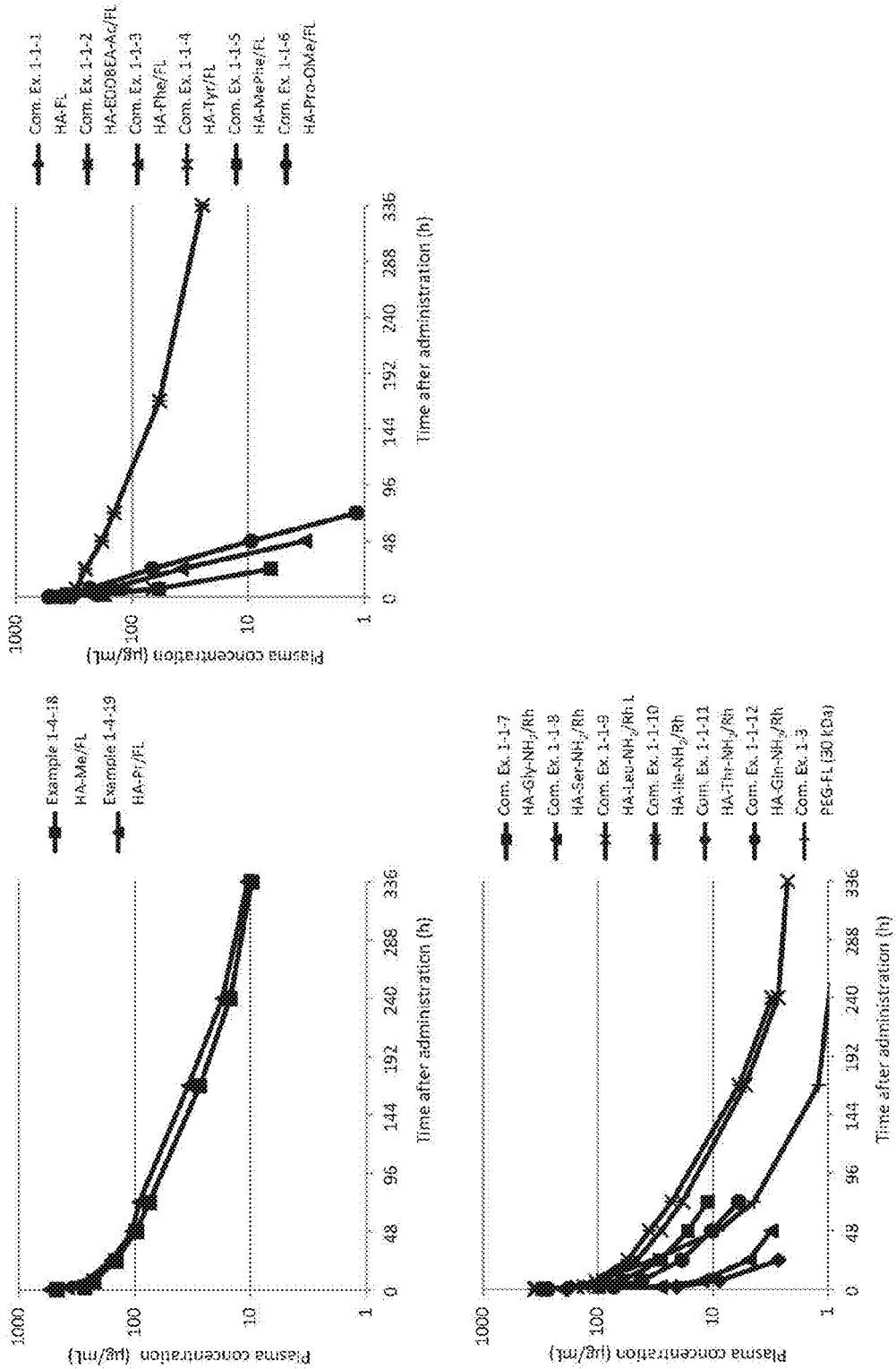
FIG. 9-2  Example 3-2-2
Time courses of sample concentrations in rat plasma (charts)

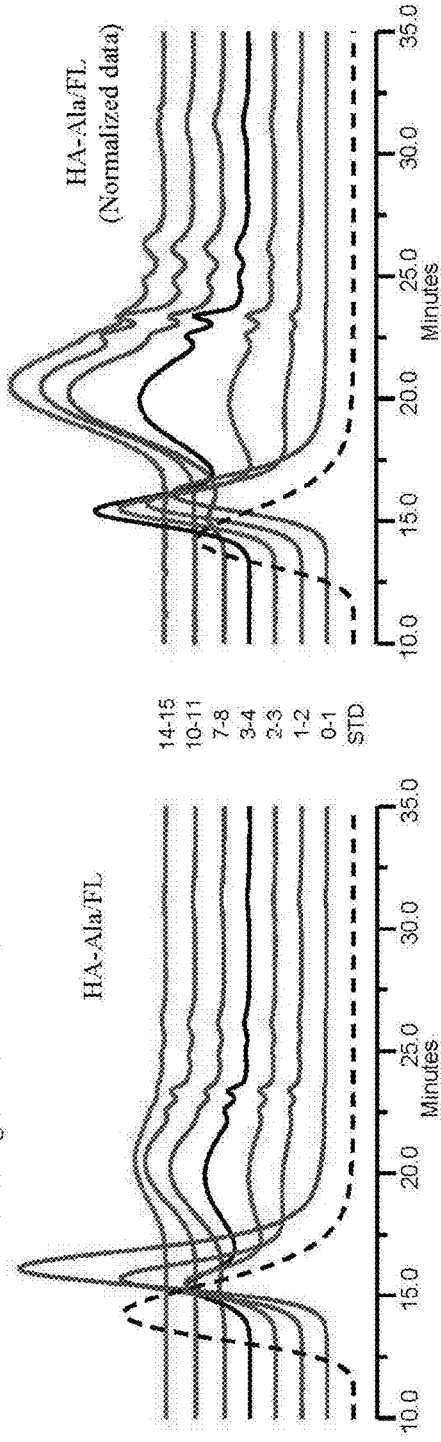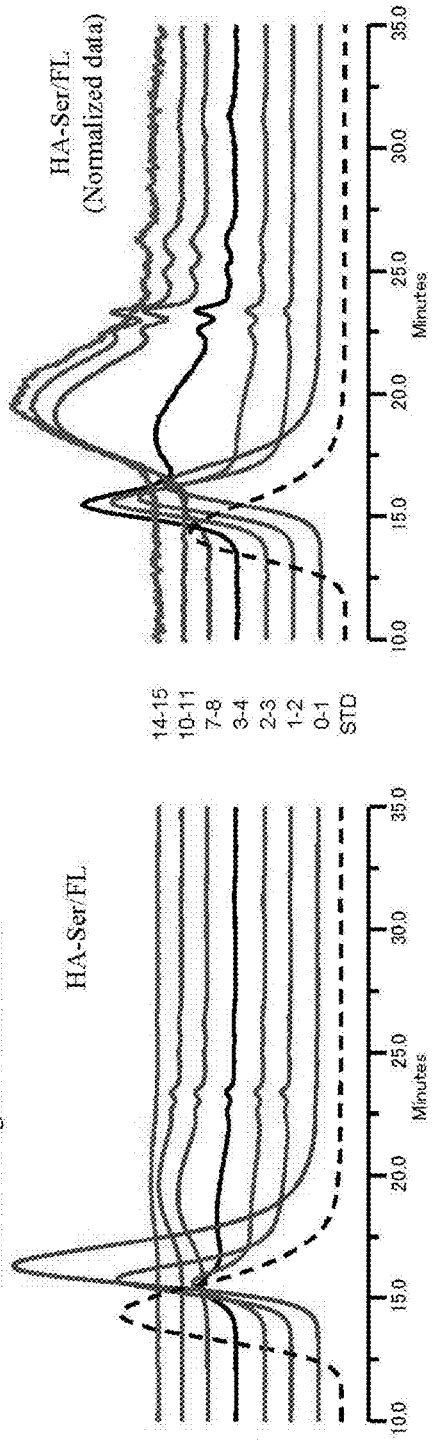
FIG. 10-1  Example 3-3-2 SEC chromatograms of rat urines
FIG. 10-2  Example 3-3-2 SEC chromatograms of rat urines

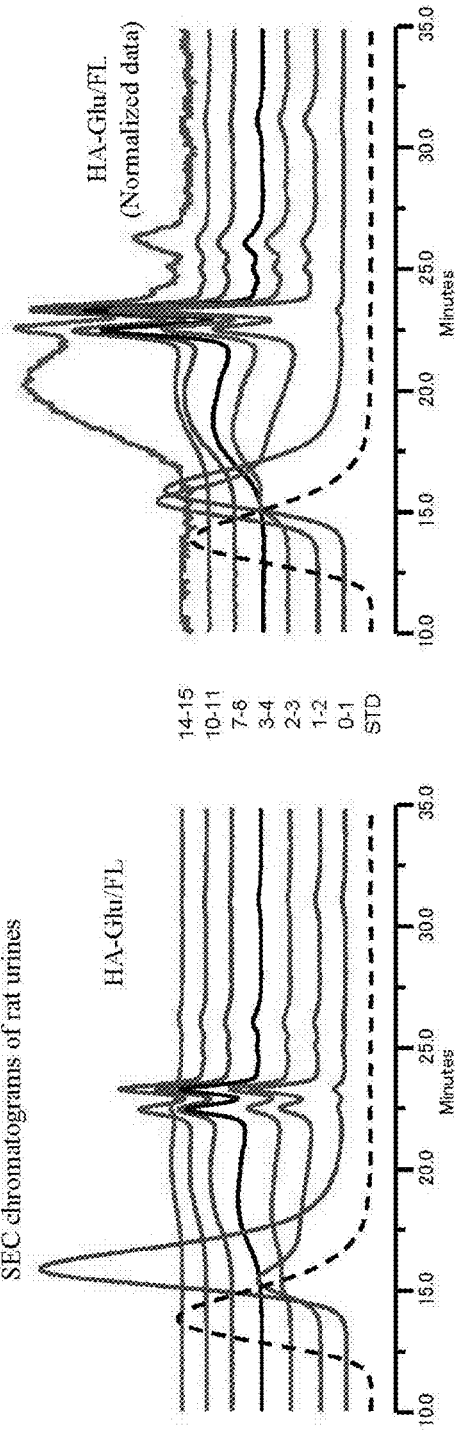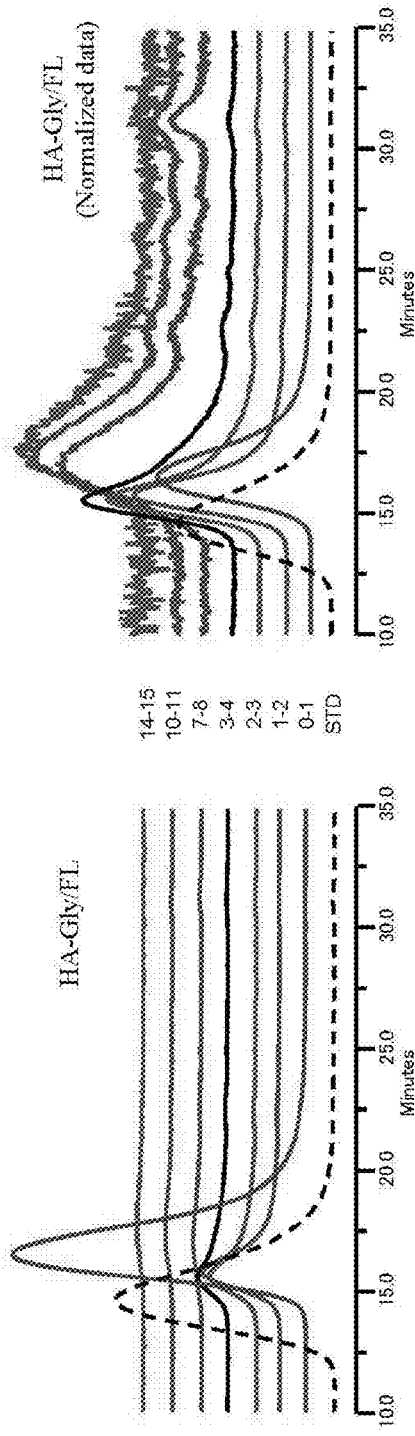
FIG. 10-3  Example 3-3-2
SEC chromatograms of rat urines
FIG. 10-4  Example 3-3-2
SEC chromatograms of rat urines

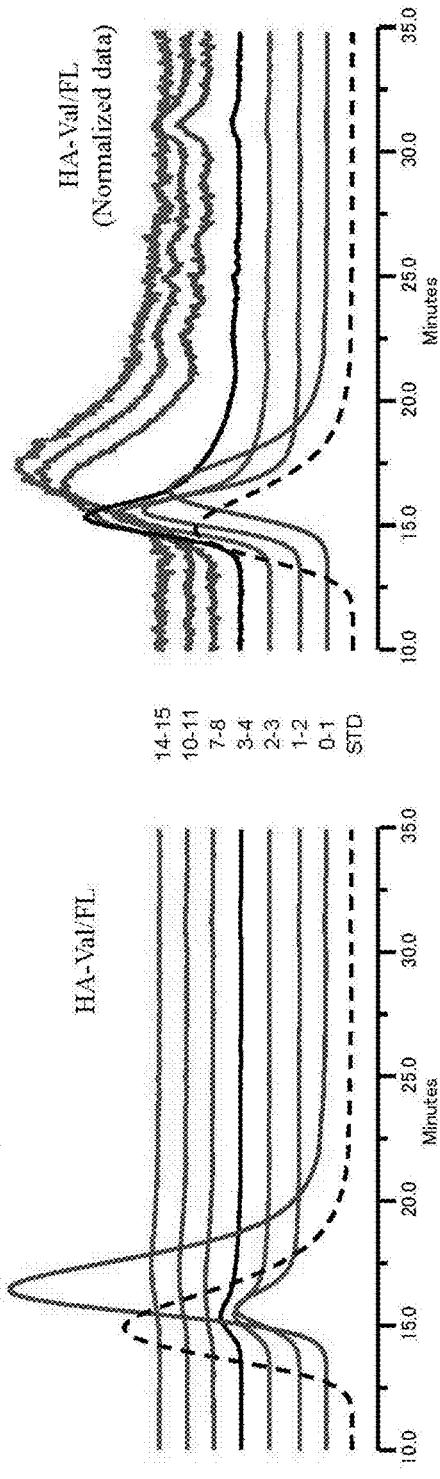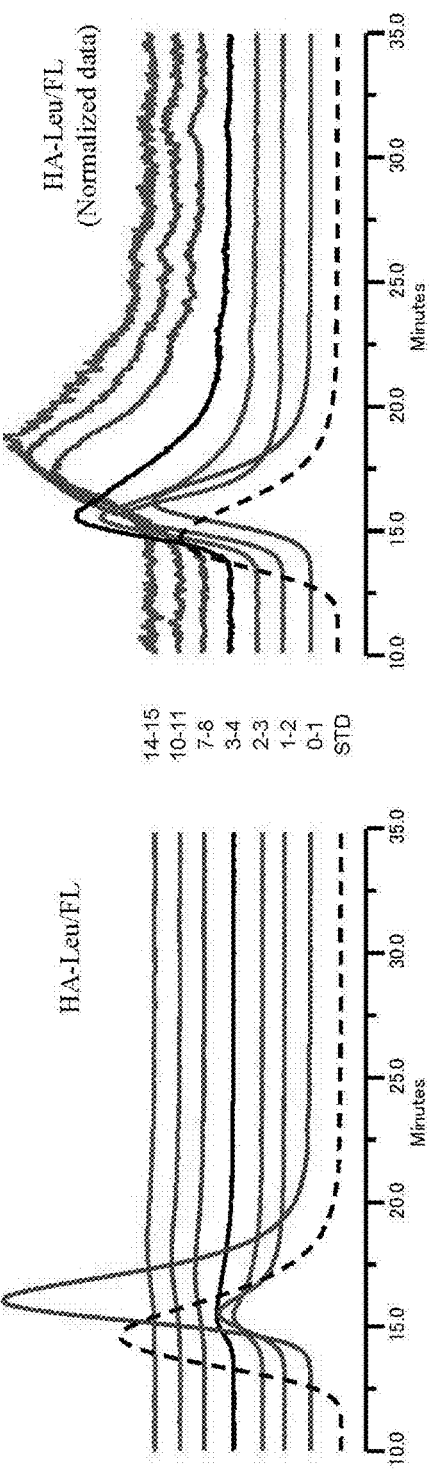
FIG. 10-5   Example 3-3-2
SEC chromatograms of rat urines
FIG. 10-6   Example 3-3-2
SEC chromatograms of rat urines

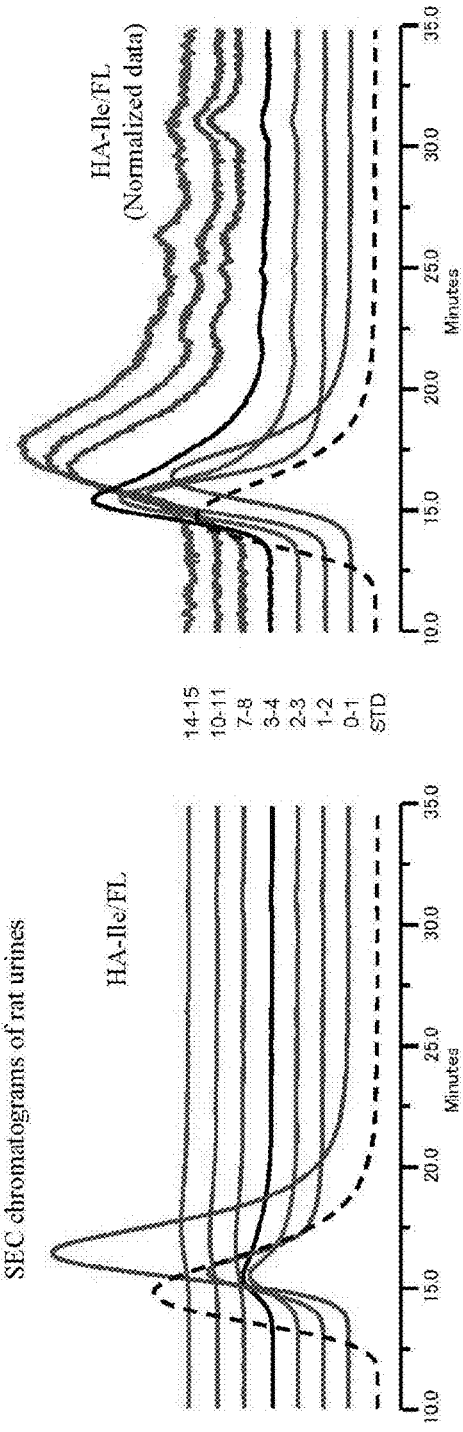
FIG. 10-7  Example 3-3-2
SEC chromatograms of rat urines
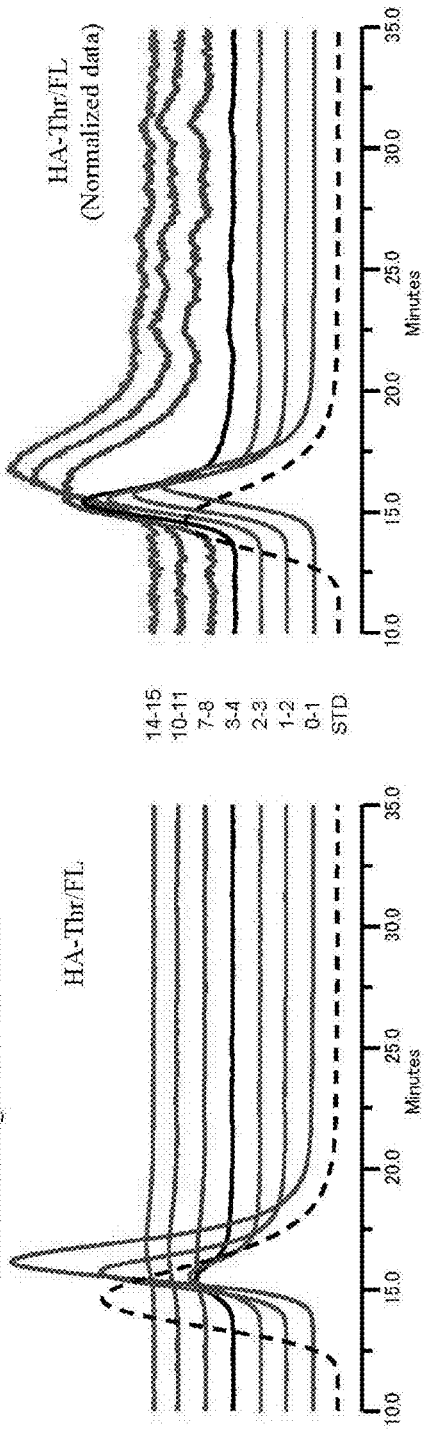
FIG. 10-8  Example 3-3-2
SEC chromatograms of rat urines

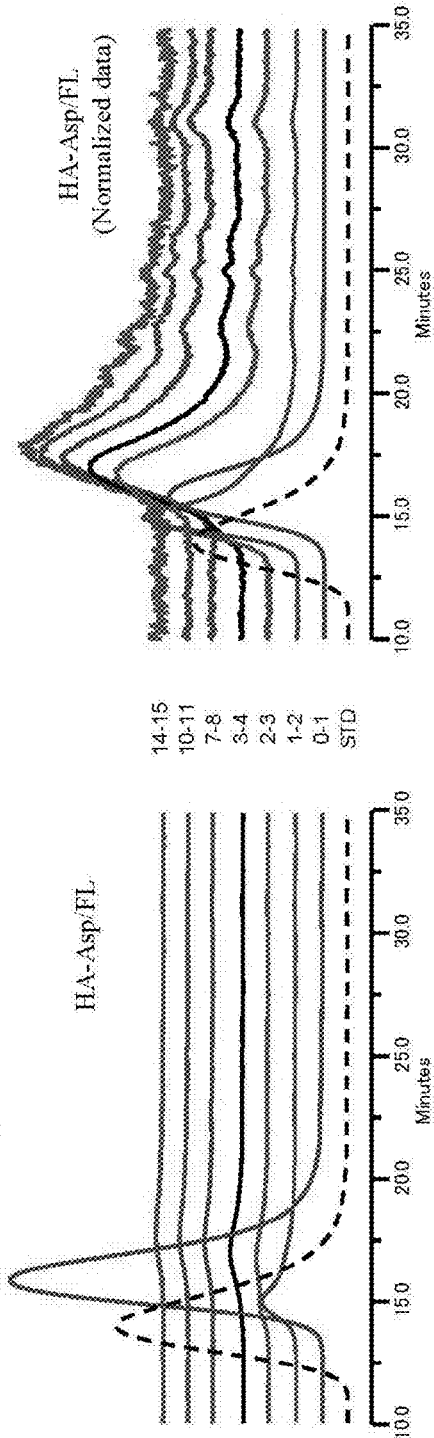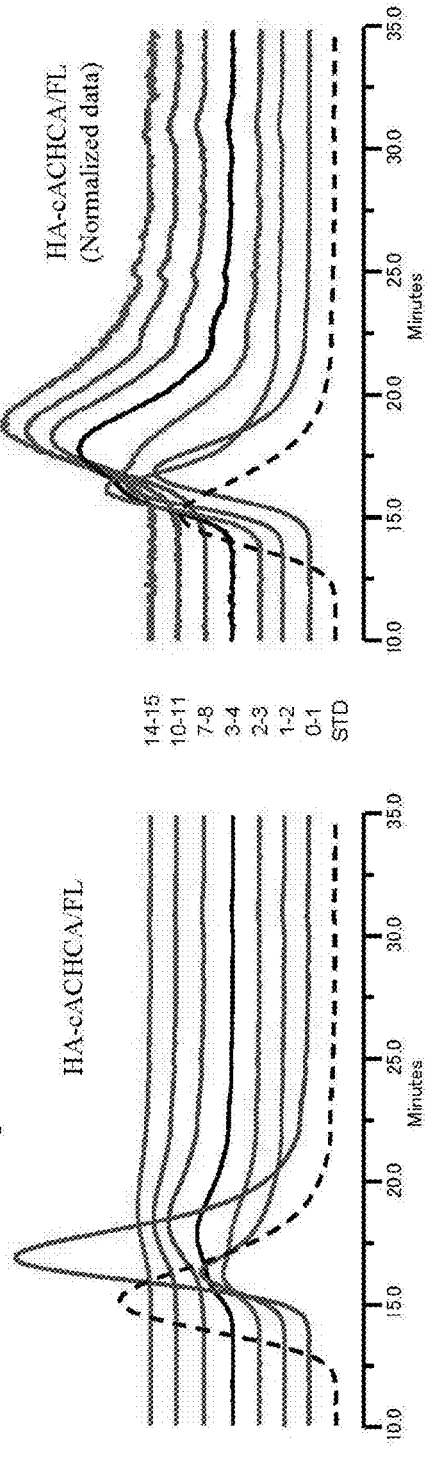
FIG. 10-9  Example 3-3-2
SEC chromatograms of rat urines
FIG. 10-10  Example 3-3-2
SEC chromatograms of rat urines

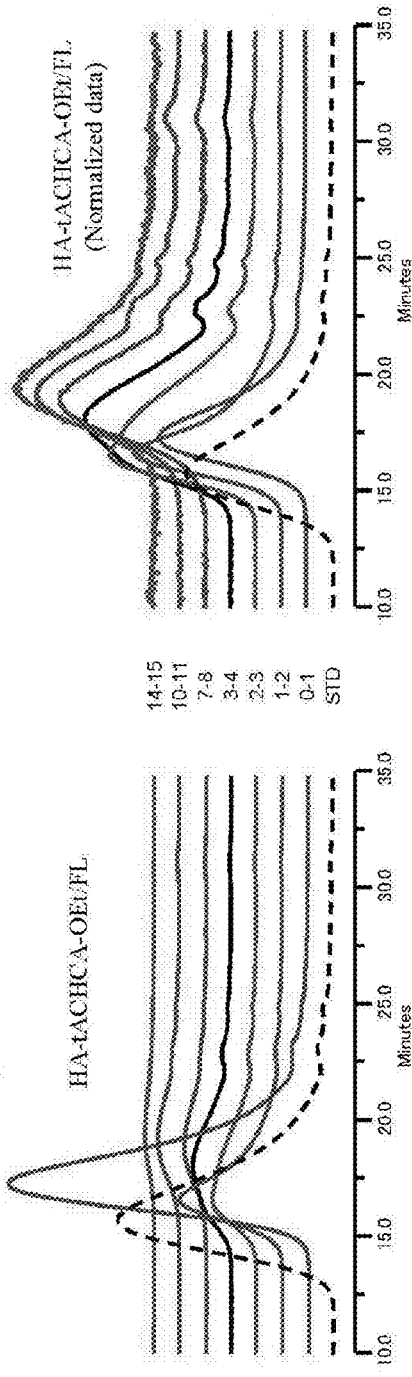
FIG. 10-11 Example 3-3-2 SEC chromatograms of rat urines
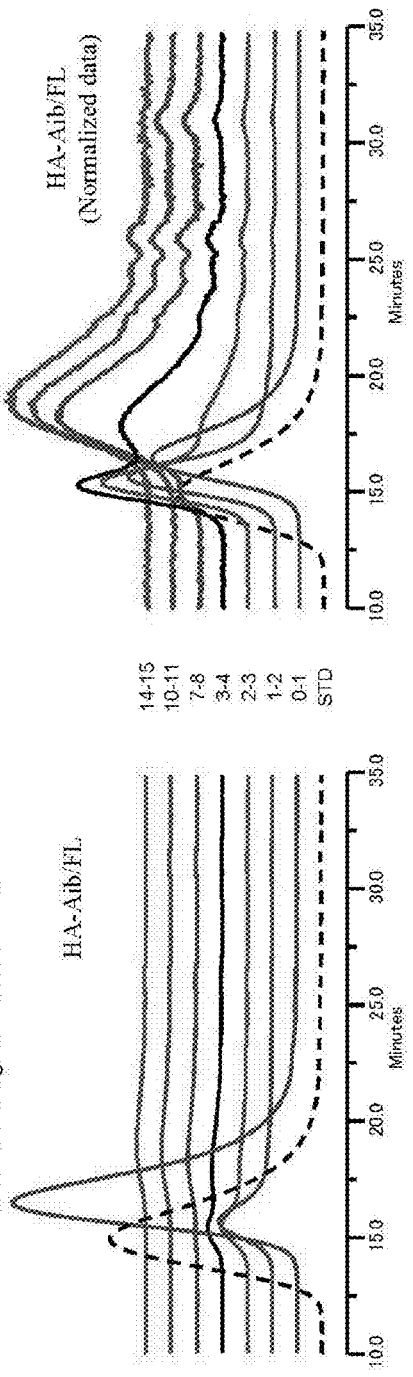
FIG. 10-12 Example 3-3-2 SEC chromatograms of rat urines

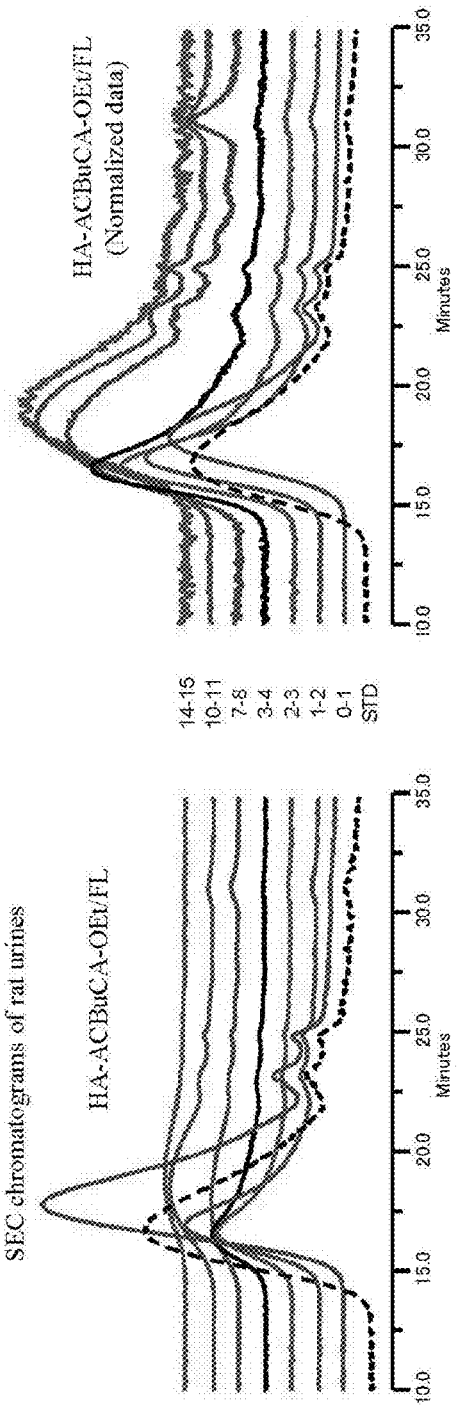
FIG. 10-13  Example 3-3-2
SEC chromatograms of rat urines
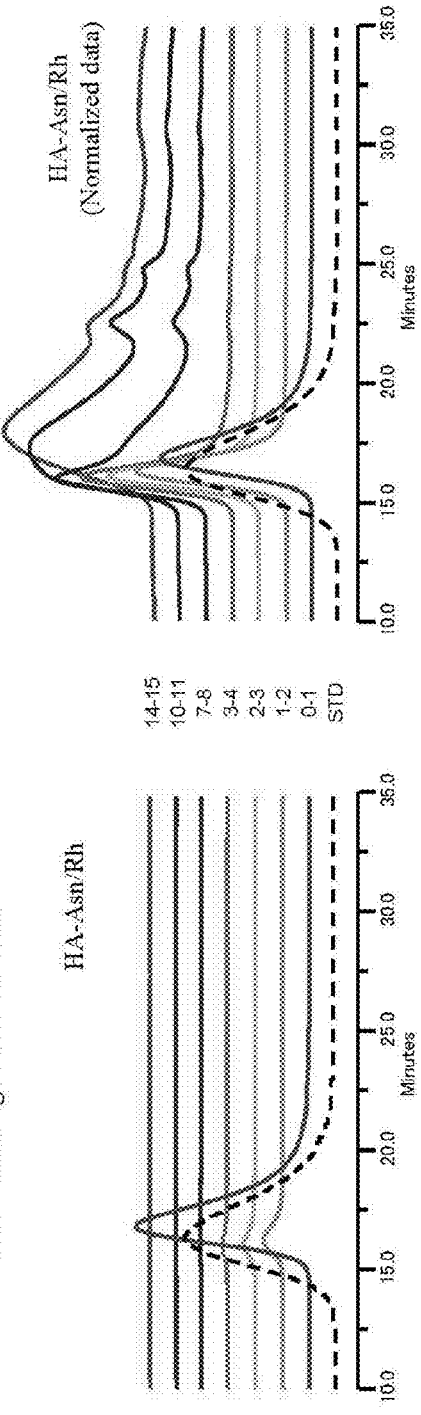
FIG. 10-14  Example 3-3-2
SEC chromatograms of rat urines

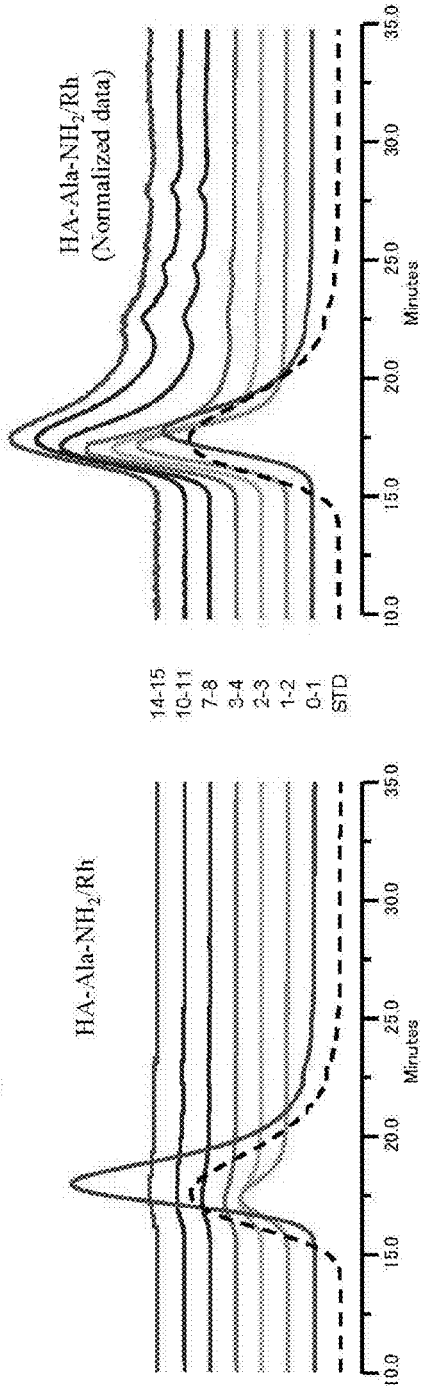
FIG. 10-15  Example 3-3-2
SEC chromatograms of rat urines
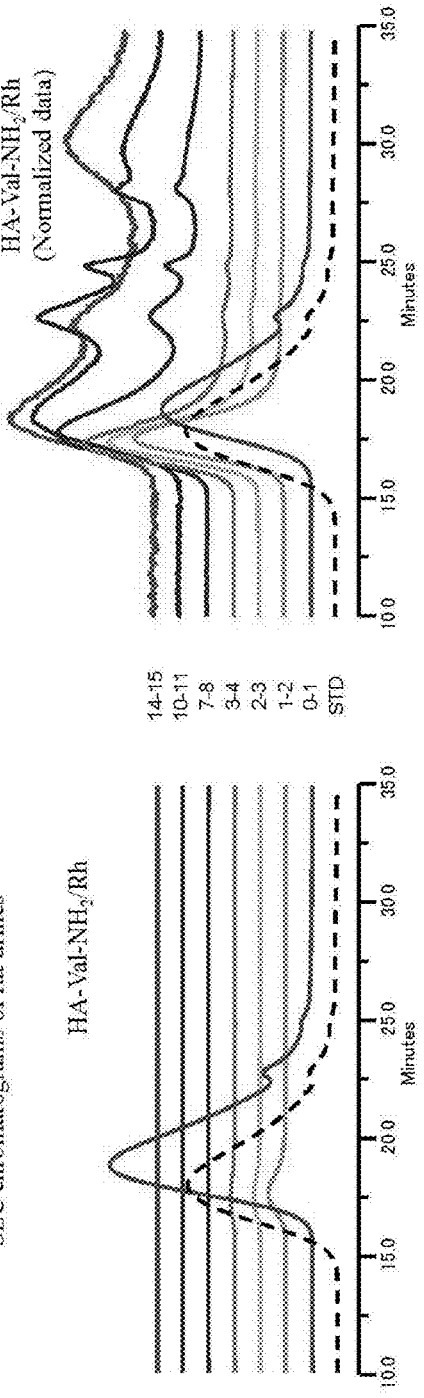
FIG. 10-16  Example 3-3-2
SEC chromatograms of rat urines

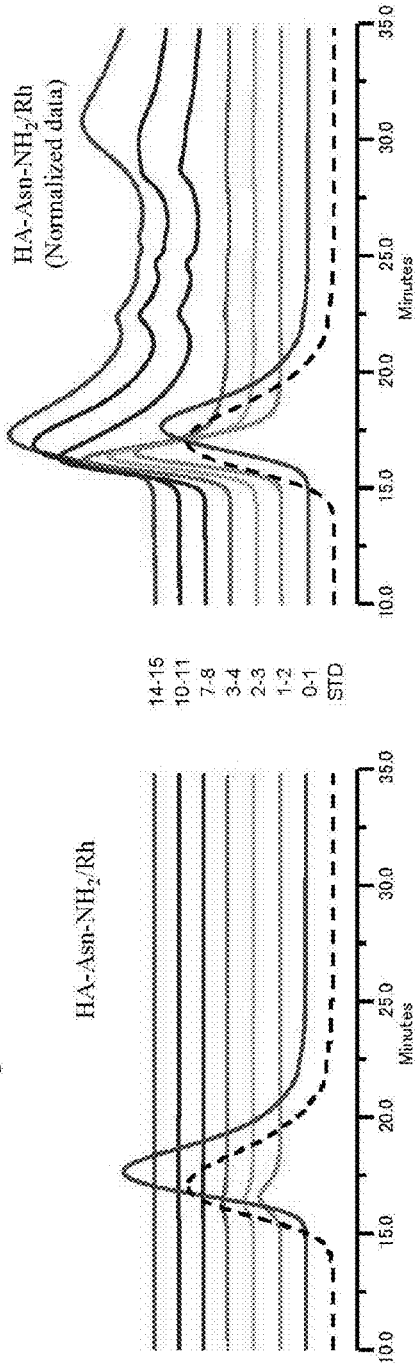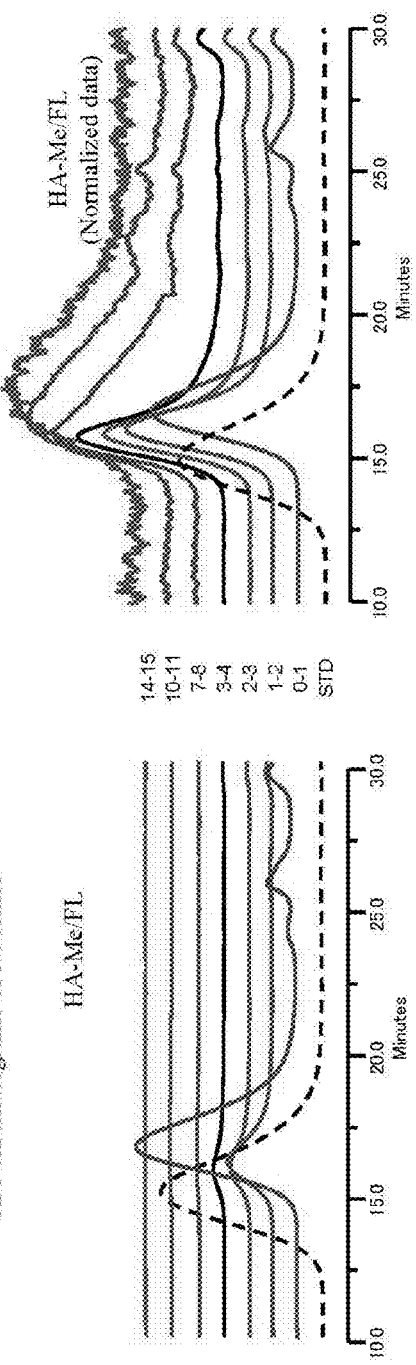
FIG. 10-17  Example 3-3-2
SEC chromatograms of rat urines
FIG. 10-18  Example 3-3-2
SEC chromatograms of rat urines

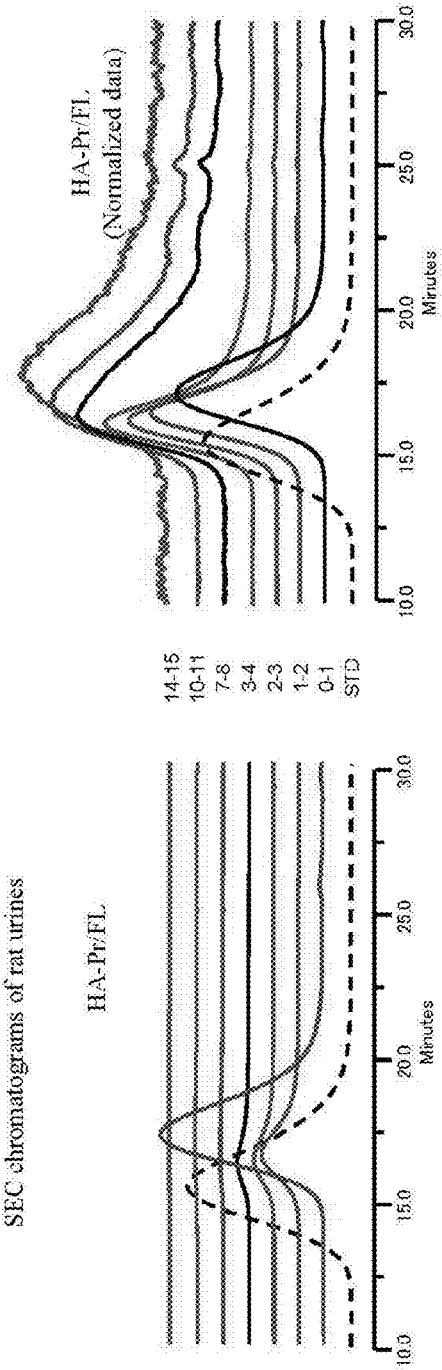
FIG. 10-19  Example 3-3-2
SEC chromatograms of rat urines
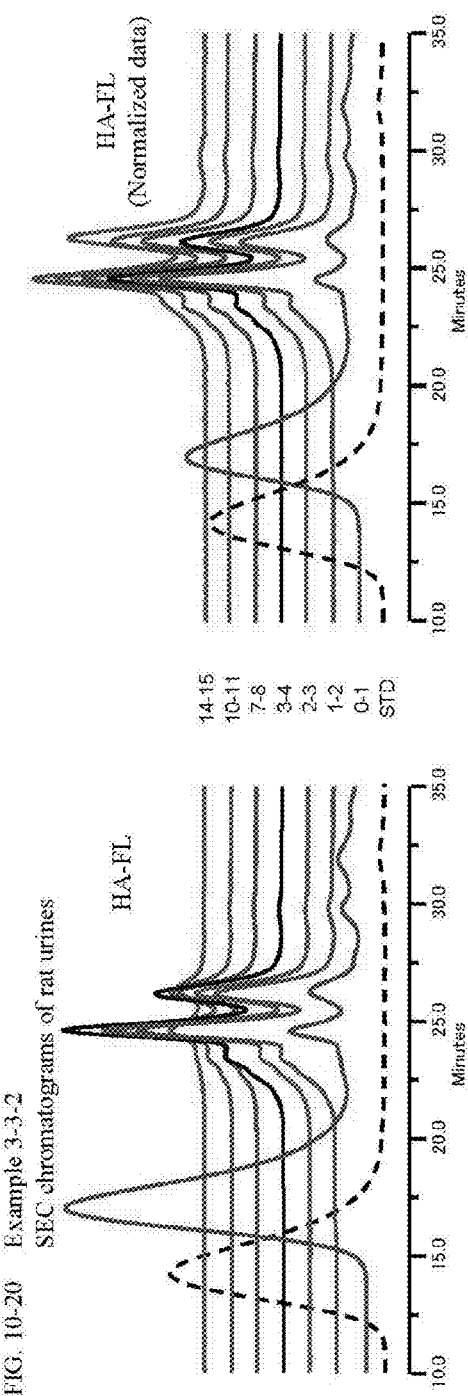
FIG. 10-20  Example 3-3-2
SEC chromatograms of rat urines

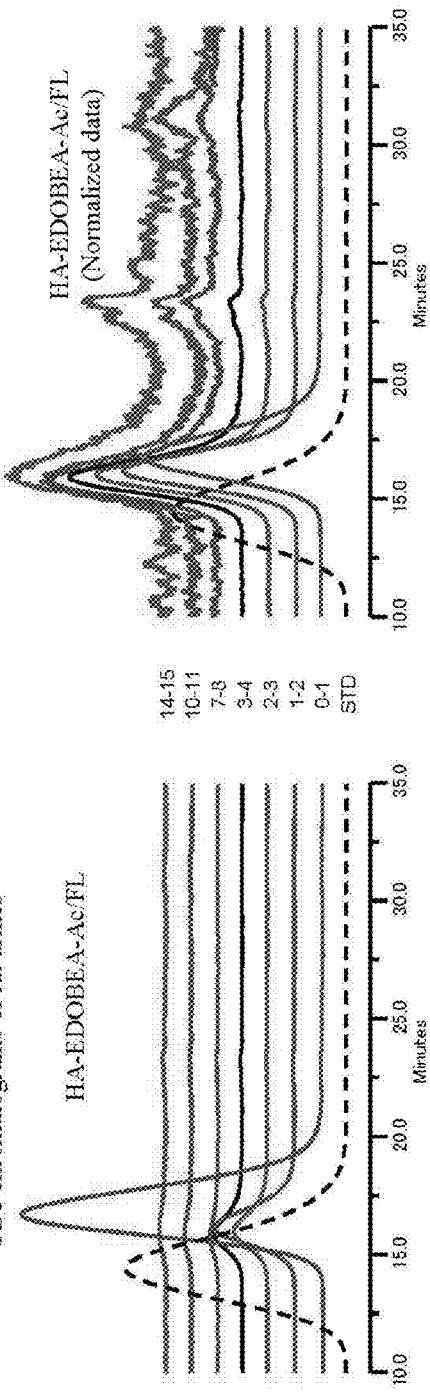
FIG. 10-21  Example 3-3-2
SEC chromatograms of rat urines
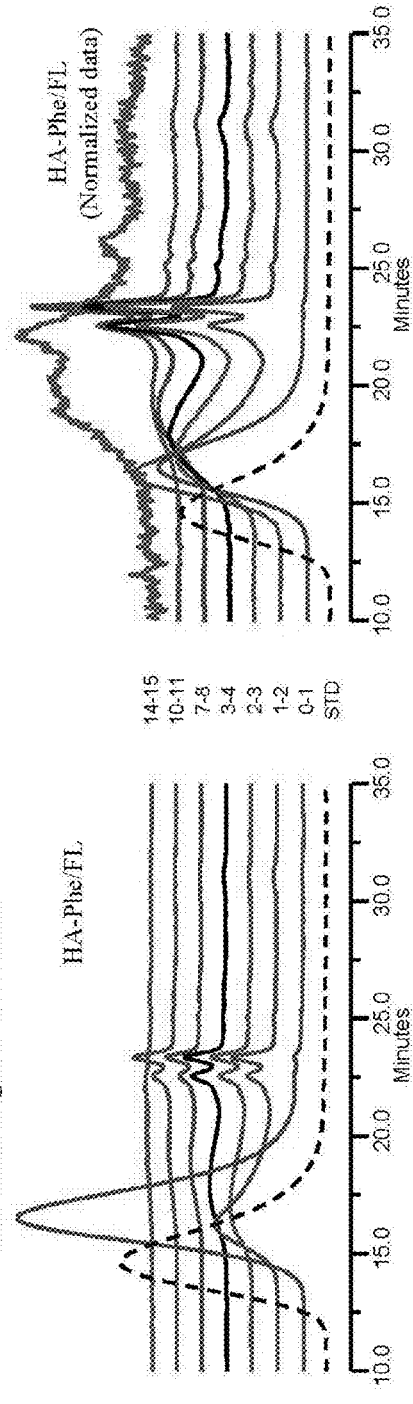
FIG. 10-22  Example 3-3-2
SEC chromatograms of rat urines

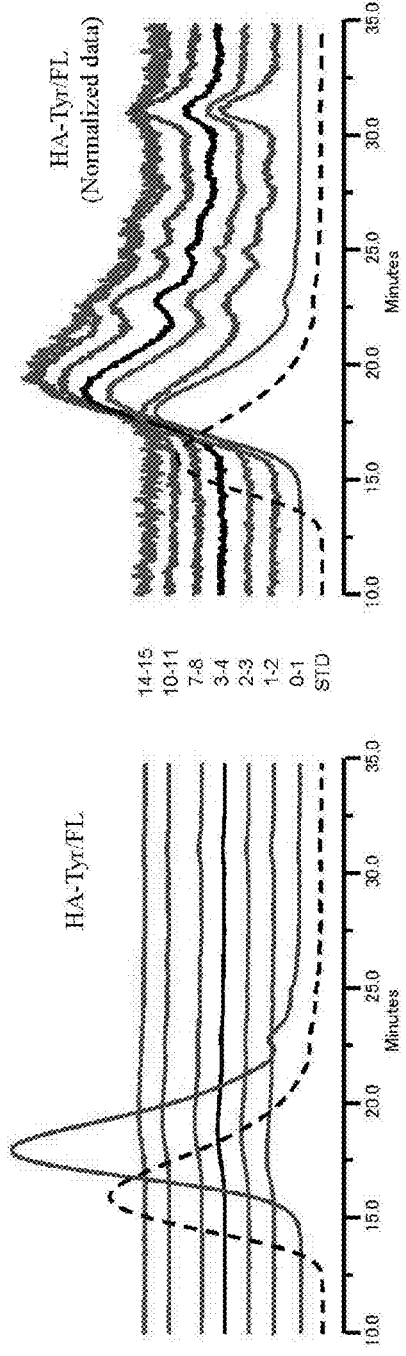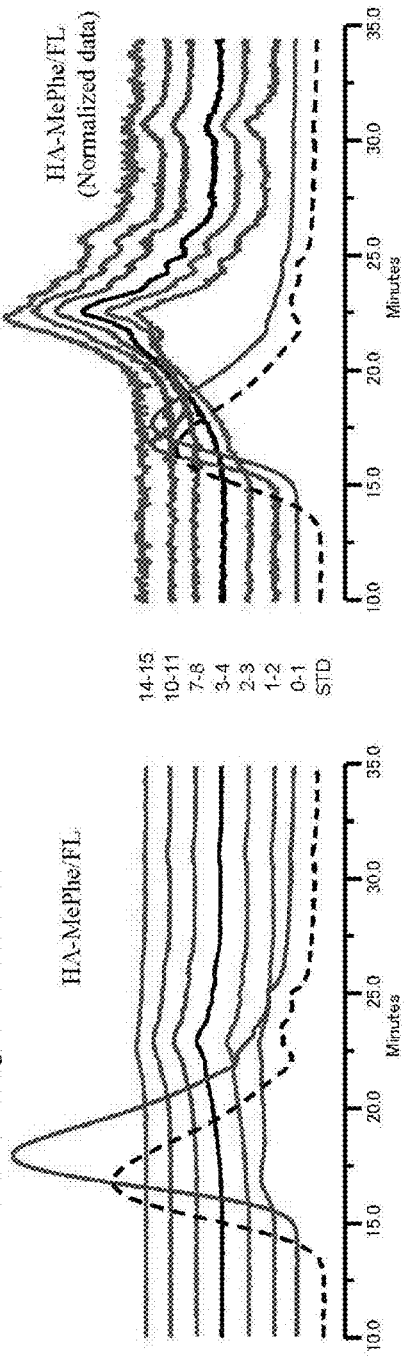
FIG. 10-23  Example 3-3-2
SEC chromatograms of rat urines
FIG. 10-24  Example 3-3-2
SEC chromatograms of rat urines

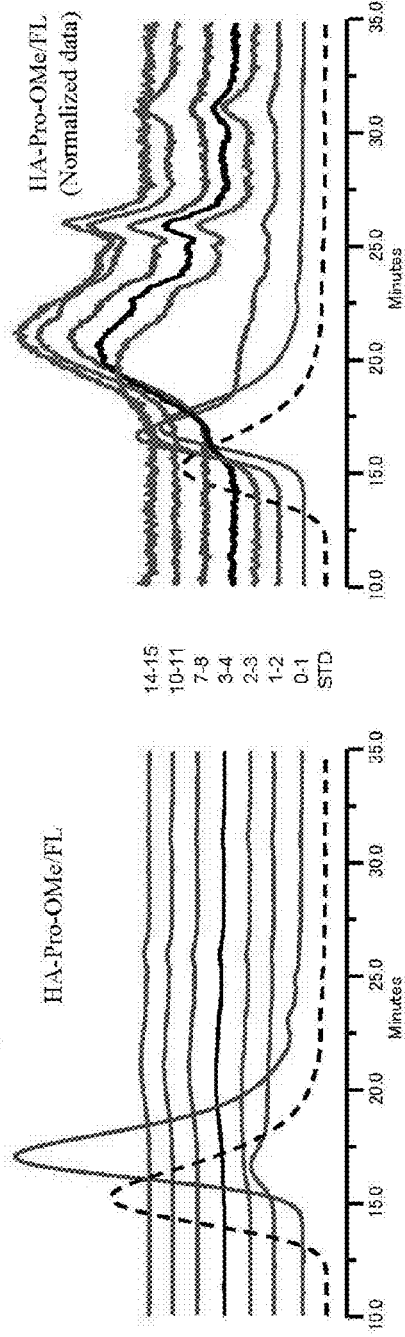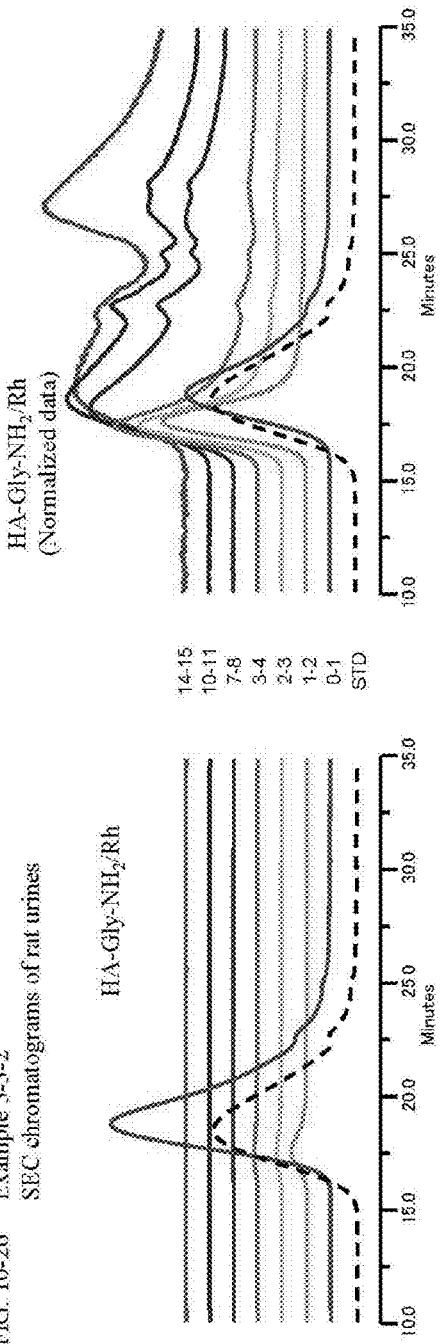
FIG. 10-25  Example 3-3-2
SEC chromatograms of rat urines
FIG. 10-26  Example 3-3-2
SEC chromatograms of rat urines

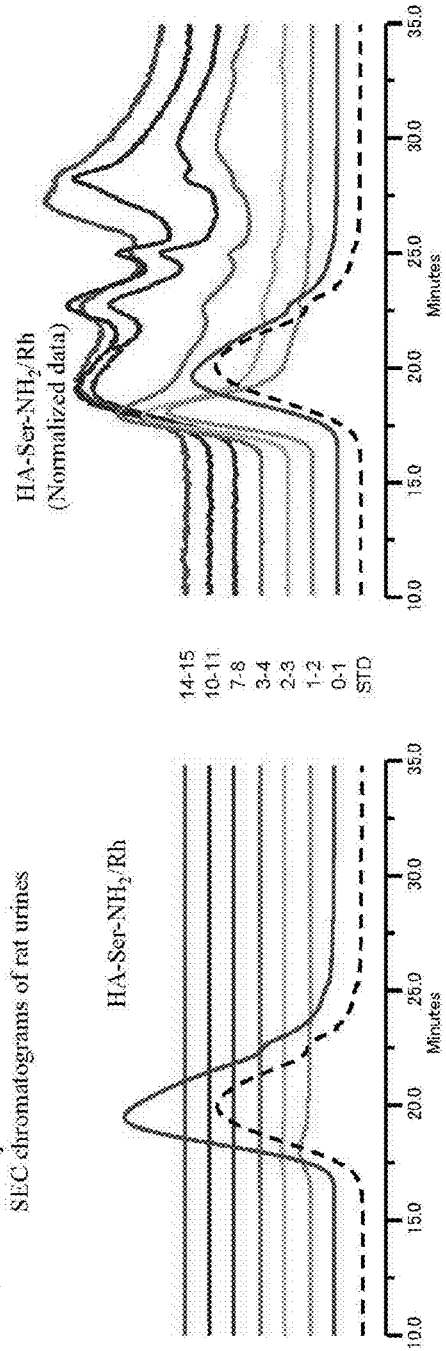
FIG. 10-27  Example 3-3-2
SEC chromatograms of rat urines
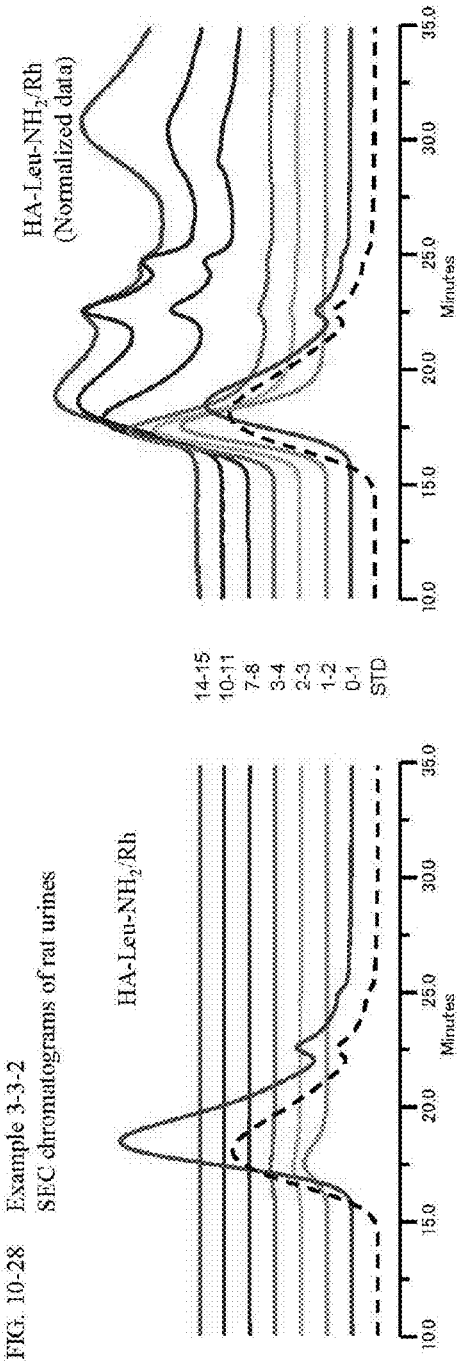
FIG. 10-28  Example 3-3-2
SEC chromatograms of rat urines

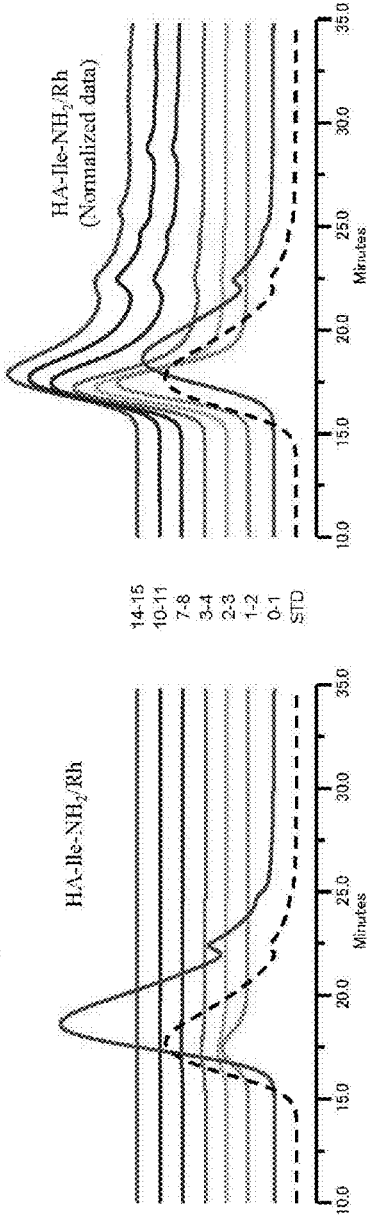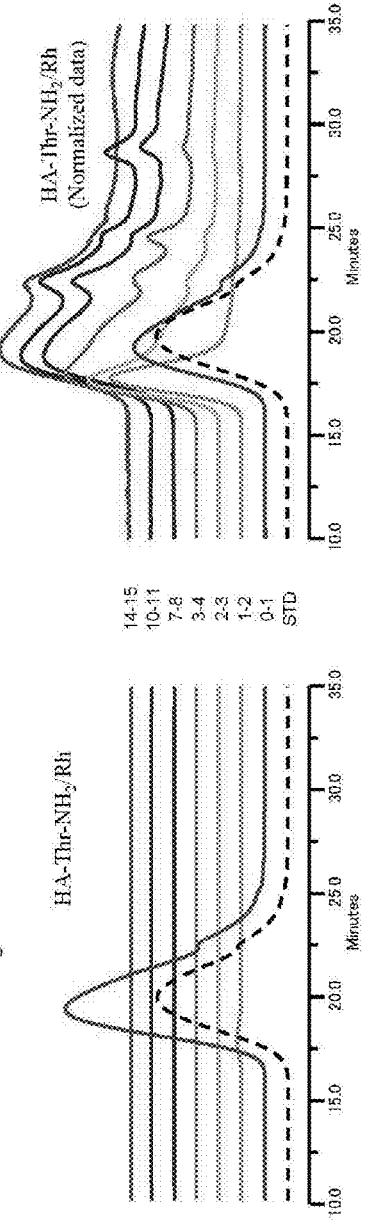
FIG. 10-29  Example 3-3-2 SEC chromatograms of rat urines
FIG. 10-30  Example 3-3-2 SEC chromatograms of rat urines

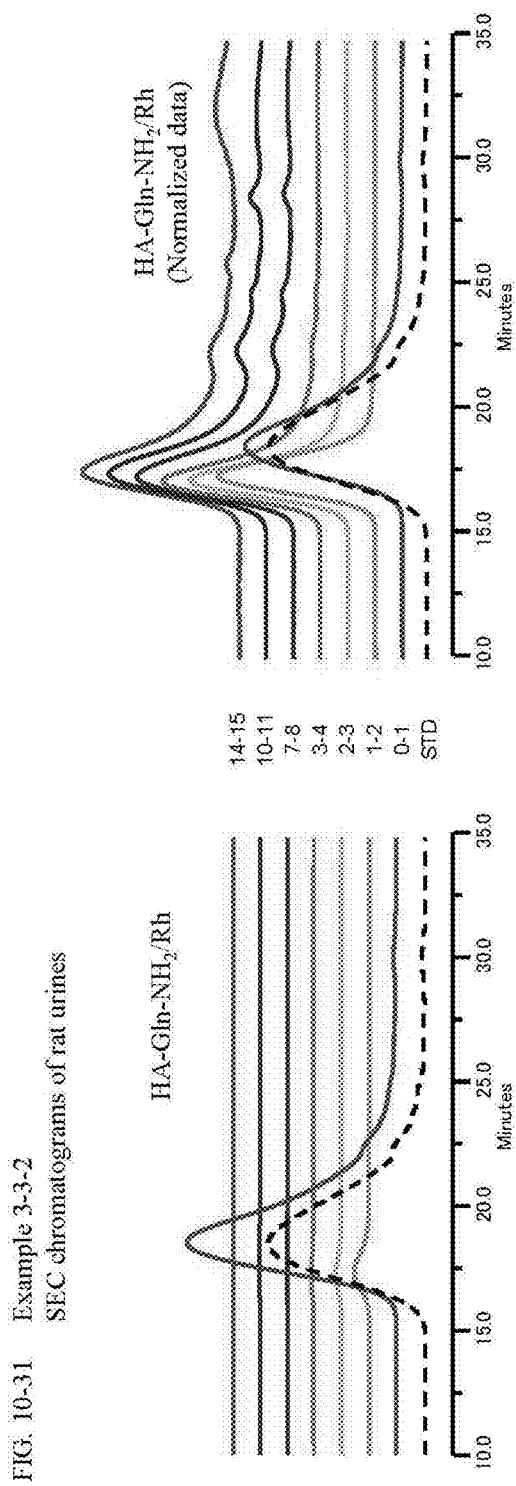
FIG. 10-31  Example 3-3-2
SEC chromatograms of rat urines

FIG. 11  Example 4-2
Liposome degradation degree

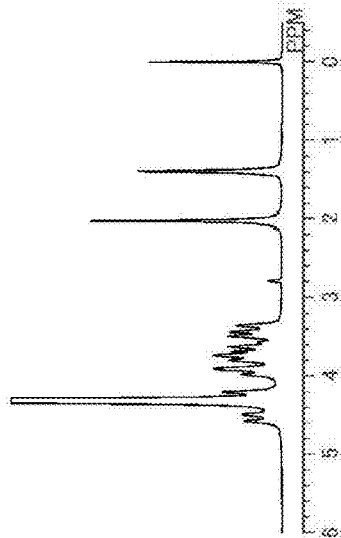
FIG. 12-2  Example 5-2
HA-Ala-EDOBEA
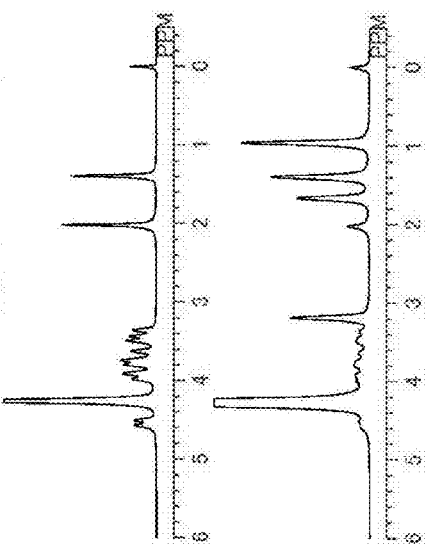
FIG. 12-1  Example 5-1
Samples for calculating modification degree
with alanine (upper), HA-Ala-TBA (lower)
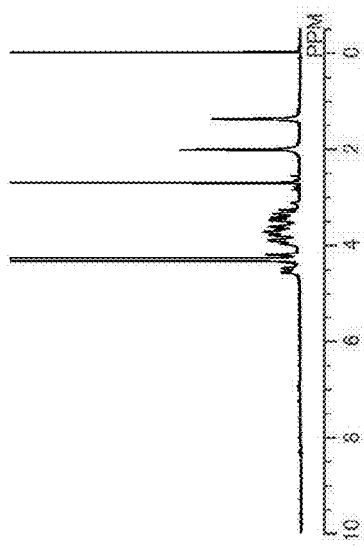
FIG. 12-3  Example 5-3
HA-Ala-EDOBEA-Rh

FIG. 13

Example 6-2-2
Transition of sample concentrations in rat plasma (group average, µg/mL)

| Example No. | 5-5 |
|---|---|
| Time after administration (h) | HA-Ala-PTH/Rh |
| 0.08333 | 212.16 |
| 2 | 170.83 |
| 7 | 149.00 |
| 24 | 92.52 |
| 48 | 64.64 |
| 72 | 48.14 |
| 168 | 8.23 |
| 240 | 3.22 |
| 312 | 1.91 |

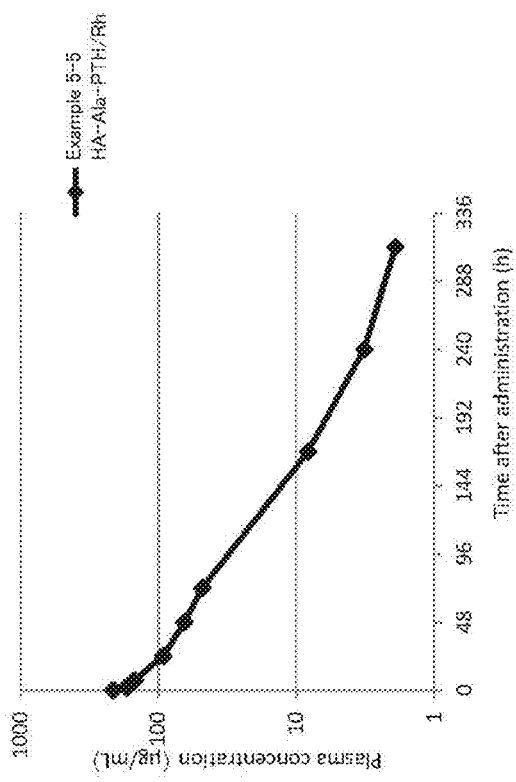
FIG. 14  Example 6-2-2
Time course of sample concentrations in rat plasma (chart)

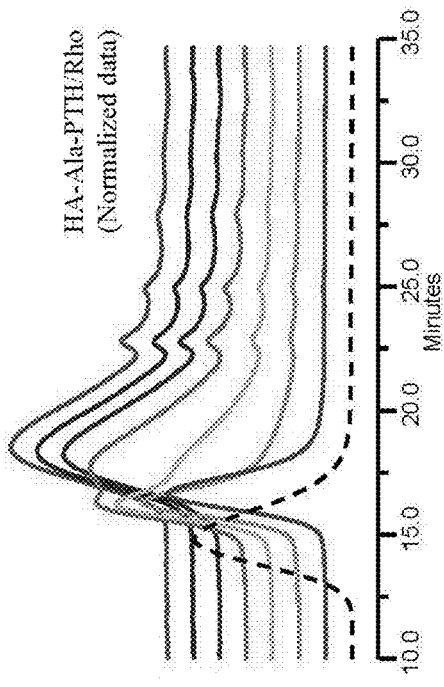
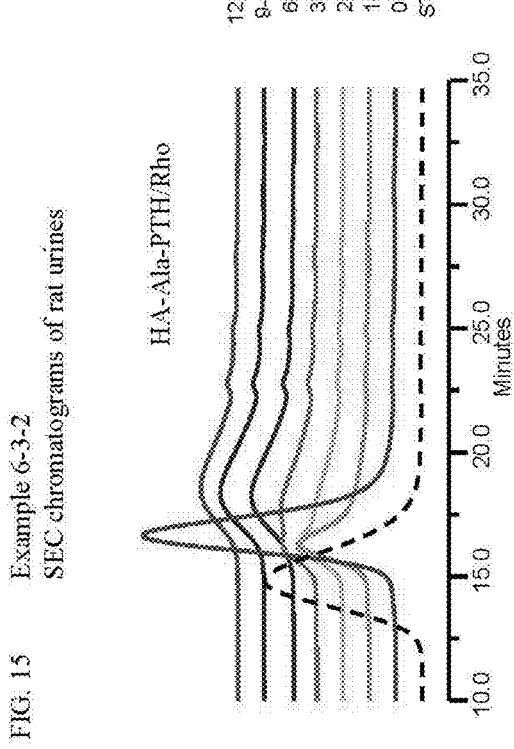
FIG. 15  Example 6-3-2
SEC chromatograms of rat urines

DERIVATIVE OF HYALURONIC ACID MODIFIED WITH AMINO-CARBOXYLIC ACID

TECHNICAL FIELD

The present invention relates to a derivative of hyaluronic acid modified with alkylamine, or with a compound having amino and carboxy (amino-carboxylic acid), such as amino acid, or with an amide compound thereof (amino-carboxylic acid amide), a conjugate between said hyaluronic acid derivative and a drug, as well as a pharmaceutical composition comprising said hyaluronic acid derivative, in particular, a complex between said hyaluronic acid derivative and a drug.

BACKGROUND ART

Polyethylene glycols (hereinafter also referred to as "PEG") are compounds that are inactive in the living body. It has been known that the stability and pharmacokinetic properties of proteins and liposomes in the living body can be improved by modifying them with PEG. Proteins modified with PEG and liposomes whose retentivity blood is increased by coating them with PEG have already entered the phase of commercialization pharmaceutical products. However, it has been reported that after long-term bolus injection of PEGylated proteins in animal trials, PEG accumulation in the kidney and kidney cavitation occurred. Particularly speaking, PEG is not a biodegradable polymer and has various problems yet to be clarified, including its accumulation and safety in the body after long-term injection to humans. Further, in recent years, some reports have appeared about the phenomenon causing PEG conjugates and PEGylated liposomes to be cleared unusually rapidly after their second dose (accerelated blood clearance phenomenon; hereinafter also referred to as "ABC phenomenon") (Non-Patent Documents 1 and 2); thus, it cannot be said that the safety and efficacy of PEGylated pharmaceutical products has been fully established.

In the meantime, there is a polymer that has already been used in clinical settings—hyaluronic acid. Hyaluronic acid (hereinafter also referred to as "HA") is a polysaccharide that was first isolated from the vitreous humour of the bovine eye by K. Meyer in 1934, and has long been known as a major component of the extracellular matrix. HA is a type of glycosaminoglycans composed of disaccharide repeating units of D-glucuronic acid and N-acetylglucosamine linked by $\beta$-(1→3) glycosidic bonds. HA has no species difference in its chemical or physical structure, and the HA metabolic system exists even in humans. Hyaluronic acid is also known as a very safe biomaterial from the viewpoint of immunity or toxicity.

In recent years, hyaluronic acid has attracted attention from the viewpoint of not only its safety, as mentioned above, but also the roles that it plays as a physiologically active substance in cell adhesion, cell growth, and induction of cell migration. As regards its production, the mass production of high-molecular-weight hyaluronic acid using microorganisms has been succeeded, and intensive research has been made on drug delivery systems (hereinafter also referred to as "DDS") using hyaluronic acid. There were other reports stating that conjugation of hyaluronic acid to a drug makes it possible to achieve targeting of the drug to cancer tissues (Patent Document 1), targeting of the drug to the liver (Patent Document 2), and reduction in antigenicity (Patent Document 3).

The drawback of hyaluronic acid when being used as a DDS substrate for targeting or extention in retension time is its poor retentivity in blood. Six consecutive saccharides are believed to be the site of hyaluronic acid that is recognized by the receptor, and various attempts have been made to elongate the retention time of HA in blood by modifying its carboxy groups (Patent Document 4, 5 and 6).

There was developed a hyaluronic acid derivative whose retentivity in blood was increased by highly modifying carboxy in the glucuronic acid moiety of hyaluronic acid, with its usefulness being demonstrated (Patent Document 7). In general, the retentivity of a hyaluronic acid derivative in blood is elongated by increasing the modification degree of carboxy in its glucuronic acid moiety. However, it has been found that both factors do not linearly correlate with each other but the correlation dramatically changes once the particular threshold is exceeded.

Oligonucleotides such as antisense DNA/RNA and siRNA, which have been being developed as nucleic acid pharmaceuticals in recent years, are subject to degradation by nucleases in and outside the living body, are rapidly degraded when they are intravenously (hereinafter also referred to as "iv") injected alone. In order for nucleic acid pharmaceuticals to display their efficacy, it is essential to deliver the nucleic acids into the cytoplasm or nucleus. A majority of conventional pharmaceutical products comprising proteins or peptides as an active ingredient act on extracellular targets. In order to develop more innovative pharmaceutical products, a means to allow proteins or peptides to act on intracellular targets is needed. For this purpose, there is a need to develop a process for delivering proteins or peptides into the cytoplasm, more specifically a process by which after a medicament is taken up by the cell via endocytosis, the active ingredient of the medicament is effectively released from the endosome into the cytoplasm.

Synthetic canonic polymers make it possible to electrostatically condense the negatively charged gene and deliver the gene into the cytoplasm and, thus, have been considered as effective as a gene carrier. The synthetic cationic polymers that have been reported include poly-L-lysine (Patent Document 8, Non-Patent Document 3), polyethyleneimine (Non-Patent Document 4), a synthetic polymer having an imidazolyl group (Non-Patent Document 5), and a polyamidoamine dendrimer (Non-Patent Document 6). In particular, it has been shown that the polyethyleneimine having secondary amine and the synthetic polymer having an imidazolyl group are taken up into the cytoplasm with high transfer efficiency due to their proton sponge effect. However, these synthetic polymers are polyamines that are generally believed to have high cytotoxicity, and are not completely ensured to be safe. There was another example of using chitosan, a cationic polysaccharide polymer (Non-Patent Document 7), but this technique has not yet been put to practical use because of its low gene transfer efficiency. Still another report was made on an attempt for intracytoplasmic transfer of siRNA using a nanogel that is obtained by modifying carboxy in hyaluronic acid with a compound having a mercapto group (thiol) and ultrasonically crosslinking the modified HA (Non-Patent Document 17).

There were also various reports about intracytoplasmic transfer of proteins/peptides. Examples include the reports on attempts for intracytoplasmic transfer through the modification of a peptide with a cell-penetrating peptide (cpp) (Non-Patent Document 8) or through the formation of a protein/peptide complex comprising a cationic libosome as a carrier (Non-Patent Document 9), but the transfer efficiencies of these techniques were not necessarily high.

Further, in order to reduce cytotoxicity, various approaches were attempted, including PEGylation of a polyamine or modification of HA with a polyamine (Non-Patent Document 10), and modification of a polyamine with a functional group that detaches in a pH-responsive fashion (e.g., at low pH). However, polyamines are inherently used even in these approaches, so further work and studies are needed on the toxicity of these components (Non-Patent Document 11).

Weakly anionic polycarboxylic acid polymers have also been studied. Said polymers exhibit water solubility under physiological conditions (pH 7.4) but show hydrophobicity in a weakly acidic range (pH 5-6.8) which corresponds to the pH in the endosome, and thus disrupt the endosomal membrane, thereby enabling release of a gene/drug from the endosome into the cytoplasm. Those known anionic polyerms include poly(ethyl acrylic acid) (Non-Patent Document 12) and poly (propyl acrylic acid) (Non-Patent Document 13), and it was shown that a polycarboxylic acid polymer having pKa of about 5 is less cytotoxic and effective for release of a nucleic acid from the endosome. Other reports stated that succinylated polyglycidol (Non-Patent Document 14), and pseudopeptides prepared by modifying the side chains of poly(L-lysine iso-phthalamide) with L-phenylalanine (Non-Patent Document 15) are effective as pH-responsive anionic polymers in release of genes/drugs from the endosome, more specifically uptake of endocytosed drugs into the cytoplasm.

Examples of the modifications of carboxy in hyaluronic acid with amino acids include modification with a glycine ethyl ester using, as a condensing agent, 4-(4,6-dimethoxy-1,3,5-triazine)-4-methylmorpholinium (hereinafter also referred to as DMT-MM) formed with 2-chloro-4,6-dimethoxy-1,3,5-triazine in the presence of N-methylmorpholine, but the degree of this modification was 20% at the maximum (Non-Patent Document 16). Examples of the modifications using triazine compounds as a condensing agent, which were reported in the documents disclosed after the priority date of the present application, include alanine introduced hyaluronic acid (Non-Patent Document 18); and modifications with other amino acids by the same procedures were also reported (Non-Patent Document 19, Patent Document 10). There was yet another report stating that hyaluronic acid was modified with leucine methyl ester hydrochloride, valine methyl ester hydrochloride, isoleucine methyl ester hydrochloride, proline methyl ester hydrochloride, phenylalanine methyl ester hydrochloride, arginine methyl ester hydrochloride, or histidine methyl ester hydrochloride using 1-ethyl-3-(3-dimethylaminopropyl)carbodiimide hydrochloride (hereinafter also referred to as EDC) as a condensing agent, and the resulting product was gelated without being deprotected, whereby a water-insoluble biocompatible film was prepared, but the degree of this modification was unknown (Patent Document 9).

As for modification of hyaluronic acid by amidation of carboxyl groups in hyaluronic acid with an aliphatic amine or an arylaliphatic amine, there were reported examples where benzylamine, octylamine, dodecylamine, and hexadecylamine were introduced using 1,1-carbonyldiimidazole in yields of 60%, 25%, 15% and 5%, respectively, but the degrees of these modifications were 60% at the maximum (Patent Document 11).

CITATION LIST

Patent Documents

Patent Document 1: International Patent Publication No. WO 92/06714
Patent Document 2: Japanese Unexamined Patent Application Publication No. JP 2001-81103
Patent Document 3: Japanese Unexamined Patent Application Publication No. JP H02-273176
Patent Document 4: Japanese Unexamined Patent Application Publication No. JP H05-85942
Patent Document 5: International Patent Publication No. WO 01/05434
Patent Document 6: International Patent Publication No. WO 01/60412.
Patent Document 7: International Patent Publication No. WO 2006/028110
Patent Document 8: International Patent Publication No. WO 1999/029839
Patent Document 9: International Patent Publication No. WO 92/20349
Patent Document 10: International Patent Publication No. WO 2011/148116
Patent Document 11: International Patent Publication No. WO 2000/01733

Non-Patent Documents

Non-Patent Document 1: *Int. J. Pharm.*, Vol. 255, p. 167-17.4, 2003
Non-Patent Document 2: *J. Control. Rel.*, Vol. 88, p. 35-42, 2003
Non-Patent Document 3: *J. Biol. Chem.*, Vol. 262, p. 4429-4432, 1987
Non-Patent Document 4: *J. Control. Rel.*, Vol. 60, p. 149-160, 1999
Non-Patent Document 5: *Bioconjugate Chem.*, Vol. 10, p. 406-411, 1999
Non-Patent Document 6: *Bioconjugate Chem.*, Vol. 4, p. 372-379, 1993
Non-Patent Document 7: *J. Control. Rel.*, Vol. 56, p. 259-272, 1998
Non-Patent Document 8: *J. Biol. Chem.*, Vol. 272, p. 16010-16017, 1997
Non-Patent Document 9: *J. Biol. Chem.*, Vol. 276, p. 35103-35110, 2001
Non-Patent Document 10: *Biopolymers*, Vol. 89, p. 635-642, 2008
Non-Patent Document 11: *Bioconjugate Chem.*, Vol. 14, p. 51-57, 2003
Non-Patent Document 12: *Acc. Chem. Res.*, Vol. 25, p. 336-342, 1992
Non-Patent Document 13: *J. Control. Rel.*, Vol. 61, p. 137-143, 1999
Non-Patent Document 14: *Bioconjugate Chem.*, Vol. 19, p. 1040-1048, 2008
Non-Patent Document 15: *Biomaterials*, Vol. 30, p, 1954-1961, 2009
Non-Patent Document 16: *Biomacromolecules*, Vol. 8, p. 2190-2195, 2007
Non-Patent Document 17: *J. Control. Rel.*, Vol. 119, p, 245-252, 2007
Non-Patent Document 18: *CARBOHYDRATE Polymers*, Vol. 86, p. 747-752, 2011
Non-Patent Document 19: *CARBOHYDRATE Polymers*, Vol. 87, p. 2211-2216, 2012

SUMMARY OF INVENTION

Technical Problem

It has been found that the retentivity in blood of a hyaluronic acid derivative correlates with the modification degree of carboxy in its glucuronic acid moiety, and also that the correlation dramatically changes once the particular threshold is exceeded; so it is difficult to control the retentivity in blood of a hyaluronic acid derivative within a desirable range merely by controlling the degree of carboxy modification. Accordingly, there has been a need for a process for controlling retentivity in blood in a simpler and more reliable way. It is also presumed that as hyaluronic acid becomes less recognizable by a receptor, it is less susceptible to metabolism in the living body and its intrinsic biodegradability is harder to exhibit. Therefore, there has been needed a novel substrate that is characterized by both biodegradability (safety) and retentivity in blood.

Though various materials have been reported which can be used for delivery of an endocytosed medicinal active ingredient into the cytoplasm, there has also been needed a process for delivering an active ingredient more effectively and/or more safely.

A problem to be solved by the present invention is to provide a hyaluronic acid derivative Characterized by both biodegradability and retentivity in blood, and/or a hyaluronic acid derivative that can deliver a gene or a drug into the cytoplasm. Another problem to be solved by the present invention is to provide a conjugate between the hyaluronic acid derivative and a drug, and a pharmaceutical composition comprising the hyaluronic acid derivative, in particular, a complex between the hyaluronic acid derivative and the drug.

Solution to Problem

The present inventors have intensive studies to solve the above-noted problems and, as a result, have found that a hyaluronic acid derivative, which is obtained by amidating carboxy in the glucuronic acid moiety of hyaluronic acid or a salt thereof through its reaction with a particular alkylamine, a particular amino-carboxylic acid or a particular amino-carboxylic acid amide, is characterized by biodegradability and retentivity in blood. Thus, the inventors have completed the present invention. The inventors have also found that a derivative of hyaluronic acid modified with a particular amino-carboxylic acid is effective for release of a gene/drug from the endosome into the cytoplasm and, thus, the inventors have completed the invention.

More specifically, the present invention is directed to a hyaluronic acid derivative characterized by both biodegradability and retentivity in blood, and a hyaluronic acid derivative that makes it possible to prevent degradation of a compound having a pharmacological activity, in particular a nucleic acid drug, within the living body and to deliver the compound into the cytoplasm. Further, this invention is directed to a process for preparing the hyaluronic acid derivative, as well as a pharmaceutical composition comprising a drug and the hyaluronic acid derivative, and a process for preparing said composition.

In one aspect of the present invention, the hyaluronic acid derivatives as recited below in (1) to (17) are provided.

(1) A hyaluronic acid derivative comprising disaccharide units each represented by Formula (I):

[Formula 1]

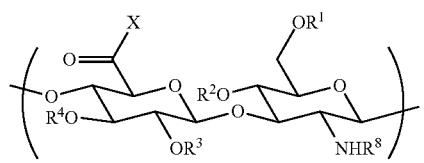

(I)

[wherein
$R^1$, $R^2$, $R^3$, and $R^4$ are each independently selected from a hydrogen atom, $C_{1-6}$ alkyl, formyl and $C_{1-6}$ alkylcarbonyl;
$R^8$ is a hydrogen atom, formyl or $C_{1-6}$ alkylcarbonyl;

X is a group represented by $—NR^x-A-B—Z$;
A is selected from and $—CR^aR^b—$ and $C_{3-8}$ cycloalkylene, B is a direct bond, and Z is $—COOR^y$ or $—CONR^{ya}R^{yb}$; or -A-B—Z represents $C_{1-6}$ alkyl; or
A is $—CH_2—$ or $—CH_2—CH_2—$, B is selected from phenylene (wherein the phenylene may be substituted by one or more groups selected from hydroxy and halogen atoms), $C_{3-8}$ cycloalkylene and phenylmethane-1,1-diyl, and Z is $—COOR^y$;
$R^x$ and $R^y$ are each independently selected from a hydrogen atom and $C_{1-6}$ alkyl;
$R^a$ is selected from a hydrogen atom and $C_{1-6}$ alkyl;
$R^b$ is selected from a hydrogen atom, $C_{1-6}$ alkyl (wherein the $C_{1-6}$ alkyl may be substituted by one or more groups selected from hydroxy, carboxy, $C_{3-8}$ cycloalkyl, aryl and carbamoyl, wherein the aryl may be substituted by hydroxy), $C_{3-8}$ cycloalkyl, and aryl (wherein the aryl may be substituted by hydroxy);
$R^{ya}$ and $R^{yb}$ are each independently sleeted from a hydrogen atom, $C_{1-6}$ alkyl, formyl and $C_{1-6}$ alkylcarbonyl],
wherein, when A in Formula (I) is $—CR^aR^b—$ or $C_{3-8}$ cycloalkylene, the proportion of the disaccharide units of Formula (I) with respect to disaccharide units present is at least 70%.

(2) The hyaluronic acid derivative as recited in (1), wherein X is $—NHCH_3$, $—NH(CH_2)_2CH_3$, or $—NR^x-A-Z$; and A is $—CR^aR^b—$ or $C_{3-8}$ cycloalkylene.

(3) The hyaluronic acid derivative as recited in (1), wherein A is $C_{3-8}$ cycloalkylene, and B is a direct bond;
A is $—CH_2—$ or $—CH_2—CH_2—$, and B is selected from phenylene (wherein the phenylene may be substituted by one or more groups selected from hydroxy and halogen atoms), $C_{3-8}$ cycloalkylene and phenylmethane-1,1-diyl; or
A is selected from 2-cyclohexylethane-1,1-diyl, 2-(2-naphthyl)ethane-1,1-diyl, 3-phenylpropane-1,1-diyl, cyclohexylmethane-1,1-diyl and 4-hydroxyphenylmethane-1,1-diyl, and B is a direct bond.

(4) The hyaluronic acid derivative as recited in (1) or (3), wherein
A is $—CH_2—$, and B is selected from cyclohexane-1,1-diyl, benzene-1,4-diyl, benzene-1,3-diyl, 2-chlorobenzene-1,4-diyl and phenylmethane-1,1-diyl;
A is $—CH_2CH_2—$, and B is benzene-1,4-diyl; or
A is selected from 2-cyclohexylethane-1,1-diyl, 2-(2-naphthyl)ethane-1,1-diyl and 3-phenylpropane-1,1-diyl; and B is a direct bond.

(5) The hyaluronic acid derivative as recited in any one of (1) to (4), wherein 7 is $—COOR^y$.

(6) A hyaluronic acid derivative comprising disaccharide units represented by Formula (I):

[Formula 2]

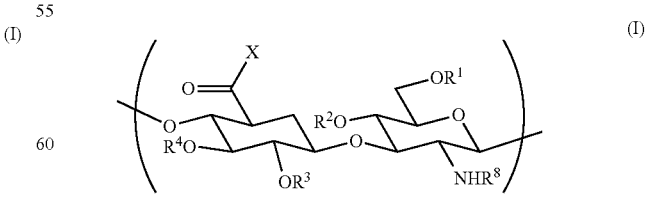

(I)

[wherein
$R^1$, $R^2$, $R^3$, and $R^4$ are each independently selected from a hydrogen atom, $C_{1-6}$ alkyl, formyl and $C_{1-6}$ alkylcarbonyl;
$R^8$ is a hydrogen atom, formyl or $C_{1-6}$ alkylcarbonyl;

X is a group represented by —NHCH$_3$, —NH(CH$_2$)$_2$CH$_3$, —NR$^x$-A-B—COOR$^y$ or —NR$^x$—CHR$^c$—CONR$^{ya}$R$^{yb}$;

R$^x$ and R$^y$ are each independently selected from a hydrogen atom and C$_{1-6}$ alkyl;

A is selected from —CR$^a$R$^b$—, C$_{3-8}$ cycloalkylene, 2-cyclohexylethane-1,1-diyl, 2-(2-naphthyl)ethane-1,1-diyl, 3-phenylpropane-1,1-diyl, cyclohexylmethane-1,1-diyl and 4-hydroxyphenylmethane-1,1-diyl, and B is a direct bond; or A is —CH$_2$— or —CH$_2$—CH$_2$—, and B is selected from phenylene (wherein the phenylene may be substituted by one or more groups selected from hydroxy and halogen atoms), C$_{3-8}$ cycloalkylene and phenylmethane-1,1-diyl;

R$^a$ is selected from a hydrogen atom and C$_{1-6}$ alkyl;

R$^b$ is selected from a hydrogen atom and C$_{1-6}$ alkyl (wherein the C$_{1-6}$ alkyl may be substituted by one or more groups selected from hydroxy, carboxy and carbamoyl);

R$^c$ represents C$_{1-6}$ alkyl which may be substituted by carbamoyl;

R$^{ya}$ and R$^{yb}$ are each independently selected from a hydrogen atom, C$_{1-6}$ alkyl, formyl and C$_{1-6}$ alkylcarbonyl]

wherein, when A in Formula (I) is —CR$^a$R$^b$— or C$_{3-8}$ cycloalkylene, the proportion of the disaccharide units of Formula (I) with respect to disaccharide units present is at least 70%.

(7) The hyaluronic acid derivative as recited in (6), wherein X is —NHCH$_3$, —NH(CH$_2$)$_2$CH$_3$ or —NR$^x$—CHR$^c$—CONR$^{ya}$R$^{yb}$, or A is —CR$^a$R$^b$— or C$_{3-8}$ cycloalkylene.

(8) The hyaluronic acid derivative as recited in (6), wherein
A is C$_{3-8}$ cycloalkylene, and B is a direct bond;
A is —CH$_2$— or —CH$_2$—CH$_2$—, and B is selected from phenylene (wherein the phenylene may be substituted by one or more groups selected from hydroxy and halogen atoms), C$_{3-8}$ cycloalkylene and phenylmethane-1,1-diyl; or
A is selected from 2-cyclohexylethane-1,1-diyl, 2-(2-naphthyl)ethane-1,1-diyl, 3-phenylpropane-1,1-diyl, cyclohexylmethane-1,1-diyl and 4-hydroxyphenylmethane-1,1-diyl, and B is a direct bond.

(9) The hyaluronic acid derivative as recited in (6) or (8), wherein
A is —CH$_2$—, and B is selected from cyclohexane-1,1-diyl, benzene-1,4-diyl, benzene-1,3-diyl, 2-chlorobenzene-1,4-diyl and phenylmethane-1,1-diyl;
A is —CH$_2$CH$_2$—, and B is benzene-1,4-diyl; or
A is selected from 2-cyclohexylethane-1,1-diyl, 2-(2-naphthyl)ethane-1,1-diyl and 3-phenylpropane-1,1-diyl; and B is a direct bond.

(10) A hyaluronic acid derivative comprising disaccharide units represented by Formula (I):

[Formula 3]

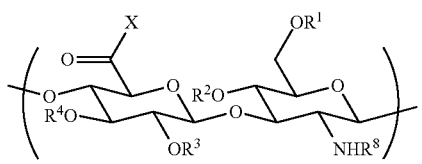

(I)

[wherein
R$^1$, R$^2$, R$^3$, and R$^4$ are each independently selected from a hydrogen atom, C$_{1-6}$ alkyl, formyl and C$_{1-6}$ alkylcarbonyl;
R$^8$ is a hydrogen atom, formyl or C$_{1-6}$ alkylcarbonyl;
X is a group represented by —NR$^x$-A-B—COOR$^y$;
R$^x$ and R$^y$ are each independently selected from a hydrogen atom and C$_{1-6}$ alkyl;

A is selected from —CR$^a$R$^b$—, C$_{3-8}$ cycloalkylene, 2-cyclohexylethane-1,1-diyl, 2-(2-naphthyl)ethane-1,1-diyl, and 3-phenylpropane-1,1-diyl, and B is a direct bond; or A is —CH$_2$—, and B is selected from phenylene and C$_{3-8}$ cycloalkylene; —R$^a$ is selected from a hydrogen atom and C$_{1-6}$ alkyl;

R$^b$ is selected from a hydrogen atom and C$_{1-6}$ alkyl (wherein the C$_{1-6}$ alkyl may be substituted by one or more groups selected from hydroxyl and carboxy)], wherein, when A in Formula (I) is —CR$^a$R$^b$— or C$_{3-8}$ cycloalkylene, the proportion of the disaccharide units of Formula (I) with respect to disaccharide units present is at least 70%.

(11) The hyaluronic acid derivative as recited in (10), wherein A is —CR$^a$R$^b$— or C$_{3-8}$ cycloalkylene

(12) The hyaluronic acid derivative as recited in (10), wherein
A is C$_{3-8}$ cycloalkylene, and B is a direct bond;
A is —CH$_2$—, and B is selected from phenylene and C$_{3-8}$ cycloalkylene; or
A is selected from 2-cyclohexylethane-1,1-diyl, 2-(2-naphthyl)ethane-1,1-diyl and 3-phenylpropane-1,1-diyl, and B is a direct bond.

(13) The hyaluronic acid derivative as recited in (10) or (12), wherein
A is —CH$_2$—, and B is selected from cyclohexane-1,1-diyl and benzene-1,4-diyl; or
A is selected from 2-cyclohexylethane-1,1-diyl, 2-(2-naphthyl)ethane-1,1-diyl and 3-phenylpropane-1,1-diyl, and B is a direct bond.

(14) The hyaluronic acid derivative as recited in any one of (1) to (13), further comprising disaccharide units represented by Formula (II):

[Formula 4]

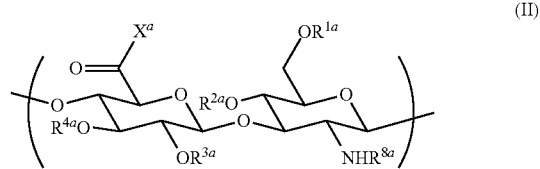

(II)

[wherein
R$^{1a}$, R$^{2a}$, R$^{3a}$, and R$^{4a}$ are each independently selected from a hydrogen atom, C$_{1-6}$ alkyl, formyl and C$_{1-6}$ alkylcarbonyl;
R$^{8a}$ is a hydrogen atom, formyl or C$_{1-6}$ alkylcarbonyl;
X$^a$ is selected from hydroxy and —O$^-$Q$^+$, wherein Q$^+$ represents a countercation].

(15) The hyaluronic acid derivative as recited in any one of (1) to (14), further comprising disaccharide units represented by Formula (III):

[Formula 5]

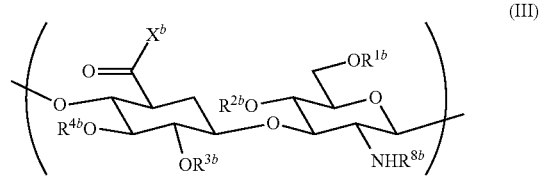

(III)

[wherein $R^{1b}$, $R^{2b}$, $R^{3b}$, and $R^{4b}$ are each independently selected from a hydrogen atom, $C_{1-6}$ alkyl, formyl and $C_{1-6}$ alkylcarbonyl;

$R^{8b}$ is a hydrogen atom, formyl or $C_{1-6}$ alkylcarbonyl;

$X^b$ is a group represented by $-NR^e-Y^{yb}-R^d$; wherein $R^e$ is a hydrogen atom or $C_{1-6}$ alkyl;

$R^d$ is a hydrogen atom, $C_{1-6}$ alkyl, $-CO-C(R^7)=CH_2$, or $-CO-G^4-X^c$;

$R^7$ is a hydrogen atom or methyl;

$G^4$ is selected from phenylene, $C_{3-8}$ cycloalkylene, and $-G^5-(C_{1-10}$ alkylene$)-G^6-$, wherein the $C_{1-10}$ alkylene moiety may have one to three phenylenes or $C_{3-8}$ cycloalkylenes inserted therein;

$G^5$ and $G^6$ are each independently selected from a direct bond, phenylene, and $C_{3-8}$ cycloalkylene;

$X^c$ is mercapto, a halogen atom or a group represented by

[Formula 6]

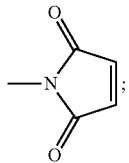

$Y^b$ is $-CH_2-(CHR^5)_{l-2}-CH_2-NH-$, $-CH_2-(CHR^6)_{p-2}-CH_2-O-$, $-(CH_2)_j-S-$, or $-(CH_2)_a-(Y^1-(CH_2)_b)_c-G-$;

l, p, and j are each independently an integer selected from 2 to 10, and $R^5$ and $R^6$ are each independently a hydrogen atom or hydroxy;

a is an integer selected from 2 to 10;

each b is independently an integer selected from 2 to 10;

c is an integer selected from 1 to 200;

$Y^1$ is an oxygen atom or $-NR^n-$;

G is an oxygen atom, a sulfur atom or $-NH-$;

$R^n$ is a hydrogen atom, $C_{1-6}$ alkyl, $-CO-(CH_2)_d-R^o$, $-(CH_2)_e-R^p$, or $-(CH_2)_f-(Y^2-(CH_2)_g)_h-R^q$;

each g is independently an integer selected from 2 to 10;

d, e, f and h are each independently an integer selected from 2 to 10;

$R^o$, $R^p$ and $R^q$ are each independently a hydrogen atom, hydroxy, carboxy or $-NHR^r$;

$Y^2$ is an oxygen atom or $-NH-$;

$R^r$ is a hydrogen atom, formyl or $C_{1-6}$ alkylcarbonyl].

(16) The hyaluronic acid derivative as recited in any one of (1) to (15), which is prepared using hyaluronic acid composed exclusively of the disaccharide units each represented by Formula (II) as recited in (14), wherein, when $R^{1a}$, $R^{2a}$, $R^{3a}$, and $R^{4a}$ are all hydrogen atoms, $R^{8a}$ is acetyl, and $X^a$ is $-O^-Na^+$, the weight-average molecular weight is in the range of 20-120 kilodaltons.

(17) The hyaluronic acid derivative as recited in any one of (1) to (15), wherein an underivatized hyaluronic acid corresponding to the hyaluronic acid derivative in terms of backbone structure has a weight-average molecular weight of 20-120 kilodaltons, wherein the underivatized hyaluronic acid is hyaluronic acid composed exclusively of disaccharide units of Formula (II) wherein $R^{1a}$, $R^{2a}$, $R^{3a}$ and $R^{4a}$ are hydrogen atoms, $R^{8a}$ is acetyl, and $X^a$ is $-O^-Na^+$.

In another aspect of the present invention, provided is a pharmaceutical composition comprising the hyaluronic acid derivative as recited in any one of (1) to (17) as a carrier.

In yet another aspect of the present invention, provided is a hyaluronic acid derivative/drug conjugate wherein one or more drugs are conjugated to the hyaluronic acid derivative as recited in any one of (1) to (17).

In still another aspect of the present invention, provided is a biodegradable drug carrier comprising the hyaluronic acid derivative as recited in any one of (1) to (17).

In yet another aspect of the present invention, provided is a carrier for intracytoplasmic transfer of a drug, comprising the hyaluronic acid derivative as recited in any one of (1) to (17).

Further, in another aspect of the present invention, provided is a biodegradable drug carrier comprising the hyaluronic acid derivative as recited in any one of (1), (2), (5) to (7), (10), (11), and (14) to (17).

In yet another aspect of the present invention, provided is a carrier for intracytoplasmic transfer of a drug, comprising the hyaluronic acid derivative as recited in any one of (1), (3) to (6), (8) to (10), and (12) to (17)

Further, in another aspect of the present invention, provided is a method for administrating a drug, comprising administering to a subject a therapeutically effective amount of a drug together with the hyaluronic acid derivative as recited in any one of (1) to (17).

In yet another aspect of the present invention, provided is a method or intracytoplasmic transfer of a drug, comprising administering a therapeutically effective amount of a drug together with the hyaluronic acid derivative as recited in any one of (1) to (17).

Further, in another aspect of the present invention, provided is a method for administrating a drug, comprising administering to a subject a therapeutically effective amount of a drug together with the hyaluronic acid derivative as recited in any one of (1), (2), (5) to (7), (10), (11), and (14) to (17).

In yet another aspect of the present invention, provided is a process for intracytoplasmic transfer of a drug, comprising administering a therapeutically effective amount of a drug together with the hyaluronic acid derivative as recited in any one of (1), (3) to (6), (8) to (10), and (12) to (17).

BRIEF DESCRIPTION OF DRAWINGS

FIG. 1 shows an example of the $^1$H-NMR spectrum of HA-TBA prepared in Example 1-2.

FIG. 2 shows an example of the $^1$H-NMR spectrum of HA-FL/TBA prepared in Example 1-3.

FIG. 3-1 shows an example of the $^1$H-NMR spectrum of HA-Ala/FL prepared in Example 1-4-1.

FIG. 3-2 shows examples of the $^1$H-NMR spectra of HA-Ser/FL and HA-Ser-OEt/FL prepared in Example 1-4-2.

FIG. 3-3 shows an example of the $^1$H-NMR spectrum of HA-Glu/FL prepared in Example 1-4-3.

FIG. 3-4 shows examples of the $^1$H-NMR spectra of HA-Gly/FL and HA-Gly-OEt/FL prepared in Example 1-4-4.

FIG. 3-5 shows an example of the $^1$H-NMR spectrum of HA-Val/FL prepared in Example 1-4-5.

FIG. 3-6 shows an example of the $^1$H-NMR spectrum of HA-Leu/FL prepared in Example 1-4-6.

FIG. 3-7 shows an example of the $^1$H-NMR spectrum of HA-Ile/FL prepared in Example 1-4-7.

FIG. 3-8 shows an example of the $^1$H-NMR spectrum of HA-Thr/FL prepared in Example 1-4-8.

FIG. 3-9 shows an example of the $^1$H-NMR spectrum of HA-Asp/FL prepared in Example 1-4-9.

FIG. 3-10 shows an example of the $^1$H-NMR spectrum of HA-cACHCA/FL prepared in Example 1-4-10.

FIG. 3-11 shows an example of the $^1$H-NMR spectrum of HA-tACHCA-OEt/FL prepared in Example 1-4-11.

FIG. 3-12 shows an example of the $^1$H-NMR spectrum of HA-Aib/FL prepared in Example 1-4-12.

FIG. 3-13 shows an example of the $^1$H-NMR spectrum of HA-ACBuCA-OEt/FL prepared in Example 1-4-13.

FIG. 3-14 shows an example of the $^1$H-NMR spectrum of HA-Asn/Rh prepared in Example 1-4-14.

FIG. 3-15 shows an example of the $^1$H-NMR spectrum of HA-Ala-NH$_2$/Rh prepared in Example 1-4-15.

FIG. 3-16 shows an example of the $^1$H-NMR spectrum of HA-Val-NH$_2$/Rh prepared in Example 1-4-16.

FIG. 3-17 shows an example of the $^1$H-NMR spectrum of HA-Asn-NH$_2$/Rh prepared in Example 1-4-17.

FIG. 3-18 shows examples of the $^1$H-NMR spectra of HA-Me and HA-Me/FL prepared in Example 1-4-18.

FIG. 3-19 shows examples of the $^1$H-NMR spectra of HA-Pr and HA-Pr/FL prepared in Example 1-4-19.

FIG. 4-1 shows an example of the $^1$H-NMR spectrum of HA-AMCHCA prepared in Example 1-5-1.

FIG. 4-2 shows an example of the $^1$H-NMR spectrum of HA-pcACHCA prepared in Example 1-5-2.

FIG. 4-3 shows an example of the $^1$H-NMR spectrum of HA-Nal prepared in Example 1-5-3.

FIG. 4-4 shows an example of the $^1$H-NMR spectrum of HA-APBA prepared in Example 1-5-4.

FIG. 4-5 shows an example of the $^1$H-NMR spectrum of HA-Cha prepared in Example 1-5-5.

FIG. 4-6 shows an example of the $^1$H-NMR spectrum of HA-AMBA prepared in Example 1-5-6.

FIG. 4-7 shows an example of the $^1$H-NMR spectrum of HA-3AMBA prepared in Example 1-5-7.

FIG. 4-8 shows an example of the $^1$H-NMR spectrum of HA-APhPA prepared in Example 1-5-8.

FIG. 4-9 shows an example of the $^1$H-NMR spectrum of HA-AEBA prepared in Example 1-5-9.

FIG. 4-10 shows an example of the $^1$H-NMR spectrum of HA-AMClBA prepared in Example 1-5-10.

FIG. 4-11 shows an example of the $^1$H-NMR spectrum of HA-AMSA prepared in Example 1-5-11.

FIG. 4-12 shows an example of the $^1$H-NMR spectrum of HA-4AMCHCA prepared in Example 1-5-12.

FIG. 4-13 shows an example of the $^1$H-NMR spectrum of HA-Chg prepared in Example 1-5-13.

FIG. 4-14 shows an example of the $^1$H-NMR spectrum of HA-pHPhg prepared in Example 1-5-14.

FIG. 5-1 shows examples of the $^1$H-NMR spectra of HA-FL, and HA-EDOBEA with low modification degree, which were prepared in Comparative Example 1-1-1.

FIG. 5-2 shows examples of the $^1$H-NMR spectra of HA-EDOBEA-Ac/FL and HA-EDOBEA with high modification degree, which were prepared in Comparative Example 1-1-2.

FIG. 5-3 shows an example of the $^1$H-NMR spectrum of HA-Phe/FL prepared in Comparative Example 1-1-3.

FIG. 5-4 shows an example of the $^1$H-NMR spectrum of HA-Tyr/FL prepared in Comparative Example 1-1-4.

FIG. 5-5 shows an example of the $^1$H-NMR spectrum of HA-MePhe/FL prepared in Comparative Example 1-1-5.

FIG. 5-6 shows an example of the $^1$H-NMR spectrum of HA-Pro-OMe/FL prepared in Comparative Example 1-1-6.

FIG. 5-7 shows an example of the $^1$H-NMR spectrum of HA-Gly NH$_2$/Rh prepared in Comparative Example 1-1-7.

FIG. 5-8 shows an example of the $^1$H-NMR spectrum of HA-Ser-NH$_2$/Rh prepared in Comparative Example 1-1-8.

FIG. 5-9 shows an example of the $^1$H-NMR spectrum of HA-Leu-NH$_2$/Rh prepared in Comparative Example 1-1-9.

FIG. 5-10 shows an example of the $^1$H-NMR spectrum of HA-Ile-NH$_2$/Rh prepared in Comparative Example 1-1-10.

FIG. 5-11 shows an example of the $^1$H-NMR spectrum of HA-Thr-NH$_2$/Rh prepared in Comparative Example 1-1-11.

FIG. 5-12 shows an example of the $^1$H-NMR spectrum of HA-Gln-NH$_2$/Rh prepared in Comparative Example 1-1-12.

FIG. 6-1 shows an example of the $^1$H-NMR spectrum of HA-Nle prepared in Comparative Example 1-2-1.

FIG. 6-2 shows an example of the $^1$H-NMR spectrum of HA-tLeu prepared in Comparative Example 1-2-2.

FIG. 6-3 shows an example of the $^1$H-NMR spectrum of HA-pFPhe prepared in Comparative Example 1-2-3.

FIG. 6-4 shows an example of the $^1$H-NMR spectrum of HA-Phg prepared in Comparative Example 1-2-4.

FIG. 7 shows an example of the $^1$H-NMR spectrum of PEG-FL prepared in Comparative Example 1-3.

FIG. 8 shows the group averages for the time courses of sample concentrations in rat plasma as calculated in Example 3-2-2.

FIG. 9-1 shows the charts that plot the group averages for the time courses of sample concentrations in rat plasma as calculated in Example 3-2-2.

FIG. 9-2 shows the charts that plot the group averages for the time courses of sample concentrations in rat plasma as calculated in Example 3-2-2.

FIG. 10-1 shows the chromatograms obtained by performing size exclusion chromatography on the urine samples from the rats treated with HA-Ala/FL prepared in Example 1-4-1.

FIG. 10-2 shows the chromatograms obtained by performing size exclusion chromatography on the urine samples from the rats treated with HA-Ser/FL prepared in Example 1-4-2.

FIG. 10-3 shows the chromatograms obtained by performing size exclusion chromatography on the urine samples from the rats treated with HA-Glu/FL prepared in Example 1-4-3.

FIG. 10-4 shows the chromatograms obtained by performing size exclusion chromatography on the urine samples from the rats treated with HA-Gly/FL prepared in Example 1-4-4.

FIG. 10-5 shows the chromatograms obtained by performing size exclusion chromatography on the urine samples from the rats treated with HA-Val/FL prepared in Example 1-4-5.

FIG. 10-6 shows the chromatograms obtained by performing size exclusion chromatography on the urine samples from the rats treated with HA-Leu/FL prepared in Example 1-4-6.

FIG. 10-7 shows the chromatograms obtained by performing size exclusion chromatography on the urine samples from the rats treated with HA-Ile/FL prepared in Example 1-4-7.

FIG. 10-8 shows the chromatograms obtained by performing size exclusion chromatography on the urine samples from the rats treated with HA-Thr/FL prepared in Example 1-4-8.

FIG. 10-9 shows the chromatograms obtained by performing size exclusion chromatography on the urine samples from the rats treated with HA-Asp/FL prepared in Example 1-4-9.

FIG. 10-10 shows the chromatograms obtained by performing size exclusion chromatography on the urine samples from the rats treated with HA-cACHCA/FL prepared in Example 1-4-10.

FIG. 10-11 shows the chromatograms obtained by performing size exclusion chromatography on the urine samples from the rats treated with HA-tACHCA-OEt/FL prepared in Example 1-4-11.

FIG. 10-12 shows the chromatograms obtained by performing size exclusion chromatography on the urine samples from the rats treated with HA-Aib/FL prepared in Example 1-4-12.

FIG. 10-13 shows the chromatograms obtained by performing size exclusion chromatography on the urine samples from the rats treated with HA-ACBuCA-OEt/FL prepared in Example 1-4-13.

FIG. 10-14 shows the chromatograms obtained by performing size exclusion chromatography on the urine samples from the rats treated with HA-Asn/Rh prepared in Example 14-14.

FIG. 10-15 shows the chromatograms obtained by performing size exclusion chromatography on the urine samples from the rats treated with HA-Ala-NH$_2$/Rh prepared in Example 1-4-15.

FIG. 10-16 shows the chromatograms obtained by performing size exclusion chromatography on the urine samples from the rats treated with HA-Val-NH$_2$/Rh prepared in Example 1-4-16.

FIG. 10-17 shows the chromatograms obtained by performing size exclusion chromatography on the urine samples from the rats treated with HA-Asn-NH$_2$/Rh prepared in Example 1-4-17.

FIG. 10-18 shows the chromatograms obtained by performing size exclusion chromatography on the urine samples from the rats treated with HA-Me/FL prepared in Example 14-18.

FIG. 10-19 shows the chromatograms Obtained by performing size exclusion chromatography on the urine samples from the rats treated with HA-Pr/FL prepared in Example 1-4-19.

FIG. 10-20 shows the chromatograms obtained by performing size exclusion chromatography on the urine samples from the rats treated with HA-FL prepared in Comparative Example 1-1-1.

FIG. 10-21 shows the chromatograms obtained by performing size exclusion chromatography on the urine samples from the rats treated with HA-EDOBEA-Ac/FL prepared in Comparative Example 1-1-2.

FIG. 10-22 shows the chromatograms obtained by performing size exclusion chromatography on the urine samples from the rats treated with HA-Phe/FL prepared in Comparative Example 1-1-3.

FIG. 10-23 shows the chromatograms obtained by performing size exclusion chromatography on the urine samples from the rats treated with HA-Tyr/FL prepared in Comparative Example 1-1-4.

FIG. 10-24 shows the chromatograms obtained by performing size exclusion chromatography on the urine samples from the rats treated with HA-MePhe/FL prepared in Comparative Example 1-1-5.

FIG. 10-25 shows the chromatograms obtained by performing size exclusion chromatography on the urine samples from the rats treated with HA-Pro-OMe/FL prepared in Comparative Example 1-1-6, FIG. 10-26 shows the chromatograms obtained by performing size exclusion chromatography on the urine samples from the rats treated with HA-Gly-NH$_2$/Rh prepared in Comparative Example 1-1-7.

FIG. 10-27 shows the chromatograms obtained by performing size exclusion chromatography on the urine samples from the rats treated with HA-Ser-NH$_2$/16 prepared in Comparative Example 1-1-8.

FIG. 10-28 shows the chromatograms obtained by performing size exclusion chromatography on the urine samples from the rats treated with HA-Leu-NH$_2$/Rh prepared in Comparative Example 1-1-9.

FIG. 10-29 shows the chromatograms obtained by performing size exclusion chromatography on the urine samples from the rats treated with HA-Ile-NH$_2$/Rh prepared in Comparative Example 1-1-10.

FIG. 10-30 shoes the chromatograms obtained by performing size exclusion chromatography on the urine samples from the rats treated with HA-Thr-NH$_2$/Rh prepared in Comparative Example 1-1-11

FIG. 10-31 shows the chromatograms obtained by performing size exclusion chromatography on the urine samples from the rats treated with HA-Gln-NH$_2$/Rh prepared in Comparative Example 1-1-12.

FIG. 11 is a table showing the liposome degradation degrees of the HA derivatives according to the present invention as evaluated in Example 4-2.

FIG. 12-1 shows examples of the $^1$H-NMR spectra of the sample for calculating modification degrees with alanine, and HA-Ala-TBA, which were prepared in Example 5-1.

FIG. 12-2 shows an example of the $^1$H-NMR spectrum of HA-Ala-EDOBEA prepared in Example 5-2.

FIG. 12-3 shows an example of the $^1$H-NMR spectrum of HA-Ala-EDOBEA-Rh prepared in Example 5-3.

FIG. 13 shows the group averages for the time courses of sample concentrations in rat plasma as calculated in Example 6-2-2.

FIG. 14 shows the chart that plots the group averages for the time courses of sample concentrations it rat plasma as calculated in Example 6-2-2.

FIG. 15 shows the chromatograms obtained by performing size exclusion chromatography on the urine samples from the rats treated with HA-Ala-PTH/Rh prepared Example 5-5.

DESCRIPTION OF EMBODIMENTS

The hyaluronic acid derivative of the present invention is not particularly limited as long as it is a hyaluronic acid derivative comprising one or more disaccharide units represented by Formula (I). In one embodiment of the present invention, the proportion of the disaccharide units of Formula (I) with respect to disaccharide repeating units present in the hyaluronic acid derivative of this invention is for example at least 70%, preferably at least 75%, and more preferably at least 90%. The upper limit of said proportion can be any value not greater than 100%. In one embodiment of the present invention, a hyaluronic, acid derivative comprising one or more disaccharide units represented by Formula (I) and one or more disaccharide units represented by Formula (II) and/or (III) is provided.

In one embodiment of the present invention, the hyaluronic acid derivative is substantially composed of disaccharide units of Formulas (I) and (II). In the hyaluronic acid derivative, for example at least 80%, preferably at least 90%, and more preferably at least 95% of its constitutional disaccharide repeating units composed of D-glucuronic acid and N-acetylglucosamine are occupied by the disaccharide units of Formula (I) or (H). In one embodiment of the present invention, the hyaluronic acid derivative is composed exclusively of disaccharide units represented by Formulas (I) and (II).

In one embodiment of the present invention, the hyaluronic acid derivative is substantially composed of disaccharide units of Formulas (I), (II) and (III). In the hyaluronic acid derivative, for example at least 80%, preferably at least 90%, and more preferably at least 95% of its constitutional disaccharide repeating units composed of D-glucuronic acid and N-acetylglucosamine are occupied by the disaccharide units of Formula (I), (II) or (III). In one embodiment of the present invention, the hyaluronic acid derivative is composed exclusively of disaccharide units represented by Formulas (I), (II) and (III).

The proportion of particular disaccharide units with respect to disaccharide repeating units present in the hyaluronic acid derivative of the present invention preferably means the proportion of particular disaccharide units with respect to all disaccharide units present in a certain amount of the hyaluronic acid derivative of this invention which is a polysaccharide composed of repeating units of a disaccharide.

In Formula (I) which represents a disaccharide unit present in the hyaluronic acid derivative of the present invention, $R^1$, $R^2$, $R^3$, and $R^4$ are all preferably hydrogen atoms. $R^8$ is preferably a hydrogen atom or $C_{1-6}$ alkylcarbonyl, more preferably a hydrogen atom or acetyl, and even more preferably acetyl. In Formulae (II) and (III) which represent disaccharide units present in the hyaluronic acid derivative of this invention, $R^{1a}$, $R^{2a}$, $R^{3a}$ and $R^{4a}$ as well as $R^{1b}$, $R^{2b}$, $R^{3b}$ and $R^{4b}$ are all preferably hydrogen atoms. $R^{8a}$ and $R^{8b}$ are each preferably a hydrogen atom or $C_{1-6}$ alkylcarbonyl, more preferably a hydrogen atom or acetyl, and even more preferably acetyl.

In Formula (I), when -A-B—Z is $C_{1-6}$ alkyl, $C_{1-3}$ alkyl is preferred, and methyl or n-propyl is particularly preferred.

In Formula (I), $R^x$ is a hydrogen atom, or $C_{1-6}$ alkyl such as methyl and ethyl, and is preferably a hydrogen atom $R^y$ is a hydrogen atom, or $C_{1-6}$ alkyl such as methyl and ethyl, and is preferably a hydrogen atom, methyl or ethyl.

In Formula (I), when A or B is $C_{3-8}$ cycloalkylene, examples of the $C_{3-8}$ cycloalkylene include 1,1-cyclohexylene, 1,2-cyclohexylene, 1,3-cyclohexylene, 1,4-cyclohexylene, 1,1-cyclopentylene, 1,2-cyclopentylene, 1,3-cyclopentylene, 1,1-cyclobutylene, 1,2-cyclobutylene, and 1,3-cyclobutylene. Preferred examples include 1,1-cyclohexylene, 1,2-cyclohexylene, 1,4-cyclohexylene, and 1,1-cyclobutylene. From the viewpoint of provision of both biodegradability and retentivity in blood, the $C_{3-8}$ cycloalkylene is preferably 1,1-cyclohexylene, 1,2-cyclohexylene, or 1,1-cyclobutylene, and from the viewpoint of delivery of a gene or a drug into the cytoplasm, the $C_{3-8}$ cycloalkylene is preferably 1,4-cyclohexylene.

In Formula (I), when B is phenylene, examples of the phenylene include 1,2-phenylene, 1,3-phenylene, and 1,4-phenylene. Preferred examples include 4-phenylene and 1,3-phenylene. Also, when B is phenylene, particularly preferred examples include 1,4-phenylene.

The phenylene may be substituted by one or more groups selected from hydroxy and halogen atoms. Specific examples of the substituted phenylene include 2-hydroxy-1,4-phenylene, 3-hydroxy-1,4-phenylene, 2,3-dihydroxy-1,4-phenylene, 3,5-dihydroxy 1,4-phenylene, 5-hydroxy-1,3-phenylene, 3-hydroxy-1,2-phenylene, and 4-hydroxy-1,2-phenylene; 2-chloro-1,4-phenylene, 2-iodo-1,4-phenylene, 3-bromo-1,4-phenylene, 2,6-difluoro-1,4-phenylene, 3,5-dichloro-1,4-phenylene, 5-chloro-1,3-phenylene, 3-bromo-1,2-phenylene, and 4-chloro-1,2-phenylene; 6-fluoro-2-hydroxy-1,4-phenylene, 5-chloro-3-iodo-1,4-phenylene, 2-bromo-3 hydroxy-1,4-phenylene, 5-bromo-3-chloro 1,4-phenylene, 5-hydroxy-6-iodo-1,3-phenylene, 3-chloro-4-hydroxy-1,2-phenylene, and 4-bromo-3-chloro-1,2-phenylene, and preferably include 3-hydroxy-1,4-phenylene, and 2-chloro-1,4-phenylene.

$R^c$ is $C_{1-6}$ alkyl which may be substituted by carbamoyl (—$CONH_2$), and is preferably methyl, isopropyl or carbamoylmethyl, and is more preferably isopropyl or carbamoylmethyl.

$R^{ya}$ and $R^{yb}$ are each independently selected from a hydrogen atom, $C_{1-6}$ alkyl, formyl and $C_{1-6}$ alkylcarbonyl; preferably, both of them are hydrogen atoms, or one of them is a hydrogen atom and the other is $C_{1-6}$ alkyl, or one of them is a hydrogen atom and the other is $C_{1-6}$ alkylcarbonyl; more preferably, both of them are hydrogen atoms, or one of them is a hydrogen atom and the other is methyl, or one of them is a hydrogen atom and the other is ethyl; and even more preferably, both of them are hydrogen atoms. In Formula (I), X is exemplified by the following groups:

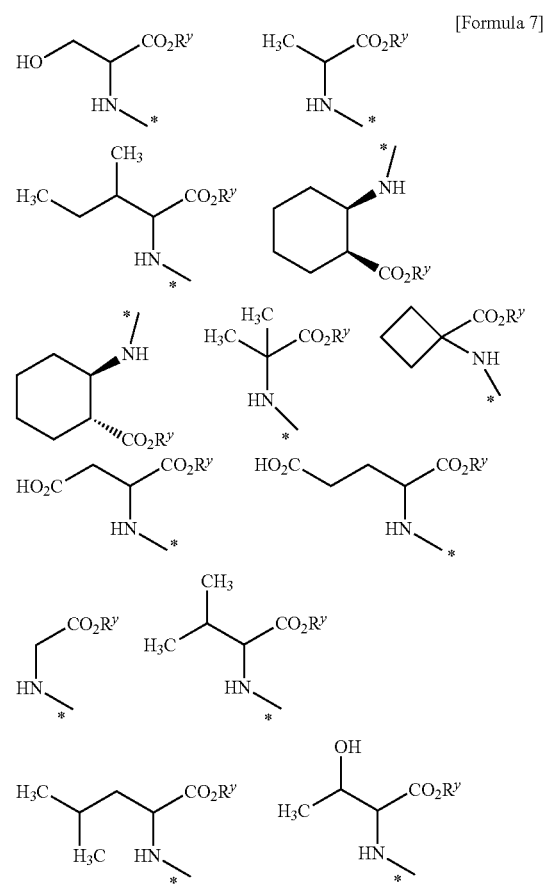

[Formula 7]

[wherein $R^y$ is as defined herein].

The exemplar groups are preferred from the viewpoint of provision of both biodegradability and retentivity in blood.

Further, X in Formula (I) is exemplified by the following groups:

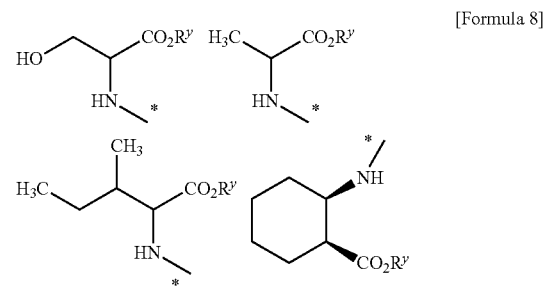

[Formula 8]

-continued

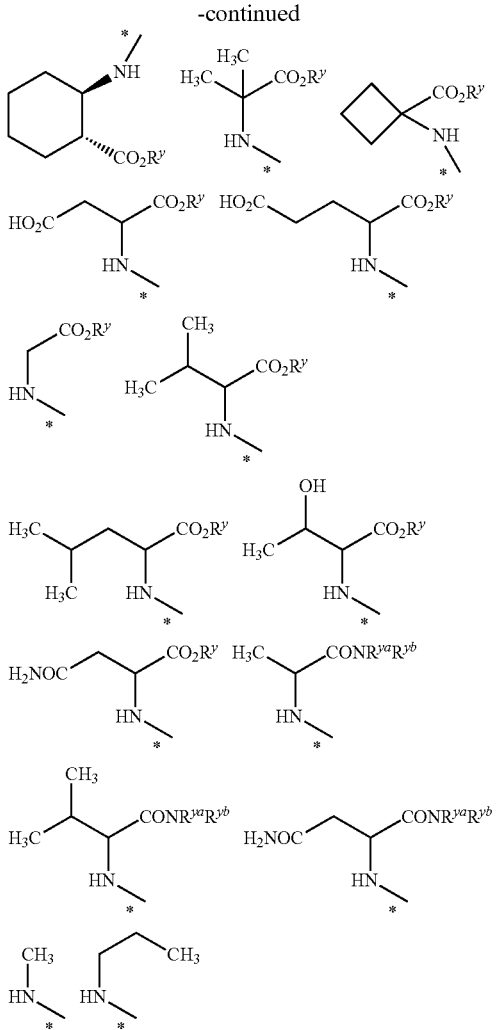

[wherein $R^y$, $R^{ya}$ and $R^{yb}$ are as defined herein].

In the foregoing formulas, "*" represents a bonding position to carboxy in the hyaluronic acid derivative (the same applies hereinafter).

In one embodiment of the present invention, it is preferred from the viewpoint of provision of both biodegradability and retentivity in blood that as defined in Formula (I), A be —$CR^aR^b$— (wherein $R^a$ is as defined above, and $R^b$ is selected from a hydrogen atom and $C_{1-6}$ alkyl (wherein the $C_{1-6}$ alkyl may be substituted by a group selected from hydroxy and carboxy)), and B be a direct bond; or that A be $C_{3-8}$ cycloalkylene, and B be a direct bond.

In another embodiment of the present invention, it is preferred from the viewpoint of provision of both biodegradability and retentivity in blood that as defined in Formula (I), X be —$NHCH_3$, —$NH(CH_2)_2CH_3$ or $NR^x$—$CHR^c$—$CONR^{ya}R^{yb}$; or that A be —$CR^aR^b$— (wherein $R^a$ is as defined above, and $R^b$ is selected from a hydrogen atom and $C_{1-6}$ alkyl (wherein the $C_{1-6}$ alkyl may be substituted by a group selected from hydroxy, carboxy and carbamoyl)), and B be a direct bond; or that A be $C_{3-8}$ cycloalkylene, and B be a direct bond.

$R^a$ is more preferably a hydrogen atom and methyl, and even more preferably a hydrogen atom. $R^b$ is preferably a hydrogen atom and $C_{1-4}$ alkyl (wherein the $C_{1-4}$ alkyl may be substituted by a group selected from hydroxy and carboxy), and more preferably methyl which may be substituted by hydroxy. Preferred examples of $R^b$ include a hydrogen atom and $C_{1-4}$ alkyl (wherein the $C_{1-4}$ alkyl may be substituted by a group selected from hydroxy, carboxy and carbamoyl).

B is preferably cyclohexane-1,2-diyl and cyclobutane-1,1-diyl, and more preferably cyclohexane-1,2-diyl. It is preferred that the configuration of —$NR^x$- and —$COOR^y$ on the cyclohexane ring be any of cis-configuration and trans-configuration. In the hyaluronic acid derivative of the present invention, the configurations of —$NR^x$— and —$COOR^y$ on the cyclohexane rings may consist exclusively of either cis-configurations or trans-configurations, or may consist of cis-configurations and trans-configurations in any ratio. Alternatively, the configuration of each group may consist of either one type of configuration or may consist of both types of configurations in any ratio.

From the viewpoint of provision of both biodegradability and retentivity in blood, specific examples of the preferred X include, but are not limited to, the groups represented by the following formulas:

[Formula 9]

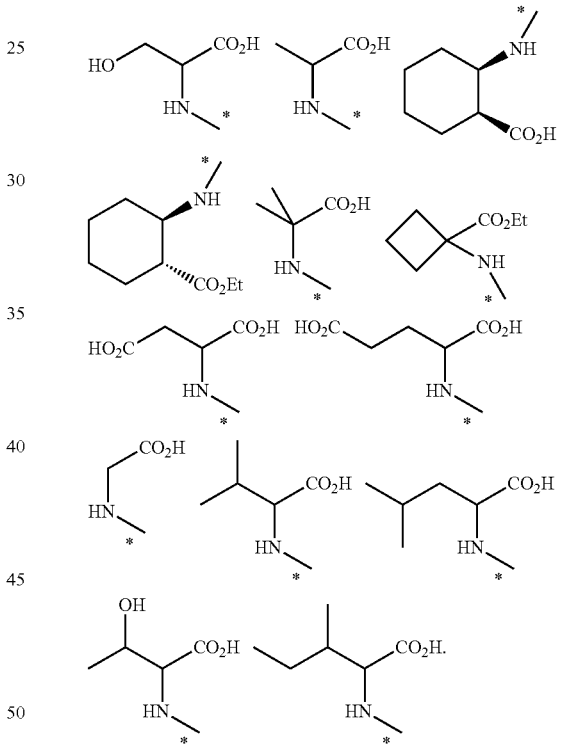

From the viewpoint of provision of both biodegradability and retentivity in blood, other specific examples of the preferred X include, but are not limited to, the groups represented by the following formulas:

[Formula 10]

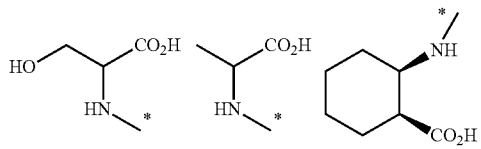

-continued
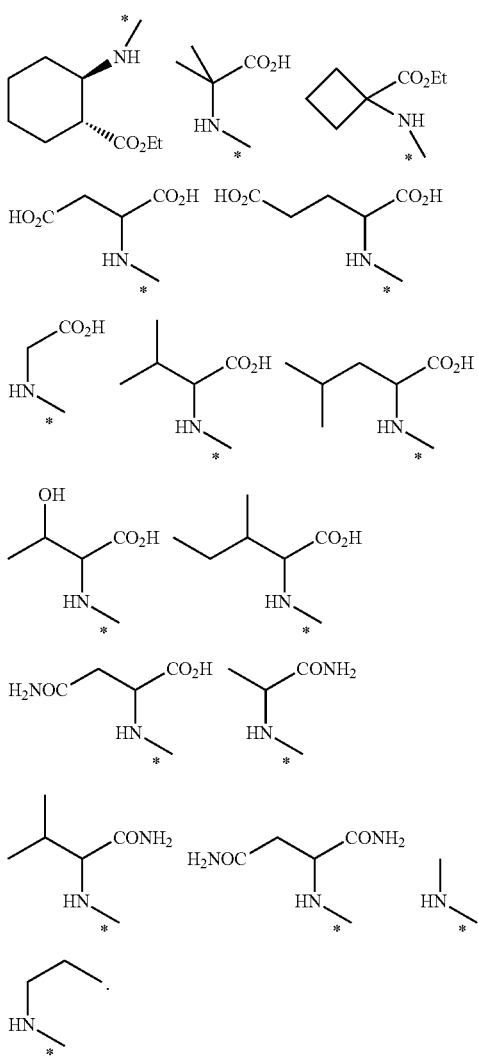
Specific examples of the more preferred X include the following groups:
[Formula 11]
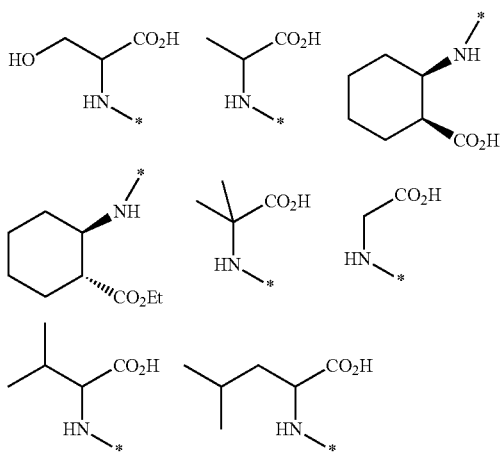
-continued
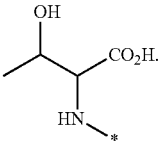
Other specific examples of to preferred X include the following groups:
[Formula 12]
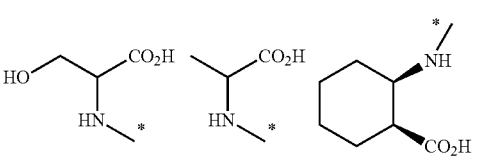
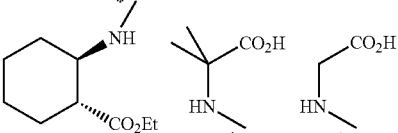
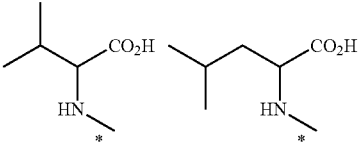
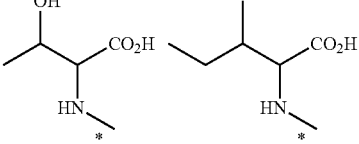
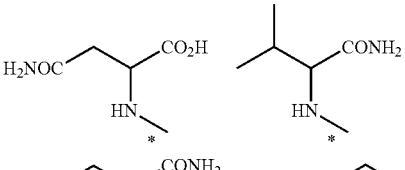
Specific examples of the more preferred X include the following groups:
[Formula 13]
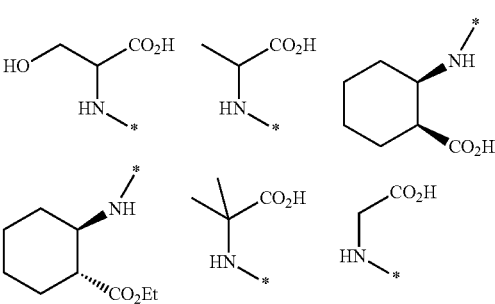

-continued

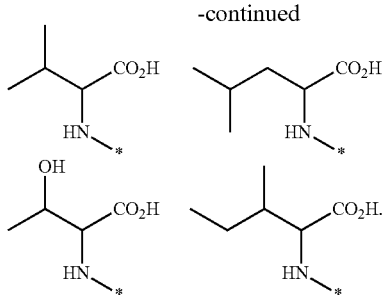

Other specific examples of the more preferred X include the following groups:

[Formula 14]

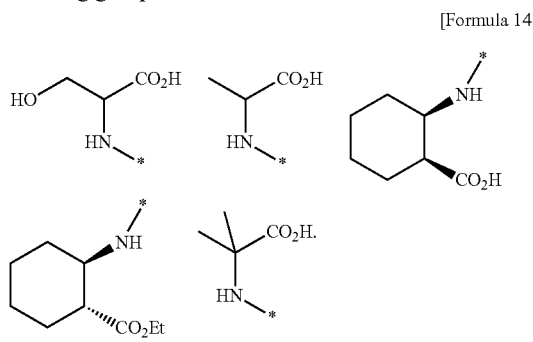

Specific examples of the particularly preferred X include the following groups:

[Formula 15]

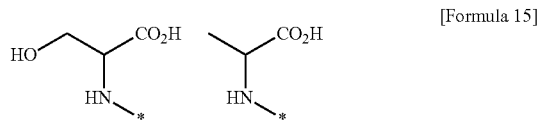

From the viewpoint of provision of both biodegradability and retentivity in blood, the proportion of disaccharide units of Formula (I) with respect to disaccharide repeating units present in the hyaluronic acid derivative of the present invention is preferably at least 70%, more preferably at least 75%, and even more preferably at least 90%.

in one embodiment of the present invention, it is preferred from the viewpoint of delivery of a gene or a drug into the cytoplasm that as defined in Formula (I), A be $C_{3-8}$ cycloalkylene, and B be a direct bond; or that A be —$CH_2$—, and B be selected from phenylene and $C_{3-8}$ cycloalkylene; or that A be selected from 2-cyclohexylethane-1,1-diyl, 2-(2-naphthyl)ethane-1,1-diyl and 3-phenylpropane-1,1-diyl, and B be a direct bond. It is more preferred that as defined in Formula (I), A be —$CH_2$—, and B be selected from cyclohexane-1,1-diyl and benzene-1,4-diyl; or that A be selected from 2-cyclohexylethane-1,1-diyl, 2-(2-naphthyl)ethane-1-diyl and 3-phenylpropane-1,1-diyl.

In another embodiment of the present invention, it is preferred from the viewpoint of delivery of a gene or a drug into the cytoplasm that as defined in Formula (I), A be $C_{3-8}$ cycloalkylene, and B be a direct bond; or that A be —$CH_2$— or —$CH_2$—$CH_2$—, and B be selected from phenylene (wherein the phenylene may be substituted by one or more groups selected from hydroxy and halogen atoms), $C_{3-8}$ cycloalkylene and phenylmethane-1,1-diyl; or that A be selected from 2-cyclohexylethane-1,1-diyl, 2-(2-naphthyl)ethane-1,1-diyl, 3-phenylpropane-1,1-diyl, cyclohexylmethane-1,1-diyl and 4-hydroxyphenylmethane-1,1-diyl, and B be a direct bond. It is more preferred that as defined in Formula (I), A be —$CH_2$—, and B be selected from cyclohexane-1,1-diyl, benzene-1,4-diyl, benzene-1,3-diyl, 2-chlorobenzene-1,4-diyl and phenylmethane-1,1-diyl; or that A be —$CH_2CH_2$—, and B be benzene-1,4-diyl; or that A be selected from 2-cyclohexylethane-1,1-diyl, 2-(2-naphthyl)ethane-1,1-diyl and 3-phenylpropane-1,1-diyl.

From the viewpoint of delivery of a gene or a drug into the cytoplasm, specific examples of the preferred X include, but are not limited to, the groups represented by the following formulas:

[Formula 16]

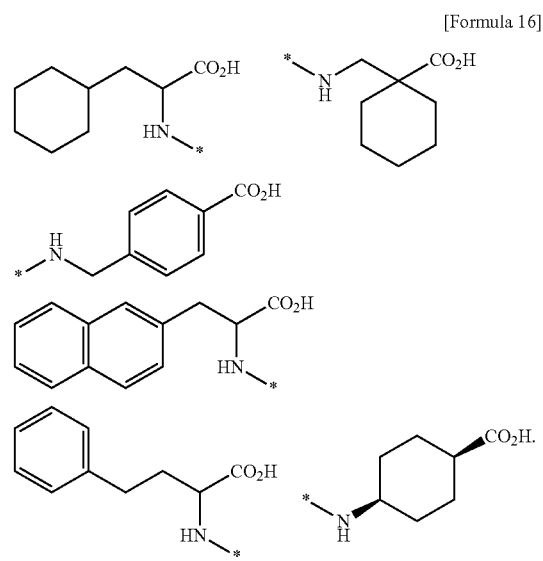

From the viewpoint of delivery of a gene or a drug into the cytoplasm, specific examples of the preferred X include, but are not limited to, the groups represented by the following formulas:

[Formula 17]

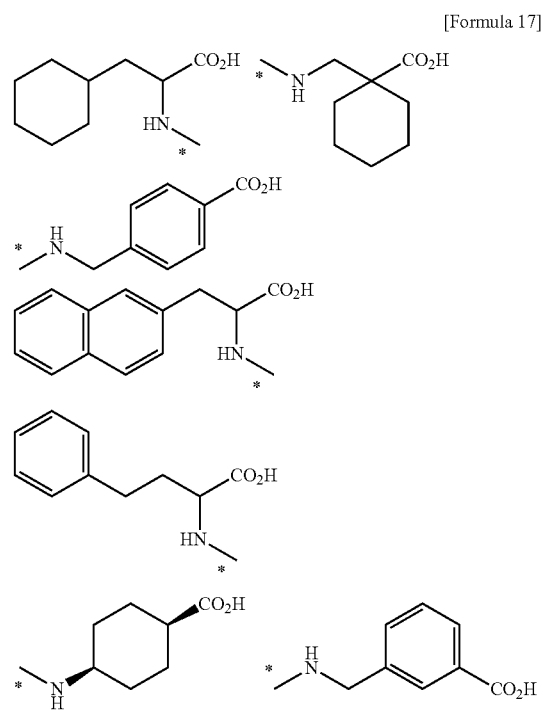

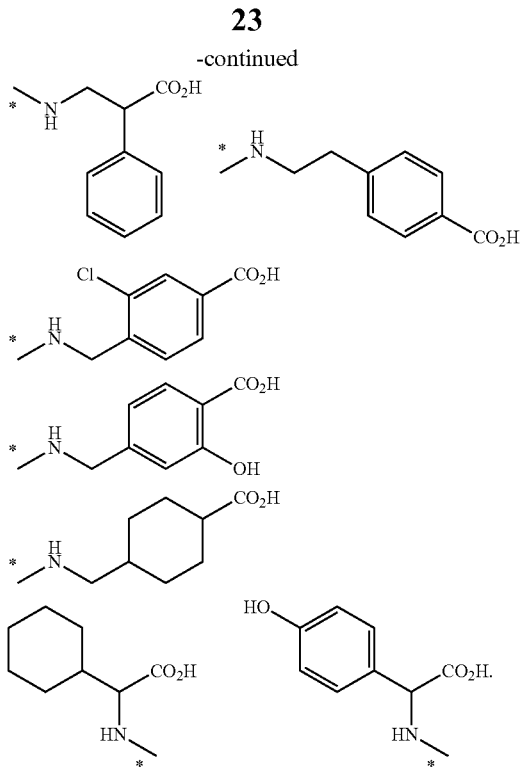

Specific examples of the more preferred X include the following groups:

[Formula 18]

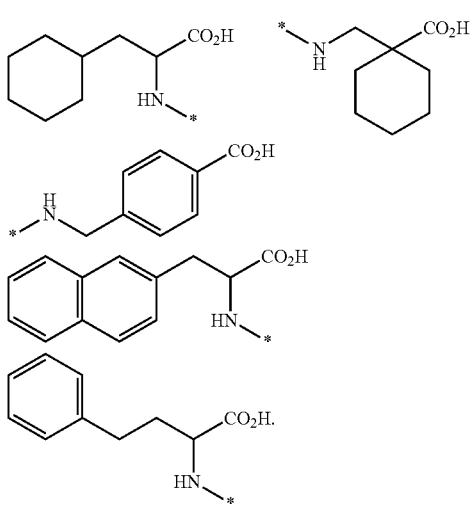

Other specific examples of the more preferred X include the following groups:

[Formula 19]

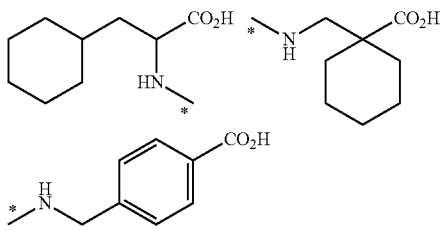

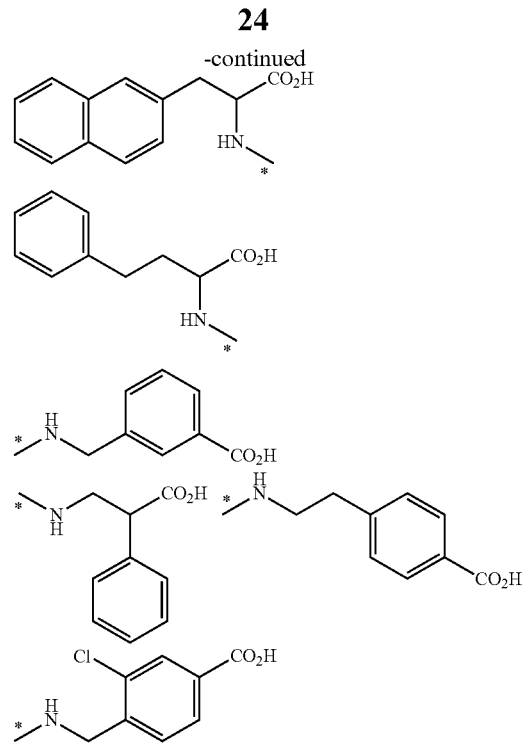

When X in Formula (I) contains one or more asymmetric points, the configuration at each asymmetric point may consist exclusively of either R- or S-configuration, or may consist of both of the configurations in any ratio.

It should be noted that the following groups:

[Formula 20]

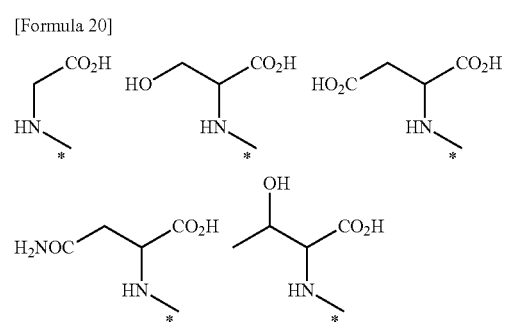

or the following groups:

[Formula 21]

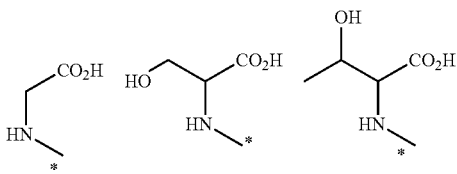

can be excluded from X in Formula (I).

In Formula (II), $Q^+$ is not particularly limited as long as it is a counteraction that forms a salt with carboxy in water, and when it is di- or higher-valent, it forms a salt with two or more carboxy groups depending on the valency. Examples of the counteraction include, but are not limited to, metal ions such as lithium ion, sodium ion, rubidium ion, cesium ion, magnesium ion, calcium ion; and an ammonium ion represented by the formula $N^+R^jR^kR^lR^m$ (wherein $R^j$, $R^k$, $R^l$ and $R^m$ are each independently selected from a hydrogen atom and $C_{1-6}$ alkyl), and preferably include sodium ion, potassium ion, and tetraalkylammonium ion (e.g., tetra-n-butylammonium ion). $R^j$, $R^k$, $R^l$, and $R^m$ are each preferably the same group selected from $C_{1-6}$ alkyls, and are each more preferably n-butyl.

In Formula (III), examples of $X^b$ include the following groups:

—HN—$(CH_2)_j$—SH;

—HN—$CH_2$—$CH_2$—$(Y^1$—$CH_2$—$CH_2)_c$—SH;

—HN—$(CH_2)_p$—O—CO—$C(R^7)$=$CH_2$;

—HN—$(CH_2)_l$—NHCO—C—$(R^7)$=$CH_2$;

—HN—$CH_2$—$CH_2$—$(Y^1$—$CH_2$—$CH_2)_c$—NHCO—$C(R^7)$=$CH_2$; or

—HN—$CH_2$—$CH_2$—$(Y^1$—$CH_2$—$CH_2)_c$—O—CO—$C(R^7)$=$CH_2$

[wherein j, $Y^1$, c, p, $R^7$, and l are as previously defined herein].

In the present invention, "$C_{1-6}$ alkyl" means straight-chain or branched-chain alkyl containing 1 to 6 carbon atoms, and examples include "$C_{1-4}$ alkyl" such as methyl, ethyl, n-propyl, i-propyl, n-butyl, s-butyl, i-butyl, and t-butyl, as well as n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl.

In the present invention, "$C_{1-6}$ alkylcarbonyl" means alkylcarbonyl having straight-chain or branched-chain alkyl containing 1 to 6 carbon atoms, and examples include, but are not limited to, acetyl, propionyl, butyryl, isobutyryl, pivaloyl, valeryl, isovaleryl, and hexanoyl.

In the present invention, "aryl" means an aromatic carbocyclic group such as an aromatic carboxyclic group containing 6 to 14 carbon atoms, and examples of aryl include, but are not limited to, phenyl and naphthyl (1-naphthyl, 2-naphthyl and 3-naphthyl), In the present invention, "$C_{3-8}$ cycloalkyl" means cyclic alkyl containing 3 to 8 carbon atoms, and examples include cyclopropyl, cyclobutyl, cyclopentyl, cyclohexyl, cycloheptyl, and cyclooctyl.

In the present invention, "$C_{3-8}$ cycloalkylene" means divalent cyclic alkyl containing 3 to 8 carbon atoms, and examples include cyclopropylene, cyclobutylene, cyclopentylene, cyclohexylene, cycloheptylene, and cyclooctylene. More specific examples include, but are not limited to, 1,1-cyclohexylene, 1,2-cyclohexylene, 1,3-cyclohexylene, 1,4-cyclohexylene, 1,1-cyclopentylene, 1,2-cyclopentylene, 1,3-cyclopentylene, 1,1-cyclobutylene, 1,2-cyclobutylene, and 1,3-cyclobutylene. Preferred examples include 1,1-cyclohexylene, 1,2-cyclohexylene, 1,4-cyclohexylene, and 1,1-cyclobutylene.

In the present invention, "phenylene" means a divalent group in which two hydrogen atoms in benzene are substituted, and examples include benzene-1,2-diyl, benzene-1,3-diyl, and benzene-1,4-diyl.

In the present invention, "$C_{1-10}$ alkylene" means a straight-chain or branched-chain alkylene group containing 1 to 10 carbon atoms, and examples include methylene, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, propane-1,2-diyl, 2-methylpropane-1,3-diyl, butane-2,4-diyl, 3-methylbutane-1,4-diyl, 2-methylpentane-1,5-diyl, 4-ethylhexane-1,6-diyl, 4-methylheptane-2,7-diyl, 5-ethyloctane-1,8-diyl, and 6-methylnonane-1,9-diyl.

In the present invention, "$C_{1-10}$ alkylene having one to three $C_{3-8}$ cycloalkylenes or phenylenes inserted therein" means a $C_{1-10}$ alkylene group in which one to three, preferably one, phenylene(s) or $C_{3-8}$ cycloalkylene(s) is(are) inserted.

Preferred examples of $G^4$ include, but are not limited to, phenylene, or the groups represented by the following formulas:

[Formula 22]

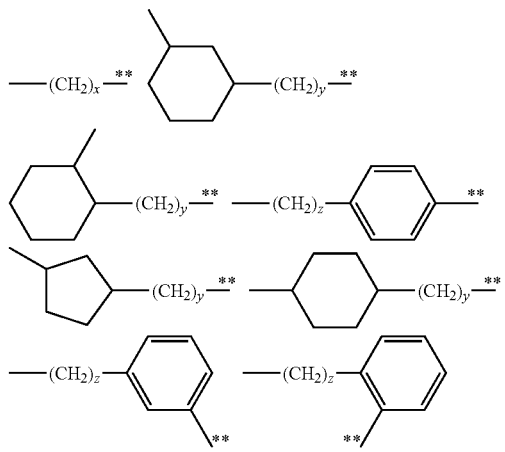

(wherein x is an integer selected from 1 to 10, y is an integer selected from 1 to 6, z is an integer selected from 1 to 5, and "**" represents a bonding position to $X^c$).

In the present invention, "halogen atom" means a fluorine atom, a chlorine atom, a bromine atom, or an iodine atom. When $X^c$ is a halogen atom, a chlorine atom, a bromine atom, and an iodine atom are preferred, and from the viewpoint of the reactivity with mercapto in a drug, a bromine atom and an iodine atom are preferred.

In the present invention, "drug carrier is biodegradable" means that the drug carrier detected in a urine 1 as been reduced in molecular weight until two weeks have passed after intravenous injection to a rat and/or a human.

In the present invention, "intracellular" means the inside of the cell membrane, including endosome and cell nucleus.

In the present invention, "intracytoplasmic" or "into the cytoplasm" means the inside of the cell membrane which excludes endosome and cell nucleus.

In the present invention, "endosome" means a vesicle composed of a biomembrane, which is formed in the process of the uptake of a substance by a cell, and a vesicle formed by fusing said vesicle with lysosome.

"reduced molecular weight" can be judged by determining the size of a drug carrier excreted in a urine by size exclusion chromatography (refer to Example 3-3 in this specification). If the peak top of the drug carrier derived from the urine as observed at any time point until two weeks after treatment or during a period of 24 hours shifts to the low molecular weight side as compared with that of the drug carrier derived from the urine collected at a previous time point or during a previous period (in other words, the retention time in the chromatogram becomes longer), then the drug carrier is judged to be biodegradable.

The hyaluronic acid derivative of the present invention comprising one or more disaccharide units represented by Formula (I) is typically synthesized using, as a starting material, hyaluronic acid or a derivative thereof which are substantially composed of disaccharide units represented by Formula (II), more preferably hyaluronic acid (including a salt there is composed exclusively of disaccharide units each represented by Formula (II). In one aspect of this invention, the weight-average molecular weight of the hyaluronic acid to be used as a starting material is in the range of 20-120 kilodaltons, and preferably in the range of 20-30 and 50-120 kilodaltons. The preferred weight-average molecular weight is exemplified by 25 kilodaltons and 99 kilodaltons. From the viewpoint of enhanced retentivity in blood, at least 5 kilodaltons is enough as the lower limit of the weight-average molecular weight, and it is preferably at least 50 kilodaltons, and more preferably at least 99 kilodaltons. The upper limit of the weight-average molecular weight is preferably not greater than 250 kilodaltons. The preferred weight-average molecular weight from the viewpoint of biodegradability is in the range of 50-120 kilodaltons, for example 99 kilodaltons, and the preferred weight-average molecular weight from the viewpoint of intracytoplasmic migration is in the range of 20-120 kilodaltons, for example 25 kilodaltons and 99 kilodaltons.

As referred to herein, the weight-average molecular weight ranging from 20 to 120 kilodaltons of the hyaluronic acid (including a salt thereof) which is composed exclusively of disaccharide units each represented by Formula (II) and used as a starting material means a weight-average molecular Weight as calculated on the assumption that in Formula (II), $R^{1a}$, $R^{2a}$, $R^{3a}$, and $R^{4a}$ are all hydrogen atoms, $R^{8a}$ is acetyl, and $X^a$ is —$O^-Na^+$, with the backbone structure of the hyaluronic acid derivative of the present invention being maintained. Thus, even in such a case that some or all disaccharide units in a starting material actually used have —$O^-$(tetra-n-butylammonium ion) as $X^a$ and thus the starting material has a weight-average molecular weight of 400 kilodaltons, the starting material shall be included as a preferred embodiment of the present invention as long as it has a weight-average molecular weight of 20-120 kilodaltons as calculated according to the above-mentioned assumption.

In order to determine the weight-average molecular weight of HA, various known methods including light-scattering method, osmometry, and viscometry, as typically disclosed in Seiichi Nakahama, et al., *Essential Polymer Science* (published by Kodansha Ltd., ISBN4-06-153310-X), can be used. As indicated herein, the weight-average molecular weights determined by the light-scattering method can be determined by a procedure commonly used in the technical field to which the present invention belongs, for example by using a multi-angle laser light scattering detector coupled with a size exclusion chromatographic analyzer (SEC-MALLS).

According to another aspect of the present invention, the hyaluronic acid derivative of this invention can be prepared using, as a starting material, the hyaluronic acid (including a salt thereof) substantially composed of disaccharide units represented by Formula (II), which has a weight-average molecular weight of not greater than 500 kilodaltons, preferably not greater than 250 kilodaltons. In one embodiment of the present invention, the hyaluronic acid derivative of this invention is a hyaluronic acid derivative substantially composed of disaccharide units of Formulas (I) and (II).

The hyaluronic acid derivative of the present invention comprising disaccharide units represented by Formula (I) can be prepared by amidating carboxy in its glucuronic acid moiety. A exemplary preparation processes is as follows: hyaluronic acid (including a salt thereof) as a starting material, preferably hyaluronic acid composed exclusively of disaccharide units each represented by Formula (II), is converted to a tetramethylammonium salt (e.g., tetrabutylammonium (TBA) salt) thereof through ion exchange, and the resulting hyaluronic acid salt is reacted with a compound represented by the formula $HNR^x$-A-B—$COOR^z$ (wherein $R^z$ is a group forming an ester for carboxy protection, and $R^x$, A and B are as previously defined herein) or the formula $HNR^x$-A-CON-$R^{ya}R^{yb}$ in a solvent in the presence of a suitable condensing agent, and deprotection is performed if any protecting group is present. As referred to herein, the group forming the ester is not particularly limited as long as it is a group commonly used for carboxy protection. Examples of the group forming the ester include $C_{1-6}$ alkyl, benzyl, $C_{1-6}$ alkoxy $C_{1-6}$ alkyl, and benzyloxy $C_{1-6}$ alkyl.

In Formula (I), the groups —$NR^x$-A-B—$COOR^z$ and —$NR^x$-A-$CONR^{ya}R^{yb}$ may be the same or different for two or more respective disaccharide units present. For example, the foregoing reaction may also be performed using different types of the compounds represented by formulas: $HNR^x$-A-B—$COOR^z$ and/or $HNR^x$-A-$CONR^{ya}R^{yb}$.

The condensing agent that can be used in the foregoing reaction is not particularly limited, and examples include, but are not limited to, 4-(4,6-dimethoxy-1,3,5-triazine)-4-methylmorpholinium (DMT-MM),
N,N'-carbonyldiimidazole (CDI), N,N'-dicyclohexylcarbodiimide (DCC),
N-ethoxycarbonyl-2-ethoxy-1,2-dihydroquinoline (EEDQ),
2-benzotriazole-1,1,3,3-tetramethyluronium tetrafluoroborate (TBTU),
3,4-dihydro-3-hydroxy-4-oxo-1,2,3-benzotriazine (HODhbt),
benzotriazole-1-oxy-tris-pyrrolidino-phosphonium hexafluorophosphate (PyBOP),
benzotriazole-1-yl-oxy-tris(dimethylamino)phosphonium hexafluorophosphate (BOP),
1-ethyl-3-(3-dimethylaminopropyl)carbodiimide (EDC), or
N-hydroxysuccinimide (NHS).

Although not particularly limited, DMT-MM is preferred in that the reaction proceeds with high efficiency even in a mixed solvent of water and an organic solvent. Also, by using DMT-MM as a condensing agent, highly selective amidation with amino and carboxy can be performed while esterification is reduced, in a system where many hydroxy groups coexist. The use of this condensing agent can prevents, for example, the reaction of an alcohol as a solvent with carboxy in the hyaluronic acid moiety, and undesired crosslinking caused by intramolecular or intermolecular bonding between carboxy and hydroxy coexisting in the hyaluronic acid moiety.

The solvent used in the foregoing reaction can be exemplified by water, dimethyl sulfoxide (DMSO), dimethylformamide (DMF), dimethylacetamide (DMAc), 1,3-dimethyl-2-imidazolidinone (DMI), sulfolan (SF), N-methylpyrrolidone (NMP), dioxane (e.g., 1,4-dioxane), methanol, ethanol, propanol, butanol, acetonitrile, tetrahydrofuran, dichloromethane, chloroform, hexane, diethyl ether, ethyl acetate, and mixed solvents thereof. From the viewpoint of the solubility of starting materials, modifiers and products, and the reactivity of condensing agents, it is preferred to use DMSO alone or to use a water/DMSO mixed solvent. Depending on the type of amino-carboxylic acid as a modifier, it can also be used in the reaction as a methanol solution or a dioxane solution.

The compound represented by the formula $HNR^x$-A-B—$COOR^z$ is exemplified by alanine ester, serine ester, glutamic acid diester, glycine ester, valine ester, leucine ester, isoleucine ester, threonine ester, asparatic acid diester, cis-2-amino-1-cyclohexylcarboxylic acid ester, trans-2-amino-1-cyclohexylcarboxylic acid ester, 2-aminoisobutyric acid ester, 1-amino-1-cyclobutyric acid ester, 1-aminomethyl-1-cyclohexanoic acid ester, cis-4-aminocyclohexanoic acid ester, L-2-naphthylalanine ester, 2-aminophenylbutyric acid ester, cyclohexyl-L-alanine ester, and 4-aminomethylbenzoic acid ester. Examples of the foregoing esters include, but are not limited to, $C_{1-6}$ alkyl ester, aryl ester, $C_{1-6}$ alkoxy $C_{1-6}$ alkyl ester, and $C_{1-6}$ aryl alkyl ester, with methyl ester, ethyl ester, benzyl ester, and the like being preferred.

The compound represented by the formula $HNR^x$-A-CON-$R^{ya}R^{yb}$ is exemplified by alaninamide, asparaginamide, asparatic acid amide, glutaminamide, glutamic acid amide, glycinamide, isoleucinamide, leucinamide, phenylalaninamide, serinamide, threoninamide, tyrosinamide, and valinamide.

The process for preparing the hyaluronic acid derivative of the present invention comprising disaccharide units represented by Formula (I) wherein X is —$NHCH_3$ or —NH$(CH_2)_2CH_3$ is exemplified by a process whereby the foregoing tetrabutylammonium salt of hyaluronic acid is reacted with a compound represented by $NH_2CH_3$ or $NH_2(CH_2)_2CH_3$ in a solvent in the presence of a suitable condensing agent. A condensing agent and a solvent as previously disclosed herein can be used in this reaction. The modification degree with each amine can be adjusted by, for example, controlling the number of equivalents of the condensing agent and/or the amine with respect to the HA unit, the reaction temperature, and/or the reaction time.

The process for preparing the hyaluronic acid derivative of the present invention comprising disaccharide units represented by Formula (III) is exemplified by a process whereby the foregoing tetrabutylammonium salt of hyaluronic acid is reacted with a compound represented by the formula $HNR^e$—$Y^b$—$R^w$ (wherein $R^w$ is a hydrogen atom, $C_{1-6}$ alkyl, —CO—$C(R^7)$=$CH_2$, —CO-$G^4$-$X^c$, a hydroxy protecting group, an amino protecting group, or a mercapto protecting group, and $R^e$, $Y^b$, $R^7$, $G^4$, and $X^c$ are as previously defined herein) in a solvent in the presence of a suitable condensing agent, and deprotection is performed if any protecting group is present. A condensing agent and a solvent as previously disclosed herein can be used in this reaction.

Specific examples of —CO-$G^4$-$X^c$ include the groups represented by the following formulas:

[Formula 23]

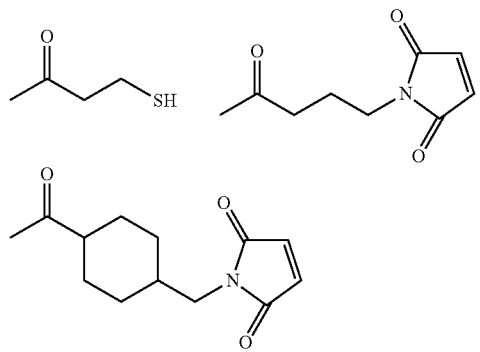
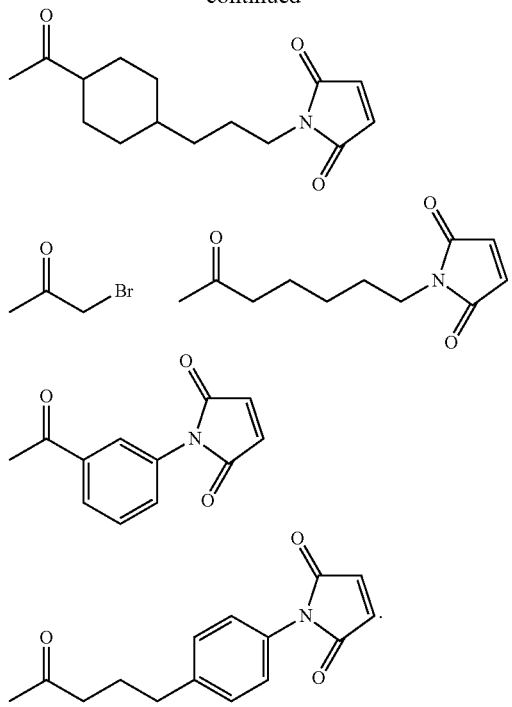

Specific examples of the protecting group used in the foregoing reaction are typically disclosed in T. W. Greene, P. G. M. Wuts, *Protective Groups in Organic Synthesis*, Third Edition, John Wiley & Sons, Inc., New York, 1999.

Examples of the hydroxy protecting group include $C_{1-6}$ alkylcarbonyl, arylcarbonyl, heteroarylcarbonyl, $C_{1-6}$ alkoxycarbonyl, $C_{1-6}$ alkoxy $C_{1-6}$ alkyl, $C_{1-6}$ alkylaminocarbonyl, di($C_{1-6}$ alkyl)aminocarbonyl, aryl $C_{1-6}$ alkyl, heteroaryl $C_{1-6}$ alkyl, aryl $C_{1-6}$ alkylaminocarbonyl, $C_{1-6}$ alkyl, $C_{1-6}$ alkylsulfonyl, ((amino $C_{1-6}$ alkyl)carbonyloxy)$C_{1-6}$ alkyl, unsaturated heterocyclic carbonyloxy $C_{1-6}$ alkyl, aryl di($C_{1-6}$ alkyl)silyl, and tri($C_{1-6}$ alkyl)silyl. The preferred hydroxy protecting group is exemplified by acetyl.

Examples of —NH— or the amino protecting group include, but are not limited to, $C_{1-6}$ alkylcarbonyl, aryl $C_{1-6}$ alkylcarbonyl, arylcarbonyl, heteroarylcarbonyl, $C_{1-6}$ alkoxycarbonyl, aryl $C_{1-6}$ alkylaminocarbonyl, di($C_{1-6}$ alkyl)aminocarbonyl, aryl $C_{1-6}$ alkyl, heteroaryl $C_{1-6}$ alkyl, and (aryl $C_{1-6}$ alkyl)aminocarbonyl. The preferred amino protecting group is exemplified by acetyl, t-butoxycarbonyl, and 9-fluorenylmethoxycarbonyl. Amino may be protected to form a saturated or unsaturated heterocyclic group such as phthalic acid imide, succinic acid imide, glutaric acid imide, and 1-pyrrolyl.

The mercapto protecting group is exemplified by $C_{1-6}$ alkylthio such as ethylthio and t-butylthio; substituted phenylthio such as 2-nitrophenylthio and 2-carboxyphenylthio; and heteroarylthio such as 2-pyridylthio. A preferred example is 2-pyridylthio.

Examples of the group represented by —$NR^e$—$Y^b$—$R^d$ in Formula (III) as mentioned above include the group represented by the following formula:

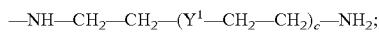

—NH—CH$_2$—CH$_2$—(Y$^1$—CH$_2$—CH$_2$)$_c$—OH;

—NH—(CH$_2$)$_j$—SH;

—NH—CH$_2$—CH$_2$—(Y$^1$—CH$_2$—CH$_2$)$_c$—SH;

—NH—(CH$_2$)$_p$—O—CO—C(R$^7$)=CH$_2$;

—NH—(CH$_2$)$_j$—NHCO—C(R$^7$)=CH$_2$;

—NH—CH$_2$—(CHR$^5$)$_{l-2}$—CH$_2$—NH—CO—CH$_2$—SH;

—NH—CH$_2$—CH$_2$—(Y$^1$—CH$_2$—CH$_2$)$_c$—NH—CO—CH$_2$—SH;

—NH—(CH$_2$)$_p$—O—CO—CH$_2$—CH$_2$—SH;

—NH—(CH$_2$)$_j$—NHCO—CH$_2$CH$_2$—SH;

NH—CH$_2$—CH$_2$—(Y$^1$—CH$_2$—CH$_2$)$_c$—O—CO—CH$_2$—CH$_2$—SH;

—NH—CH$_2$—(CHR$^5$)$_{l-2}$—CH$_2$—NH—CO—CH$_2$Br;

—NH—CH$_2$—CH$_2$—(Y$^1$—CH$_2$—CH$_2$)$_c$—NH—CO—CH$_2$—I;

—NH—CH$_2$—CH$_2$—(Y$^1$—CH$_2$—CH$_2$)$_c$—NHCO—C(R$^7$)=CH$_2$; or

—NH—CH$_2$—CH$_2$—(Y$^1$—CH$_2$—CH$_2$)$_c$—O—CO—C(R$^7$)=CH$_2$

[wherein R$^5$, R$^6$, R$^7$, Y$^1$, c, j, l, and p are as defined herein].

In these formulas, the respective numbers of CHR$^5$ and CHR$^6$ wherein R$^5$ and R$^6$ are hydroxy, which are contained in a molecule of the hyaluronic acid derivative, are in the range of 0 to 8, respectively, preferably in the range of 0 to 3, and more preferably 0 or 1. The water solubility of the hyaluronic acid derivative of the present invention can be adjusted by controlling the numbers of CHR$^5$ and CHR$^6$ wherein R$^5$ and R$^6$ are hydroxy. When all R$^5$'s are hydrogen atoms, 1 is preferably in the range of 2 to 6, and is specifically exemplified by 2 and 6. When one of R$^5$'s is hydroxy, 1 is specifically exemplified by 3. When Y$^1$ is an oxygen atom, c is specifically exemplified by 2. When Y$^i$ is —NH—, c is specifically exemplified by 1 to 3. 1 and p are specifically exemplified by 3.

Specific examples of —(CH$_2$)$_a$—(Y$^1$—(CH$_2$)$_b$)$_c$-G- include, but are not limited to, —(CH$_2$)$_2$—(O—CH$_2$—CH$_2$)$_c$—O—, —(CH$_2$)$_2$—(O—CH$_2$)$_c$—NH—, —(CH$_2$)$_3$—(O—CH$_2$—CH$_2$—CH$_2$)$_c$—O—, —(CH$_2$)$_3$—(O—CH$_2$—CH$_2$—CH$_2$)$_c$—NH—, —(CH$_2$)$_2$—NR″—(CH$_2$)$_2$—O—, —(CH$_2$)$_2$—NR″—(CH$_2$)$_2$—NH—, —(CH$_2$)$_3$—NR″—(CH$_2$)$_4$—O—, —(CH$_2$)$_3$—NR″—(CH$_2$)$_4$—NH—, —(CH$_2$)$_6$—NR″—(CH$_2$)$_6$—O—, —(CH$_2$)$_6$—NR″—(CH$_2$)$_6$—NH—, —(CH$_2$)$_3$—NR″—(CH$_2$)$_2$—NR″—(CH$_2$)$_3$—O—, —(CH$_2$)$_3$—NR″—(CH$_2$)$_2$—NR″—(CH$_2$)$_3$—NH—, —(CH$_2$)$_3$—NR″—(CH$_2$)$_4$—NR″—(CH$_2$)$_3$—O—, —(CH$_2$)$_3$—NR″—(CH$_2$)$_4$—NR″—(CH$_2$)$_3$—NH— (spermine-type), —(CH$_2$)$_2$—NR″—(CH$_2$)$_2$—NR″—(CH$_2$)$_2$—NR″—(CH$_2$)$_2$—O—, —(CH$_2$)$_2$—NR″—(CH$_2$)$_2$—NR″—(CH$_2$)$_2$—NR″—(CH$_2$)$_2$—NH—, —(CH$_2$)$_2$—NR″—(CH$_2$)$_2$—NR″—(CH$_2$)$_2$—NR″—(CH$_2$)$_2$—O—, and —(CH$_2$)$_2$—NR″—(CH$_2$)$_2$—NR″—(CH$_2$)$_2$—NR″—(CH$_2$)$_2$—NR″—(CH$_2$)$_2$—NH—. In these formulas, it is preferred that all R″'s be hydrogen atoms.

Specific examples of R$^d$ which is attached to any of these examples of —(CH$_2$)$_a$—(Y$^1$—(CH$_2$)$_b$)$_c$-G- include, but are not limited to, a hydrogen atom, —CO—CH=CH$_2$, —CO—C(CH$_3$)=CH$_2$, —CO—CH$_2$—Cl, —CO—CH$_2$—Br, —CO—CH$_2$—I, —CO—CH$_2$—SH, and —CO—CH$_2$—CH$_2$—SH.

Specific examples of the group represented by —NR$^e$—Y$^b$—R$^d$ include, but are not limited to, —NH—(CH$_2$)$_3$—N(—(CH$_2$)$_4$—NH—(CH$_2$)$_3$—NHCOCH$_3$)—(CH$_2$)$_2$—SH, —NH—(CH$_2$)$_2$—N(—(CH$_2$)$_3$—NH—(CH$_2$)$_4$—NHCOCH$_3$)—(CH$_2$)$_3$—SH, and —NH—(CH$_2$)$_5$—N(—(CH$_2$)$_3$—NH—(CH$_2$)$_2$—NHCOCH$_3$)—(CH$_2$)$_2$—SH.

The process for preparing the hyaluronic acid derivative of the present invention comprising disaccharide units represented by Formula (III) is exemplified by a process whereby carboxy (—COOH) in the glucuronic acid moiety of hyaluronic acid is reacted with a diamine represented by the formula H$_2$N—CH$_2$—(CHR$^5$)$_{l-2}$—C$_2$—NH$_2$ to convert it to an amide represented by the formula —CONH—CH$_2$—(CHR$^5$)$_{l-2}$—CH$_2$—NH$_2$, and then terminal amino is modified to convert said amide to an amide represented by the group —CONH—CH$_2$—(CHR$^5$)$_{l-2}$—CH$_2$—NHR$^d$.

Specific examples of the foregoing diamine include, but are not limited to, H$_2$N—(CH$_2$)$_2$—NH$_2$, H$_2$N—(CH$_2$)$_3$—NH$_2$, H$_2$N—(CH$_2$)$_4$—NH$_2$, H$_2$N—(CH$_2$)$_5$—NH$_2$, H$_2$N—(CH$_2$)$_6$—NH$_2$, H$_2$N—(CH$_2$)$_7$—NH$_2$, H$_2$N—(CH$_2$)$_8$—NH$_2$, H$_2$N—(CH$_2$)$_9$—NH$_2$, H$_2$N—(CH$_2$)$_{10}$—NH$_2$, H$_2$N—CH$_2$—CHOH—CH$_2$—NH$_2$, H$_2$N—CH$_2$—CHOH—(CH$_2$)$_2$—NH$_2$, H$_2$N—CH$_2$—(CHOH)$_2$—CH$_2$—NH$_2$, H$_2$N—CH$_2$—CHOH—(CH$_2$)$_3$—NH$_2$, H$_2$N—(CH$_2$)$_2$—CHOH—(CH$_2$)$_2$—NH$_2$, H$_2$N—CH$_2$—(CHOH)$_2$—(CH$_2$)$_2$—NH$_2$, H$_2$N—(CH$_2$—CHOH)$_2$—CH$_2$NH$_2$, H$_2$N—CH$_2$—(CHOH)$_3$—CH$_2$—NH$_2$, H$_2$N—CH$_2$—CHOH—(CH$_2$)$_4$—NH$_2$, H$_2$N—(CH$_2$)$_2$—CHOH—(CH$_2$)$_3$—NH$_2$, H$_2$N—CH$_2$—(CHOH)$_2$—(CH$_2$)$_3$—NH$_2$, H$_2$N—CH$_2$—CHOH—CH$_2$—CHOH—(CH$_2$)$_2$—NH$_2$, H$_2$N—CH$_2$—CHOH—(CH$_2$)$_2$—CHOH—CH$_2$—NH$_2$, H$_2$N—(CH$_2$)$_2$—(CHOH)$_2$—(CH$_2$)$_2$—NH$_2$, H$_2$N—CH$_2$—(CHOH)$_3$—(CH$_2$)$_2$—NH$_2$, H$_2$N—CH$_2$—(CHOH)$_2$—CH$_2$—CHOH—CH$_2$—NH$_2$, H$_2$N—(CH$_2$)$_2$—CHOH—(CH$_2$)$_4$—NH$_2$, —H$_2$N—(CH$_2$)$_3$—CHOH—(CH$_2$)$_4$—NH$_2$, H$_2$N—(CH$_2$)$_2$—CHOH—(CH$_2$)$_6$—NH$_2$, and H$_2$N—(CH$_2$)$_5$—CHOH—(CH$_2$)$_4$—NH$_2$.

The process for preparing the hyaluronic acid derivative of the present invention comprising disaccharide units represented by Formula (III) is exemplified by a process whereby carboxy (—COOH) in the glucuronic acid moiety of hyaluronic acid is reacted with a hydroxyamine represented by the formula H$_2$N—CH$_2$—(CHR$^5$)$_{p-2}$—CH$_2$—OH to convert it to an amide represented by the formula —CONH—CH$_2$—(CHR$^5$)$_{p-2}$—CH$_2$—OH, and then terminal amino is modified to convert said amide to an amide represented by the group —CONH—CH$_2$—(CHR$^5$)$_{p-2}$—CH$_2$—OR$^d$.

Specific examples of the foregoing hydroxylamine include, but are not limited to, H$_2$N—(CH$_2$)$_2$—OH, H$_2$N—(CH$_2$)$_3$—OH, H$_2$N—(CH$_2$)$_4$—OH, H$_2$N—(CH$_2$)$_5$—OH, H$_2$N—(CH$_2$)$_6$—OH, H$_2$N—(CH$_2$)$_7$—OH, H$_2$N—(CH$_2$)$_8$—OH, H$_2$N—(CH$_2$)$_9$—OH, H$_2$N—(CH$_2$)$_{10}$—OH, H$_2$N—CH$_2$—CHOH—CH$_2$—OH, H$_2$N—CH$_2$—CHOH—(CH$_2$)$_2$—OH, H$_2$N—CH$_2$—(CHOH)$_2$—CH$_2$—OH, H$_2$N—CH$_2$—CHOH—(CH$_2$)$_3$—OH, H$_2$N—(CH$_2$)$_2$—CHOH—(CH$_2$)$_2$—OH, H$_2$N—CH$_2$—(CHOH)$_2$—(CH$_2$)$_2$—OH, H$_2$N—(CH$_2$CHOH)$_2$—CH$_2$—OH, H$_2$N—CH$_2$—(CHOH)$_3$—CH$_2$—OH, H$_2$N—CH$_2$—CHOH—(CH$_2$)$_4$—OH, H$_2$N—(CH$_2$)$_2$—CHOH—(CH$_2$)$_3$—OH, H$_2$N—CH$_2$—(CHOH)$_2$—(CH$_2$)$_3$—OH, H$_2$N—CH$_2$—CHOH—CH$_2$—CHOH—(CH$_2$)$_2$—OH, H$_2$N—CH$_2$—CHOH—(CH$_2$)$_2$—CHOH—CH$_2$—OH, H$_2$N—(CH$_2$)$_2$—(CHOH)$_2$—(CH$_2$)$_2$—OH, H$_2$N—CH$_2$—(CHOH)$_3$—(CH$_2$)$_2$—OH, H$_2$N—CH$_2$—(CHOH)$_2$—CH$_2$—CHOH—CH$_2$—OH, H$_2$N—(CH$_2$)$_2$—

CHOH—(CH$_2$)$_4$—OH, H$_2$N—(CH$_2$)$_3$—CHOH—(CH$_2$)$_4$—OH, H$_2$N—(CH$_2$)$_2$—CHOH—(CH$_2$)$_6$—OH, and H$_2$N—(CH$_2$)$_5$—CHOH—(CH$_2$)$_4$—OH.

These compounds are typically commercially available from Sigma-Aldrich and can be purchased for use as appropriate. Alternatively, they may also be synthesized following a published method or using said method as a reference.

In Formula (III), the group —NR$^e$—Y$^b$—R$^d$ may be the same or different for two or more respective disaccharide units present. For example, the foregoing reaction may also be conducted using different types of the compound represented by the formula HNR$^e$—Y$^b$—R$^d$.

When X in Formula (I) is —NR$^x$-A-B—COOR$^y$, X$^b$ may be present at the position indicated in the disaccharide unit represented by Formula (III), or alternatively some or all X$^b$'s may be substituted with —OR$^y$ so that X may be —NR$^x$-A-B—CO—X$^b$, In one aspect of the present invention, an underivatized hyaluronic acid corresponding to the hyaluronic acid derivative of the present invention in terms of backbone structure has a weight-average molecular weight of 20-120 kilodaltons. Said underivatized hyaluronic acid (including a salt thereof) is hyaluronic acid composed exclusively of disaccharide units of Formula (II) wherein R$^{1a}$, R$^{2a}$, R$^{3a}$ and R$^{4a}$ are hydrogen atoms, R$^{8a}$ is acetyl, and X$^a$ is —O$^-$Na$^+$.

Since said underivatized hyaluronic acid corresponds to the hyaluronic acid derivative of the present invention in terms of backbone structure, the number of the disaccharide units present in said underivatized hyaluronic acid agrees with that of the hyaluronic acid derivative of this invention. The hyaluronic acid derivative in this aspect can be prepared typically using, as a starting material, hyaluronic acid having a weight-average molecular weight of 20-120 kilodaltons or a sodium salt thereof.

In one aspect of the present invention, the proportion of the disaccharide units of Formula (II) with respect to disaccharide units present is preferably not greater than 50%, more preferably not greater than 30%, and even more preferably not greater than 20%. The lower limit of the proportion can be any value not smaller than 0%. In this aspect, at least 50% of carboxy (—COOH) groups in the hyaluronic acid derivative are converted to the groups of —CONHCH$_3$, —CONH(CH$_2$)$_2$CH$_3$, —CONR$^x$-A-B—COOR$^y$, —CONR$^x$-A-CON-R$^{ya}$R$^{yb}$, or —CONR$^e$—Y$^b$—R$^d$.

The hyaluronic acid derivative comprising disaccharide units of Formula (III) having a reactive carbon-carbon double bond can be subjected to a crosslinking reaction with a crosslinking agent having two or more mercapto groups (e.g., dithiothreitol (DTT), butanedithiol, or polyethylene glycol dithiol). Also, the hyaluronic acid derivative comprising disaccharide units of Formula (III) having a mercapto group can be subjected to a crosslinking reaction via disulfide formation with a crosslinking agent having two or more mercapto groups (e.g., dithiothreitol (DTT), butanedithiol, or polyethylene glycol dithiol), or to a crosslinking reaction with a crosslinking agent having two or more reactive carbon-carbon double bonds (e.g., divinyl sulfone). Conducting a crosslinking reaction enables gelation of the hyaluronic acid derivative of this invention.

Other exemplary crosslinking reactions include: condensation-based crosslinking between derivative of hyaluronic acid modified with amino and a crosslinking agent comprising C$_{2-20}$ alkylene having a succinimidyl ester or any other imidoester at both terminal ends thereof (e.g., bis[sulfosuccinimidyl]suberate (BS$_3$), ethylene glycol-bis[sulfosuccinimidyl]succinate (Sulfo-EGS), or dimethyl adipimidate hydrochloride (DMA)); crosslinking between a derivative of hyaluronic acid modified with amino and a crosslinking agent comprising C$_{2-20}$ alkylene having formyl at both terminal ends thereof (e.g., glutaraldehyde); oxidation-based crosslinking of a derivative of hyaluronic acid modified with mercapto under oxidation conditions (e.g., in the presence of sodium tetrathionate (STT)); Michael addition-based crosslinking between a derivative of hyaluronic acid modified with mercapto and a crosslinking agent comprising alkylene having an unsaturated bond such as maleimide (MAL) or methacryloyl at both terminal ends thereof (e.g., 1,4-bis-maleimidebutane (BMB), ethylene dimethacrylate (EDMA)); radical polymerization-based crosslinking between a derivative of hyaluronic acid modified with an unsaturated bond such as acryloyl and methacryloyl and any of various polymerization initiators (e.g., potassium peroxodisulfate (KPS)/N,N,N',N'-tetramethylethylenediamine (TEMED), and Irgacure2959); and crosslinking with a condensing agent (e.g., N,N'-carbonyldiimidazole (CDT), N,N'-dicyclohexylcarbodiimide (DCC), N-ethoxycarbonyl-2-ethoxy-1,2-dihydroquinoline (EEDQ), 4-(4,6-dimethoxy-1,3,5-triazine)-4-methylmorpholinium chloride (DMT-MM), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-tris-pyrrolidino-phosphonium hexafluorophosphate (PyBOP), benzotriazole-1-yl-oxy-tris(dimethylamino)phosphonium hexafluorophosphate (BOP), 1-ethyl-3-(3-dimethylaminopropyl)carbodiimide (EDC), or N-hydroxysuccinimide (NHS)) in the presence of a diamine compound (e.g., EDA or 2,2'-ethylenedioxy)bis(ethylenediamine)). The above-mentioned crosslinkings may take place in a hyaluronic acid derivative molecule or between different hyaluronic acid derivative molecules.

Suppose the case where the process for preparing the hyaluronic acid derivative of the present invention comprising a step of condensing a diamine with carboxy in the glucuronic acid moiety, and only a portion (e.g., 10%) of the diamine is attached to a drug, so that unused amino remains in the hyaluronic acid derivative. Then, said amino may be treated with a dicarboxylic anhydride such as succinic anhydride, maleic anhydride, glutaric anhydride, and adipic anhydride or may be reacted with dicarboxylic acid such as maleic acid, glutaric acid and adipic acid in the presence of a condensing agent, so that the terminal functional groups can be converted back to carboxy to eliminate the cationicity of said remaining amino or render the total charge anionic. Alternatively, said amino may be treated with a carboxylic anhydride such as acetic anhydride and benzoic anhydride or may be treated with a carboxylic acid such as acetic acid and benzoic acid in the presence of a condensing agent, so that the terminal functional groups can be amidated to eliminate the cationicity of said remaining amino or render the total charge non-ionic.

The chemically-crosslinked structure of a gel of the inventive hyaluronic acid derivative may also comprise a biodegradable structure. Although the following is not exhaustive, groups having an ester linkage and methacryloyl may be used as a group subjected to a crosslinking reaction. Alternatively, a compound having an ester linkage, such as Sulfo-EGS and EDMA, or a compound having a peptide spacer that is degraded by an enzyme in the living body may be used as a crosslinking agent. Moreover, a gel crosslinked via disulfide bonds formed by oxidation of mercapto groups will be degraded in the living body via disulfide exchange reaction or reduction reaction. The presence of a degradable chemically-crosslinked structure enables control of the biodegradation rate of the gel of the inventive hyaluronic acid derivative, thereby also enabling control of the drug release rate.

The hyaluronic acid derivative of the present invention can be used as a carrier for a pharmaceutical composition. In one aspect of the present invention, a hyaluronic acid derivative comprising disaccharide units represented by Formula (I) and Formula (III), or by Formula (I), Formula (II) and Formula (III) is crosslinked using a crosslinking agent for gelation, so that the resulting gel can be used as a carrier to encapsulate a drug (low molecular weight compound, protein, peptide, or nucleic acid). The drug can be exemplified by the following.

Examples of the low molecular weight compound include, but are not limited to, carcinostatic agent (e.g., alkylating agent, antimetabolite, alkaloid), immunosuppressive agent, antiinflammatory agent (e.g., steroid, non-steroidal antiinflammatory agent), antirheumatic agent, and antibacterial agent (e.g., β-lactam antibiotic, aminoglycoside antibiotic, macrolide antibiotic, tetracycline antibiotic, new quinolone antibiotic, sulfa drug).

Examples of the protein and peptide include, but are not limited to, erythropoietin (EPO) serving as an anemia drug and an organ protection drug, granulocyte colony-stimulating factor (G-CSF) serving as a neutropenia drug, interferon-α, -β, -γ, (INF-α, -β, -γ), thrombopoietin (TPO), ciliary neurotrophic factor (CNTF), tumor necrosis factor (TNF), tumor necrosis factor binding protein (TNFbp), interleukin-10 (IL-10), EMS-like tyrosine kinase (Flt-3), growth hormone (GH), insulin, insulin-like growth factor-1 (IGF-1), platelet-derived growth factor (PDGF), interleukin-1 receptor antagonist (IL-1ra), brain-derived neurotrophic factor (BDNF), keratinocyte growth factor (KGF), stem cell factor (SCF), megakaryocyte growth and differentiation factor (MGDF), osteoprotegerin (OPG), leptin, parathyroid hormone (PTH), basic fibroblastic growth factor (b-FGF), bone morphogenetic protein (BMP), atrial natriuretic peptide (ANP), brain natriuretic peptide (BNP), C-type natriuretic peptide (CNP), glucagon-like peptide-1 ((GLP-1), various enzyme replacement drugs, antibody, diabody, minibody, fragmented antibody, and chemically modified forms thereof.

Examples of the nucleic acid include, but are not limited to, DNA, RNA, antisense, decoy, ribozyme, small interfering RNA, microRNA, RNA aptamer, and chemically modified forms thereof.

Preferred drugs are a protein, a peptide, and a nucleic acid, and the inventive composition comprising a protein, a peptide, and a nucleic acid can be obtained by encapsulating these drugs.

In another aspect of the present invention, a hyaluronic acid derivative/drug conjugate wherein one or more of the foregoing drugs are conjugated to a hyaluronic acid derivative comprising disaccharide units represented by Formula (I) is provided. The hyaluronic acid derivative that can be used in one embodiment of this aspect is a hyaluronic acid derivative comprising disaccharide units represented by Formula (I) and Formula (III), or by Formula (I), Formula (II) and Formula (III). For example, the hyaluronic acid derivative/drug conjugate can be prepared by conjugating the drug to hydroxy, amino, mercapto or a reactive carbon-carbon double bond (e.g., methacryloyl, acryloyl), which are present in the group of —NR$^e$—Y$^b$—R$^d$ in Formula (III). Some or all groups of the formula —NR$^e$—Y$^b$—R$^d$ which are converted to —NR$^x$-A-B—CO—NR$^e$—Y$^b$—R$^d$ may be present in Formula (I).

Further, there may be inserted, between the group of —NR$^e$—Y$^b$—R$^d$ and a drug, a spacer represented by the formula -G$^1$-G$^2$-G$^3$-J-***

(wherein
"***" represents a bonding position to the drug;
G$^1$ is selected from a direct bond, —C(=O)—, —NR$^s$—, and —S—;
G$^2$ is selected from and —(CH$_2$)$_i$— and —(CH$_2$)$_q$—(O—CH$_2$—CH$_2$)$_k$—;
G$^3$ is selected from a direct bond, —C(=O)—NR$^t$—(CH$_2$)$_r$—, and —NR$^u$—C(=O)—(CH$_2$)$_m$—;
J represents a group represented by the following formula:

[Formula 24]

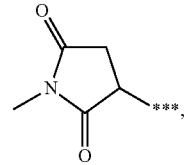

R$^s$, R$^t$ and R$^u$ are independently selected from a hydrogen atom and C$_{1-6}$ alkyl, i is an integer selected from 1 to 10, q is an integer selected from 2 to 10, k is an integer selected from 1 to 100, and r and m are independently an integer selected from 1 to 10).

Specific examples of the formula -G$^1$-G$^2$-G$^3$-J-*** include, but are not limited to, the following formulas:

[Formula 25]

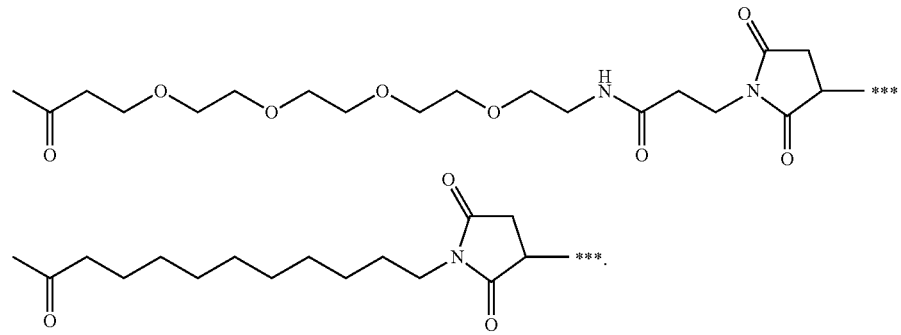

The hydroxy groups at position 4 of glucuronic acid or at position 1 of acetylglucosamine, which are present at terminal ends of the backbone of the hyaluronic acid derivative of the present invention, may be converted to different groups, and they may be, for example, C$_{1-6}$ alkoxy, formyloxy, and C$_{1-6}$ alkylcarbonyloxy.

A gel of the hyaluronic acid derivative of the present invention having a drug encapsulated therein, or a conjugate between the hyaluronic acid derivative of this invention and a drug, can be formulated into a pharmaceutical composition comprising the gel or the conjugate and one or more pharmaceutically acceptable additives such as diluents, wetting agents, emulsifying agents, dispersing agents, adjuvants, antiseptic agents, buffering agents, binding agents, stabilizing agents, so that the composition can be administered in any appropriate dosage form depending on the desired administration route. The administration route may be a parenteral or an oral route.

The present invention makes it possible to achieve a long-time sustained release of drugs such as proteins, peptides, nucleic acids, and low molecular weight compounds, which has not been achieved by conventional sustained release formulations, as well as to provide sustained release formulations and pharmaceutical compositions having appropriate biodegradability and high safety. This invention also makes it possible to provide pharmaceutical formulations and compositions that enable effective uptake of the drugs into the cytoplasm, because in the route of intracellular uptake of endocytosed drugs, the hyaluronic acid derivative of this invention has a promoting action on the release of the drugs from the endosome into the cytoplasm.

EXAMPLES

The present invention was described below using specific suitable embodiments thereof as working examples.

As used herein below, "HA unit" means a repeating unit of N-acetylglucosamine-glucuronic acid in hyaluronic acid. NMR analysis was made using a nuclear magnetic resonance spectrometer (JNM-ECA500; JEOL, Ltd). The NMR analysis conditions are as follows.

$^1$H-NMR Analysis Conditions
Data point: 16384
Spectral width (X sweep): 15 ppm
Acquisition time (X acq time): 1.749 s
Pulse delay (Relaxation delay): 30 s
Transients (Scans): 64

Example 1

Synthesis of Hyaluronic Acid Derivatives

Example 1-1

Conversion of a Cation Exchange Resin to a tetrabutylammonium (TBA) Salt

DOWEX™ 50WX-8-400 (Sigma-Aldrich) was suspended in ultrapure water, and the resin was washed with ultrapure rater about three times by decantation. An aqueous solution of 40 wt % tetrabutylammonium hydroxide (TBA-OH) (Sigma-Aldrich) was added in an amount of about 1.5 molar equivalents as calculated for the cation exchange capacity of the resin, and stirring was performed for 30 minutes. After removal of excess TBA-OH solution by decantation, washing was further repeated with excess ultrapure water, and lastly, the mixture was passed through a 0.45 μm filter, whereby a cation exchange resin converted to a TBA salt was obtained.

Example 1-2

Preparation of a TBA Salt of Hyaluronic Acid (HA-TBA)

Hyaluronic acid sodium salts (HA-Na, Shiseido Co., Ltd.) with molecular weights of 25 kDa and 99 kDa were each dissolved in ultrapure water at a concentration of 15 mg/mL. The cation exchange resin converted to a TBA salt in Example 1-1 was added in an amount of 5 molar equivalents relative to the number of moles of the HA unit (unit molecular weight, 401.3) as calculated for the ion exchange capacity of the resin. After stirring for 15 minutes, the mixture was passed through a 0.45 μm filter, and the filtrate was freeze-dried to give HA-TBA samples as a while solid.

FIG. 1 shows the $^1$H-NMR spectrum of a representative example of the products, Which was obtained by analyzing in $D_2O$ the product synthesized using 99 kDa HA-Na as a starting material. The quantitative ratio of TBA to the HA unit was calculated from the integrated value of the signal derived from acetyl in HA glucosamine (—$COCH_3$, 2.0 ppm; 3H) and the integrated value of the signals derived from four ethylenes in TBA (N($CH_2CH_2CH_2CH_3$)$_4$, 1.4, 1.7 ppm; 16H), and then the unit average molecular weight of HA-TBA was calculated from the resulting ratio. For example, the unit average molecular weight of HA-TBA synthesized using 99 kDa HA-Na as a starting material was 752.6.

Example 1-3

Synthesis of a TBA Salt of Fluorescein (FL)-Labeled HA (HA-FL/TBA)

An anhydrous DMSO solution (10 mg/mL) of HA-TBA synthesized using HA-Na (99 kDa) as a starting material in Example 1-2 was prepared. Then, 5-(aminomethyl)fluorescein hydrochloride (Invitrogen) was added in an amount of 0.05 molar equivalents relative to the HA unit. Next, 4-(4,6-dimethoxy-1,3,5-triazin-2-yl)-4-methylmorpholinium chloride (DMT-MM, Kokusan Chemical Co., Ltd.) was added in an amount of 0.2 molar equivalents relative to the HA unit, and stirring was performed at room temperature for at least 6 hours. The reaction solution was dialyzed (Spectra/Por 4, molecular weight cutoff (MWCO): 12-14 kDa) against an aqueous solution of 0.3 M NaCl and ultrapure water in this order. The suspension of cation exchange resin converted to a TBA salt in Example 1-1 was added to the resulting dialyzate in an amount of 5 molar equivalents relative to the HA unit as calculated for the ion exchange capacity of the resin. After stirring for 15 minutes, the mixture was passed through a 0.45 μm filter, and the filtrate was freeze-dried to give the product of interest (HA-FL/TBA) as a yellow solid.

FIG. 2 shows the $^1$H-NMR spectrum obtained by analyzing the product in $D_2O$. The quantitative ratio of TBA to the HA unit was calculated from the integrated value of the peak derived from acetyl in HA glucosamine (—$COCH_3$, 2.0 ppm; 3H) and the integrated value of the peak derived from four methyls TBA ((N($CH_2CH_2CH_2CH_3$)$_4$, 1.0 ppm; 12H), and then the unit average molecular weight of HA-FL/TBA was calculated from the resulting ratio. The content of HA units per weight was quantified from the integrated value of the peak derived from acetyl in glucosamine and the integrated value of the peak derived from methyl in sodium 3-(trimethylsilyl)propionate-d4 (TSP-d4) used as the internal standard material (—$Si(CH_3)_3$, 0.0 ppm; 9H). The product was dissolved in a 50 mM carbonate buffer solution (pH 9.0) at a concentration of 0.05 mg/mL, and the FL content per weight was quantified from the absorbance at 491 nm, thereby calculating the modification degree of the HA unit with FL. The modification degree with FL was in the range of 3% to 6% for each batch.

Example 1-4

Synthesis of HA Derivatives from HA-TBA or HA-FL/TBA

Example 1-4-1

Synthesis of a Derivative of HA Modified with L-Alanine (Ala) (HA-Ala/FL)

An anhydrous DMSO solution (5 mg/mL) of HA-TBA synthesized using HA-Na (99 kDa) as a starting material in Example 1-2 was prepared. Then, L-alanine ethyl ester hydrochloride (Sigma-Aldrich) and 5-(aminomethyl)fluorescein hydrochloride were respectively added in amounts of 3 and 0.15 molar equivalents relative to the HA unit. Next, DMT-MM was added in an amount of 6 molar equivalents relative to the HA unit, and stirring was performed at room temperature overnight. The reaction solution was dialyzed (Spectra/Por 4, molecular weight cutoff (MWCO): 12-14 kDa) against DMSO, an aqueous solution of 0.3 M NaCl, and ultrapure water in this order. After 2N NaOH was added to the resulting dialyzate to adjust the pH to at least 12.5, stirring was performed for an hour to perform carboxy deprotect on via ethyl ester hydrolysis. Thereafter, the mixture was neutralized with 2N HCl and further dialyzed, and then the dialyzate was freeze-dried to give HA-Ala/FL as a yellow solid.

FIG. 3-1 shows the $^1$H-NMR spectrum obtained by analyzing the product under the same conditions as described in Example 1-3. The modification degree of the HA unit with alanine was calculated from the integrated value of the peak derived from acetyl HA glucosamine (—COCH$_3$, 2.0 ppm; 3H) and the integrated value of the peak derived from methyl in alanine (—CH$_3$, 1.4 ppm; 3H) using the following equation (Table 1).

$$\text{Degree of modification (\%)} = \frac{\left(\text{Integrated value of peak from methyl in alanine}\right)/3}{\left(\text{Integrated value of peak from acetyl in } HA\right)/3} * 100 \quad \text{[Formula 26]}$$

Example 1-4-2

Synthesis of a Derivative of HA Modified with L-Serine (Ser) (HA-Ser/FL)

The same procedure as in Example 1-4-1 was performed except that L-serine ethyl ester hydrochloride (Sigma-Aldrich) was used instead of L-alanine ethyl ester hydrochloride; thereby, HA-Ser/FL was given as a yellow solid. In addition, a portion of the dialysis solution before carboxy deprotection was taken and freeze-dried for use as a sample for calculating the modification degree (HA-Ser-OEt/FL).

FIG. 3-2 shows the $^1$H-NMR spectrum obtained by analyzing the sample for modification degree calculation under the same conditions as described in Example 1-3. The modification degree of the HA unit with serine was calculated from the integrated value of the peak derived from acetyl in HA glucosamine (—COCH$_3$, 2.0 ppm; 3H) and the integrated value of the peak derived from methyl in serine ethyl ester (—CH$_3$, 1.3 ppm; 3H) using the same procedure as in Example 1-4-1 (Table 1). FIG. 3-2 also shows the $^1$H-NMR spectrum obtained by analyzing the deprotected sample under the same conditions as described in Example 1-3.

Example 1-4-3

Synthesis of a Derivative of HA Modified with L-Glutamic Acid (Glu) (HA-Glu/FL)

The same procedure as in Example 1-4-1 was performed except that L-glutamic acid diethyl ester hydrochloride (Tokyo Chemical Industry Co., Ltd.) was used instead of L-alanine ethyl ester hydrochloride; thereby, HA-Glu/FL was given as a yellow solid.

FIG. 3-3 shows the $^1$H-NMR spectrum obtained by analyzing the product under the same conditions as described in Example 1-3. The modification degree of the HA unit with glutamic acid was calculated from the integrated value of the peak derived from acetyl in HA glucosamine (—COCH$_3$, 2.0 ppm; 3H) and the integrated value of the peak derived from methylene in glutamic acid (—CH$_2$CH$_2$COOH, 2.3 ppm; 2H) using the same procedure as in Example 1-4-1 (Table 1). Since the peak derived from acetyl in HA glucosamine overlapped with the peak derived from another methylene glutamic acid (—CH$_2$CH$_2$COOH, 2.1 ppm; 2H), the value obtained by subtracting the integrated value of the peak at 2.3 ppm from that of the peaks at 1.7 to 2.2 ppm was taken as the peak derived from acetyl in HA glucosamine and used for modification degree calculation.

Example 1-4-4

Synthesis of Derivatives of HA Modified with glycine (Gly) (HA-Gly and HA-Gly/FL)

An anhydrous DMSO solution (5 mg/mL) of HA-TBA synthesized in Example 1-2, or ultrapure water/DMSO (1:3) mixed solution of HA-FL/TBA (about 4 mg/mL) synthesized in Example 1-3, was used as a starting material. Glycine ethyl ester hydrochloride (Wako Pure Chemical Industries, Ltd.) was added in an amount of 5 molar equivalents relative to the HA unit. Next, DMT-MM was added in an amount of 3 molar equivalents relative to the HA unit, and stirring was performed at room temperature overnight. The reaction solution was dialyzed (Spectra/Por 4, molecular weight cutoff (MWCO): 12-14 kDa) against an aqueous solution of 0.3 M NaCl and ultrapure water in this order. After 2N NaOH was added to the resulting dialyzate to adjust the pH to at least 12.5, stirring was performed for an hour to perform carboxy deprotection via ethyl ester hydrolysis. Thereafter, the mixture was neutralized with 2N HCl and further dialyzed, and then the dialyzate was freeze-dried to give HA-Gly as a white solid or HA-Gly/FL as a yellow solid. In addition, a portion of the dialysis solution before carboxy deprotection was taken and freeze-dried for use as a sample for calculating the modification degree (HA-Gly-OEt/FL).

FIG. 3-4 shows the $^1$H-NMR spectrum obtained by analyzing the sample for modification degree calculation under the same conditions as described in Example 1-3. The modification degree of the unit with glycine was calculated from the integrated value of the peak derived from acetyl in HA glucosamine (—COCH$_3$, 2.0 ppm; 3H) and the integrated value of the peak derived from methyl in glycine ethyl ester (—CH$_3$, 1.3 ppm; 3H) using the same procedure as in Example 1-4-1 (Table 1). FIG. 3-4 also shows the $^1$H-NMR spectrum obtained by analyzing the deprotected samples under the same conditions as described in Example 1-3.

Example 1-4-5

Synthesis of Derivatives of HA Modified with L-Valine (Val) (HA-Val and HA-Val/FL)

The same procedure as in Example 1-4-4 was performed except that L-valine ethyl ester hydrochloride (Watanabe Chemical Industries, Ltd.) was used instead of glycine ethyl ester hydrochloride; thereby, HA-Val was given as a white solid, or HA-Val/FL as a yellow solid.

FIG. 3-5 shows the $^1$H-NMR spectrum obtained by analyzing the product under the same conditions as described in Example 1-3. The modification degree of the HA unit with valine was calculated from the integrated value of the peak derived from acetyl in HA glucosamine (—COCH$_3$, 2.0 ppm; 3H) and the integrated value of the peak derived from two methyls in valine (—CH(CH$_3$)$_2$, 0.9 ppm; 6H) using the same procedure as in Example 1-4-1 (Table 1). Since the peak derived from acetyl in HA glucosamine overlapped with the peak derived from hydrogen at position 3 of valine (—CH(CH$_3$)$_2$, 2.1 ppm; 1H), the integrated value of the peak at 0.9 ppm as multiplied by ⅙ was subtracted from the integrated value of the peaks at 1.8 to 2.2 ppm, and the resulting value was taken as the peak derived from acetyl in HA glucosamine and used for modification degree calculation.

Example 1-4-6

Synthesis of Derivatives of HA Modified with L-Leucine (Leu) (HA-Leu and HA-Leu/FL)

The same procedure as in Example 1-4-4 was performed except that L-leucine ethyl ester hydrochloride (Tokyo Chemical Industry Co., Ltd.) was used instead of glycine ethyl ester hydrochloride; thereby, HA-Leu was given as a white solid, or HA-Leu/FL as a yellow solid.

FIG. 3-6 shows the $^1$H-NMR spectrum obtained by analyzing the product under the same conditions as described in Example 1-3. The modification degree of the HA unit with leucine was calculated from the integrated value of the peak derived from acetyl in HA glucosamine (—COCH$_3$, 2.0 ppm; 3H) and the integrated value of the peak derived from two methyls in leucine (—CH(CH$_3$)$_2$, 0.9 ppm; 6H) using the same procedure as in Example 1-4-1 (Table 1).

Example 1-4-7

Synthesis of Derivatives of HA Modified with L-Isoleucine (Ile) (HA-Ile and HA-Ile/FL)

The same procedure as in Example 1-4-4 was performed except that anhydrous DMSO was used as a solvent and that L-isoleucine methyl ester hydrochloride (Watanabe Chemical Industries, Ltd.) was used instead of glycine ethyl ester hydrochloride; thereby, HA-Ile was given as a white solid, or HA-Ile/FL as a yellow solid.

FIG. 3-7 shows the $^1$H-NMR spectrum obtained by analyzing the product under the same conditions as described in Example 1-3. The modification degree of the HA unit with isoleucine was calculated from the integrated value of the peak derived from acetyl in HA glucosamine (—COCH$_3$, 2.0 ppm; 3H) and the integrated value of the peak derived from two methyls in isoleucine (—CH(CH$_3$)CH$_2$CH$_3$, 0.9 ppm; 6H) using the same procedure as in Example 1-4-1 (Table 1). Since the peak derived from acetyl in HA glucosamine overlapped with the peak derived from hydrogen at position 3 of isoleucine (—CH(CH$_3$)CH$_2$CH$_3$, 1.9 ppm; 1H), the integrated value of the peak at 0.9 ppm as multiplied by ⅙ was subtracted from the integrated value of the peaks at 1.8 to 2.2 ppm, and the resulting value was taken as the peak derived from acetyl in HA glucosamine and used for modification degree calculation.

Example 1-4-8

Synthesis of Derivatives of HA Modified with L-Threonine (Thr) (HA-Thr and HA-Thr/FL)

The same procedure as in Example 1-4-4 was performed except that L-threonine methyl ester hydrochloride (Bachem) was used instead of glycine ethyl ester hydrochloride; thereby, HA-Thr was given as a white solid, or HA-Thr/FL as a yellow sot d.

FIG. 3-8 shows the $^1$H-NMR spectrum obtained by analyzing the product under the same conditions as described in Example 1-3. The modification degree of the HA unit with threonine was calculated from the integrated value of the peak derived from acetyl in HA glucosamine (—COCH$_3$, 2.0 ppm; 3H) and the integrated value of the peak derived from methyl in threonine (—CH$_3$, 1.2 ppm; 3H) using the same procedure as in Example 1-4-1 (Table 1).

Example 1-4-9

Synthesis of Derivatives of HA Modified with L-Asparatic Acid (Asp) (HA-Asp and HA-Asp/FL)

The same procedure as in Example 1-4-4 was performed except that L-asparatic acid diethyl ester hydrochloride (Watanabe Chemical Industries, Ltd.) was used instead of glycine ethyl ester hydrochloride; thereby, HA-Asp was given as a white solid, or HA-Asp/FL as a yellow solid.

FIG. 3-9 shows the $^1$H-NMR spectrum obtained by analyzing the product under the same conditions as described in Example 1-3. The modification degree of the HA unit with asparatic acid was calculated from the integrated value of the peak derived from acetyl in HA glucosamine (—COCH$_3$, 2.0 ppm; 3H) and the integrated value of the peaks derived from methylene in asparatic acid (—CH$_2$COOH, 2.7, 2.8 ppm; 2H) using the same procedure as in Example 1-4-1 (Table 1).

Example 1-4-10

Synthesis of a Derivative of HA Modified with cis-2-amino-1-cyclohexyl carboxylic acid (cACHCA) (HA-cACHCA/FL)

The same procedure as in Example 1-4-4 was performed except that cACHCA ethyl ester hydrochloride (Acros) was used instead of glycine ethyl ester hydrochloride and that carboxy deprotection was carried out using 5N NaOH at pH 13.2; thereby, HA-cACHCA/FL was given as a yellow solid.

FIG. 3-10 shows the $^1$H-NMR spectrum obtained by analyzing the product under the same conditions as described in Example 1-3. The modification degree of the HA unit with cACHCA was calculated from the integrated value of the peak derived from acetyl in HA glucosamine (—COCH$_3$, 2.0 ppm; 3H) and the integrated value of the peak derived from the cyclohexane ring in cACHCA (—CHCOO—, 2.5 ppm; 1H) using the same procedure as in Example 1-4-1 (Table 1).

Example 1-4-11

Synthesis of a Derivative of HA Modified with trans-2-amino-1-cyclohexyl carboxylic acid ethyl ester (tACHCA-OEt) (HA-tACHCA-OEt/FL)

The same procedure as in Example 1-4-4 was performed except that tACHCA-OEt hydrochloride (Acros) was used instead of glycine ethyl ester hydrochloride and that no carboxy deprotection was carried out; thereby, HA-tACHCA-OEt/FL was given as a yellow solid.

Figure 11:
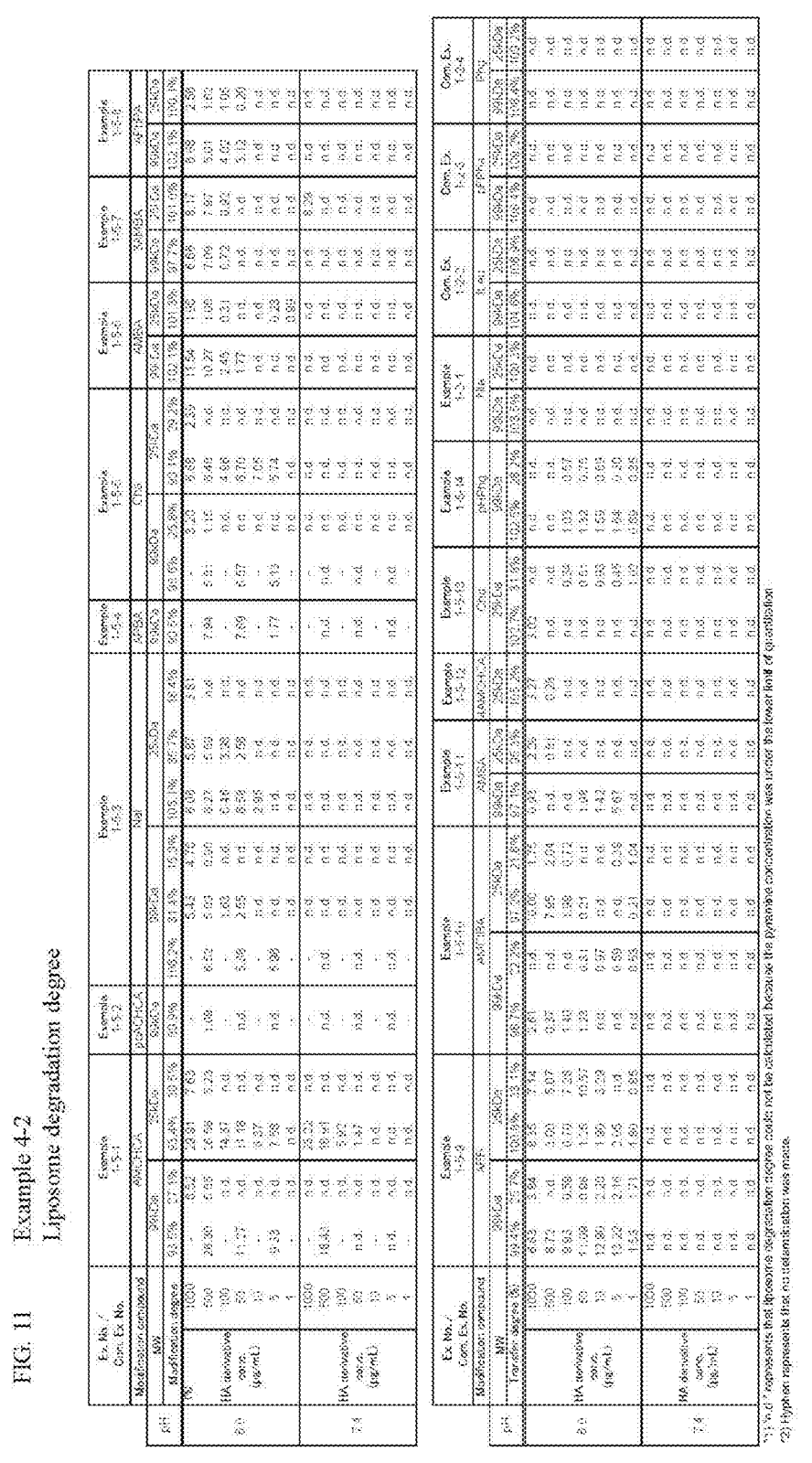

FIG. 3-11 shows the $^1$H-NMR spectrum obtained by analyzing the product under the same conditions as described in Example 1-3. The modification degree of the HA unit with tACHCA-OEt was calculated from the integrated value of the peak derived from acetyl in HA glucosamine (—COCH$_3$, 2.0 ppm; 3H) and the integrated value of the peak derived from the proton on the carbon adjacent to carbonyl on the cyclohexane ring in tACHCA-OEt (—C$\underline{H}$(COOEt)-, 2.2 ppm; 1H) using the same procedure as in Example 1-4-1 (Table 1). Since the peak derived from acetyl in HA glucosamine overlapped with the peak derived from cyclohexyl and methyl in the protecting group (11H), the integrated value of the peak at 2.2 ppm as multiplied by 11 was subtracted from the integrated value of the peaks at 1.2 to 2.1 ppm, and the resulting value was taken as the peak derived from acetyl in HA glucosamine and used for modification degree calculation.

Example 1-4-12

Synthesis of a Derivative of HA Modified with 2-aminoisobutyric acid (Aib) (HA-Aib/FL)

The same procedure as in Example 1-4-4 was performed except that Aib ethyl ester hydrochloride (Watanabe Chemical Industries, Ltd.) was used instead of glycine ethyl ester hydrochloride and that carboxy deprotection was carried out using 5N NaOH at pH 13.2; thereby, HA-Aib/FL was given as a yellow solid.

FIG. 3-12 shows the $^1$H-NMR spectrum obtained by analyzing the product under the same conditions as described in Example 1-3. The modification degree of the HA unit with Aib was calculated from the integrated value of the peak derived from acetyl in HA glucosamine (—COCH$_3$, 2.0 ppm; 3H) and the integrated value of the peak derived from dimethyl in Aib (—C(CH$_3$)$_2$—, 1.5 ppm; 6H) using the same procedure as in Example 1-4-1 (Table 1).

Example 1-4-13

Synthesis of a Derivative of HA Modified with 1-amino-1-cyclobutyric acid ethyl ester (ACBuCA-OEt) (HA-ACBuCA-OEt/FL)

The same procedure as in Example 1-4-4 was performed except that ACBuCA-OEt hydrochloride (Sigma-Aldrich) was used instead of glycine ethyl ester hydrochloride and that no carboxy deprotection was carried out; thereby, HA-ACBuCA-OEt/FL was given as a yellow solid.

FIG. 3-13 shows the $^1$H-NMR spectrum obtained by analyzing the product under the same conditions as described in Example 1-3. The modification degree of the HA unit with ACBuCA-OEt was calculated from the integrated value of the peak derived from acetyl in HA glucosamine (—COCH$_3$, 2.0 ppm; 3H) and the integrated value of the peak derived from methyl in the protecting group of ACBuCA-OEt (—CH$_3$, 1.3 ppm; 3H) using the same procedure as in Example 1-4-1 (Table 1). Since the peak derived from acetyl in HA glucosamine overlapped with the peak derived from the cyclobutane present in ACBuCA-OEt (6H), the integrated value of the peak at 1.3 ppm as multiplied by 2 was subtracted from the integrated value of the peaks at 1.8 to 2.8 ppm, and the resulting value was taken as the peak derived from acetyl in HA glucosamine and used for modification degree calculation.

Example 1-4-14

Synthesis of Derivatives of HA Modified with L-Asparagine (Asn) (HA-Asn and HA-Asn/Rh)

HA-Asn was synthesized as follows. L-asparagine methyl ester hydrochloride (Bachem) was added to an anhydrous DMSO solution (5 mg/mL) of HA-TBA synthesized using HA-Na (99 kDa) as a starting material in Example 1-2 in an amount of 5 molar equivalents relative to the HA unit. Next, DMT-MM was added in an amount of 3-6 molar equivalents relative to the HA unit, and stirring was performed at room temperature overnight. After the reaction solution was reprecipitated with diethyl ether and the precipitate was dissolved in ultrapure water, 5N NaOH solution was added to adjust the pH to at least 12.5, and stirring was performed for an hour to perform carboxy deprotection via ethyl ester hydrolysis. Thereafter, the mixture was neutralized with 5N HCl solution and further dialyzed for purification against an aqueous solution of 0.3 M NaCl, distilled water, and ultrapure water in this order, and then the dialyzate was freeze-dried to give HA-Asn as a white solid.

HA-Asn/Rh was synthesized as follows. 1-(9-fluorenylmethyloxycarbonyl-amino)-3,6-dioxa-8-octanamine hydrochloride (Fmoc-EDOBEA, Iris Biotech GmbH) was added to an anhydrous DMSO solution (5 mg/mL) of HA-TBA synthesized using HA-Na (99 kDa) as a starting material in Example 1-2 in an amount of 0.1 molar equivalents relative to the HA unit. Next, DMT-MM was added in an amount of 0.2 molar equivalents relative to the HA unit, and stirring was performed at room temperature for 6 hours. Then, L-asparagine methyl ester hydrochloride and DMT-MM were added in this order in amounts of 5 and 3-6 molar equivalents, respectively, relative to the HA unit, and stirring was performed at room temperature overnight. The reaction solution was dialyzed for purification against DMSO. Piperidine (Wako Pure Chemical Industries, Ltd.) was added to the resulting dialyzate to g a concentration of 20%, and stirring was performed for 2 hours to remove the Fmoc group. Thereafter, the mixture was dialyzed for purification against DMSO, an aqueous solution of 0.3 M NaCl, and distilled water in this order. 5N NaOH solution was added to the resulting dialyzate to adjust the pH to at least 12.5, and stirring was performed for an hour to perform ester hydrolysis and carboxy deprotection. Thereafter, the mixture was neutralized with 5N HCl solution and further dialyzed for purification against distilled water and ultrapure water in this order, and then the dialyzate was freeze-dried to give HA-Asn/EDOBEA.

An aqueous solution (10 mg/mL) of HA-Asn/EDOBEA was diluted 2-fold with 100 mM PB (pH 7.4), NHS-rhodamine (5/6-carboxytetramethylrhodamine succinimidyl ester, Thermo Fisher Scientific Inc.) was added in an amount of 0.05 molar equivalents relative to the HA unit, and stirring was performed at room temperature overnight. Then, acetic anhydride (Wako Pure Chemical Industries, Ltd.) was added in an amount of 40 molar equivalents relative to the HA unit, and stirring was performed for an hour to acetylate terminal amino in excess EDOBEA. 5N NaOH solution was added to the reaction solution to adjust the pH to at least 12.5, and stirring was performed for an hour. Thereafter, the mixture was neutralized with 5N HCl solution and dialyzed for purification against an aqueous solution of 0.3 M NaCl, distilled water, and ultrapure water in this order, and then the dialyzate was freeze-dried to give HA-Asn/Rh as a red solid.

All the dialysis membranes used were Spectra/Por 4 (molecular weight cutoff (MWCO): 12-14 kDa).

FIG. 3-14 shows the $^1$H-NMR spectrum obtained by analyzing the product under the same conditions as described in Example 1-3. The modification degree of the HA unit with asparagine was calculated from the integrated value of the peak derived from acetyl in HA glucosamine (—COCH$_3$, 2.0 ppm; 3H) and the integrated value of the peak derived from methylene in asparagine (—CH$_2$CONH$_2$, 2.8 ppm; 2H) using the same procedure as in Example 1-4-1 (Table 1).

Example 1-4-15

Synthesis of Derivatives of Modified with L-Alaninamide (Ala-NH$_2$) (HA-Ala-NH$_2$ and HA-Ala-NH$_2$/Rh)

The same procedure as in Example 1-4-14 was performed except that L-alaninamide hydrochloride (Tokyo Chemical Industry Co., Ltd) was used instead of L-asparagine methyl ester hydrochloride and that no procedure for reprecipitation or carboxy deprotection was performed; thereby, HA-Ala-NH$_2$ was given as a white solid, or HA-Ala-NH$_2$/Rh as a red solid.

FIG. 3-15 shows the $^1$H-NMR spectrum obtained by analyzing the product under same conditions as described in Example 1-3. The modification degree of the HA unit with alaninamide was calculated from the integrated value of the peak derived from acetyl in HA glucosamine (—COCH$_3$, 2.0 ppm; 3H) and the integrated value of the peak derived from methyl in alaninamide (—CH$_3$, 1.5 ppm; 3H) using the same procedure as in Example 1-4-1 (Table 1).

Example 1-4-16

Synthesis of Derivatives of HA Modified with L-Valinamide (Val-NH$_2$) (HA-Val-NH$_2$ and HA-Val-NH$_2$/Rh)

The same procedure as in Example 1-4-15 was performed except that L-valinamide hydrochloride (Tokyo Chemical Industry Co Ltd.) was used instead of L-alaninamide hydrochloride; thereby, HA-Val-NH$_2$ was given as a white solid, or HA-Val-NH$_2$/Rh as a red solid.

FIG. 3-16 shows the $^1$H-NMR spectrum obtained by analyzing the product under the same conditions as described in Example 1-3. The modification degree of the HA unit with valinamide was calculated from the integrated value of the peak derived from acetyl in HA glucosamine (—COCH$_3$, 2.0 ppm; 3H) and the integrated value of the peak derived from two methyls valinamide (—CH(CH$_3$)$_2$, 1.0 ppm; 6H) using the some procedure as in Example 1-4-1 (Table 1). Since the peak derived from acetyl in HA glucosamine overlapped with the peak derived from hydrogen at position 3 of valinamide (—CH(CH$_3$)$_2$, 2.1 ppm; 1H), the integrated value of the peak at 1.0 ppm as multiplied by ⅙ was subtracted from the integrated value of the peaks at 1.8 to 2.2 ppm, and the resulting value was taken as peak derived from acetyl in HA glucosamine and used for modification degree calculation.

Example 1-4-17

Synthesis of Derivatives of HA Modified with L-Asparaginamide (Asn-NH$_2$) (HA-Asn-NH$_2$ and HA-Asn-NH/Rh)

The same procedure as in Example 1-4-15 was performed except that L-asparaginamide hydrochloride (Kokusan Chemical Co., Ltd.) was used instead of L-alaninamide hydrochloride; thereby, HA-Asn-NH, was given as a white solid, or HA-Asn-NH$_2$/Rh as a red solid.

FIG. 3-17 shows the $^1$H-NMR spectrum obtained by analyzing the product under the same conditions as described in Example 1-3. The modification degree of the HA unit with asparaginamide was calculated from the integrated value of the peak derived from acetyl in HA glucosamine (—COCH$_3$, 2.0 ppm; 3H) and the integrated value of the peak derived from methylene in asparaginamide (—CH$_2$CONH$_2$, 2.8 ppm; 2H) using the same procedure as in Example 1-4-1 (Table 1).

Example 1-4-18

Synthesis of Derivatives of HA Modified with Methylamine (Me) (HA-Me and HA-Me/FL)

HA-Me was synthesized as follows. An anhydrous DMSO solution (5 mg/mL) of HA-TBA synthesized using HA-Na (99 kDa) as a starting material in Example 1-2 was prepared. Then, methylamine (40% methanol solution, Tokyo Chemical Industry Co., Ltd.) and BOP (Wako Pure Chemical Industries, Ltd.) were added in this order at an equivalent ratio of HA unit/BOP/methylamine=1/3/50 (mol/mol/mol), and stirring was performed at room temperature overnight. The reaction solution was dialyzed (Spectra/Por 4, molecular weight cutoff (MWCO); 12-14 kDa) against an aqueous solution of 0.3 M NaCl and ultrapure water in this order, and then the dialyzate was freeze-dried to give HA-Me as a white solid.

HA-Me/FL was synthesized as follows. An anhydrous DMSO solution (5 mg/mL) of HA-TBA synthesized using HA-Na (99 kDa) as a starting material in Example 1-2 was prepared. Then, methylamine, ethylenediamine (Sigma-Aldrich), and BOP were added in this order at an equivalent ratio of HA unit/BOP/methylamine/ethylenediamine=1/2.5/4.5/0.25 (mol/mol/mol/mol), and stirring was performed at room temperature overnight. The reaction solution was dialyzed (Spectra/Por 4, molecular weight cutoff (MWCO): 12-14 kDa) against an aqueous solution of 0.3 M NaCl and ultrapure water in this order, and then the dialyzate was freeze-dried to give an intermediate as a white solid.

Next, the resulting intermediate was dissolved in ultrapure water to give a concentration of 10 mg/mL, and then the solution was diluted 2-fold with a 100 mM phosphate buffer solution (pH 7.4) to prepare a 5 mg/mL solution, NHS fluorescein was added as a DMSO solution to this solution in an amount of 0.1 molar equivalents relative to the HA unit, and stirring was performed at room temperature for an hour. Thereafter, acetic anhydride (Wako Pure Chemical industries, Ltd.) was added in an amount of 40 molar equivalents relative to the HA unit and further stirring was performed for an hour to acetylate terminal amino in excess ethylenediamine. The reaction solution was dialyzed (Spectra/Por 4, molecular weight cutoff (MWCO): 12-14 kDa) against an aqueous solution of 0.3 M NaCl and ultrapure water in this order under shaded conditions, and then the dialyzate was freeze-dried to give HA-Me/FL as a yellow solid.

FIG. 3-18 shows the $^1$H-NMR spectra obtained by analyzing the products under the same conditions as described in Example 1-3. The modification degree of the HA unit with methyl vas calculated from the integrated value of the peak derived from acetyl in HA glucosamine (—COCH$_3$, 2.0 ppm; 3H) and the integrated value of the peak derived from methyl (—CH$_3$, 2.8 ppm; 3H) using the same procedure as in Example 1-4-1 (Table 1).

Example 1-4-19

Synthesis of Derivatives of HA Modified with Propylamine (Pr) (HA-Pr and HA-Pr/FL)

HA-Pr was synthesized as follows. An anhydrous DMSO solution (5 mg/mL) of HA-TBA synthesized using HA-Na (99 kDa) as a starting material in Example 1-2 was prepared. Then, propylamine (Sigma-Aldrich) and BOP were added in this order at an equivalent ratio of HA unit/BOP/propylamine 1/3/50 (mol/mol/mol), and stirring was performed at room temperature overnight. The reaction solution was dialyzed (Spectra/Por 4, molecular weight cutoff (MWCO): 12-14 kDa) against an aqueous solution of 0.3 M NaCl and ultrapure water in this order, and then the dialyzate was freeze-dried to give HA-Pr as a white solid.

HA-Pr/FL was synthesized as follows. An anhydrous DMSO solution (5 mg/mL) of HA-TBA synthesized using HA-Na (99 kDa) as a starting material in Example 1-2 was prepared. Then, propylamine, ethylenediamine, and BOP were added in this order at an equivalent ratio of HA unit/BOP/propylamine/ethylenediamine=1/2.5/45/2.5 (mol/mol/mol/mol), and stirring was performed at room temperature overnight. The reaction solution was dialyzed (Spectra/Por 4, molecular weight cutoff (MWCO): 12-14 kDa) against an aqueous solution of 0.3 M NaCl and ultrapure water in this order, and then the dialyzate was freeze-dried to give an intermediate as a white solid.

Next, the resulting intermediate was dissolved in ultrapure water to give a concentration of 10 mg/mL, and then the solution was diluted 2-fold with a 100 mM phosphate buffer solution (pH 7.4) to prepare a 5 mg/mL solution. NHS-fluorescein was added as a DMSO solution to this solution in an amount of 0.06 molar equivalents relative to the HA unit, and stirring was performed at room temperature for an hour. Thereafter, acetic anhydride (Wako Pure Chemical Industries, Ltd.) was added in an amount of 40 molar equivalents relative to the HA unit and further stirring was performed for an hour to acetylate terminal amino in excess ethylenediamine. The reaction solution was dialyzed (Spectra/Por 1, molecular weight cutoff (MWCO): 12-14 kDa) against an aqueous solution of 0.3 M NaCl and ultrapure water in this order under shaded conditions, and then the dialyzate was freeze-dried to give HA-Pr/FL as a yellow solid.

FIG. 3-19 shows the $^1$H-NMR spectra obtained by analyzing the products under the same conditions as described in Example 1-3. The modification degree of the HA unit with methyl vas calculated from the integrated value of the peak derived from acetyl in HA glucosamine (—COCH$_3$, 2.0 ppm; 3H) and the integrated value of the peak derived from methyl belonging to propyl (—CH$_3$, 0.9 ppm; 3H) using the same procedure as in Example 1-4-1 (Table 1).

TABLE 1

Degrees of modification of the synthesized HA derivatives (99 kDa)

| Example No. | Modification compound | Modification degree with amino-carboxylic acid derivative or alkylamine (%) |
|---|---|---|
| 1-4-1 | Ala/FL | 86 |
| 1-4-2 | Ser/FL | 89 |
| 1-4-3 | Glu/FL | 73 |
| 1-4-4 | Gly | 89 |
|  | Gly/FL | 93 |
| 1-4-5 | Val | 99 |
|  | Val/FL | 101 |
| 1-4-6 | Leu | 84 |
|  | Leu/FL | 93 |
| 1-4-7 | Ile | 100 |
|  | Ile/FL | 98 |
| 1-4-8 | Thr | 98 |
|  | Thr/FL | 99 |
| 1-4-9 | Asp | 96 |
|  | Asp/FL | 100 |
| 1-4-10 | cACHCA/FL | 82 |
| 1-4-11 | tACHCA-OEt/FL | 87 |
| 1-4-12 | Aib/FL | 80 |
| 1-4-13 | ACBuCA-OEt/FL | 98 |
| 1-4-14 | Asn | 84 |
|  | Asn/Rh | 81 |
| 1-4-15 | Ala-NH$_2$ | 93 |
|  | Ala-NH$_2$/Rh | 82 |
| 1-4-16 | Val-NH$_2$ | 97 |
|  | Val-NH$_2$/Rh | 83 |
| 1-4-17 | Asn-NH$_2$ | 91 |
|  | Asn-NH$_2$/Rh | 71 |
| 1-4-18 | Me | 101 |
|  | Me/FL | 91 |
| 1-4-19 | Pr | 108 |
|  | Pr/FL | 87 |

Example 1-5

Synthesis of HA Derivatives from HA-TBA (25 kDa or 99 kDa)

Example 1-5-1

Synthesis of Derivatives of HA Modified with 1-aminomethyl-1-cyclohexanoic acid (AMCHCA) (HA-AMCHCA)

Anhydrous DMSO solutions (10 mg/mL) of HA-TBA synthesized using HA-Na (25 kDa and 99 kDa) as a starting material in Example 1-2 were prepared, and then 1-aminomethyl-1-cyclohexanoic acid methyl ester hydrochloride (AMCHCA-OMe.HCl, Bionet Research) was added to each of the solutions at the ratio relative to the HA-TBA unit as shown in Table 2. Next, DMT-MM was added at the ratio relative to the HA-TBA unit as shown in Table 2, and stirring was performed at room temperature overnight. The reaction solution was dialyzed (Spectra/Por 4, molecular weight cutoff (MWCO): 12-14 kDa) for purification against a large excess of aqueous solution of 0.3 M NaCl. A aqueous solution of 5N NaOH was added to the resulting dialyzate to adjust the pH to at least 13.2, and stirring was performed at room temperature for an hour, and 5N HCl was further added for neutralization. Next, the mixture was dialyzed (Spectra/Por 4, MWCO: 12-14 kDa) for purification against distilled water and ultrapure water in this order, and the resulting dialyzate was freeze-dried to give the products of interest (HA-AMCHCA) as a white solid.

FIG. 4-1 shows the $^1$H-NMR spectrum of a representative example of the products, which was obtained by analyzing in D$_2$O the product synthesized using HA-Na with a MW of 99 kDa in the presence of the reagents at the ratio of HA-TBA unit/DMT-MM/AMCHCA-OMe.HCl=1/3/5. The modification degree of the HA unit with AMCHCA was calculated from the integrated value of the peak derived from acetyl in HA glucosamine (—COCH$_3$, 2.0 ppm; 3H) and the integrated value of the peaks derived from cyclohexane belonging to AMCHCA (C$_6$H$_{10}$, 1.2-1.9 ppm; 1.0H) using the same procedure as in Example 1-4-1 (Table 7).

Example 1-5-2

Synthesis of a Derivative of HA Modified with cis-4-aminocyclohexanoic acid (pcACHCA) (HA-pcACHCA)

The same procedure as in Example 1-5-1 was performed except that cis-4-amino-1 cyclohexylcarboxylic acid methyl ester hydrochloride (pcACHCA-OMe.HCl, Iris Biotech) was used instead of AMCHCA-OMe.HCl; thereby, the product of interest (HA-pcACHCA) was given as a white solid. The addition amounts of the reagents is shown in Table 2.

As a representative example, FIG. 4-2 shows the $^1$H-NMR spectrum obtained by analyzing in D$_2$O the product synthesized using HA-Na with a MW of 99 kDa in the presence of the reagents at the ratio of HA-TBA unit/DMT-MM/pcACHCA-OMe.HCl=1/3/5. The modification degree of the HA unit with pcACHCA was calculated from the integrated value of the peak derived from acetyl in HA glucosamine (—COCH$_3$, 2.0 ppm; 3H) and the integrated value of the peaks derived trot ethylenes present in cyclohexane belonging to pcACHCA (1.5-1.8 ppm; 5H) using the same procedure as in Example 1-4-1 (Table 2).

Example 1-5-3

Synthesis of Derivatives of HA Modified with L-2-naphthylalanine (Nal) (HA-Nal)

The same procedure as in Example 1-5-1 was performed except that L-2-naphthylalanine benzyl ester para-tosylate salt (Nal-Obzl.p-Ts, Bachem) was used instead of AMCHCA-OMe.HCl; thereby, the products of interest (HA-Nal) were given as a white solid. The addition ratios of the reagents are shown in Table 2.

FIG. 4-3 shows the $^1$H-NMR spectrum of a representative example of the products, Which was obtained by analyzing in D$_2$O the product synthesized using HA-Na with a MW of 99 kDa in the presence of the reagents at the ratio of HA-TBA unit/DMT-MM/Nal-Obzl.p-Ts=1/3/5. The modification degree of the HA unit with Nal was calculated from the integrated value of the peak derived from acetyl in HA glucosamine (—COCH$_3$, 2.0 ppm; 3H) and the integrated value of the peaks derived from naphthyl belonging to Nal (—C$_{10}$H$_7$, 7.4-7.9 ppm; 7H) using the same procedure as in Example 1-4-1 (Table 2).

Example 1-5-4

Synthesis of a Derivative of HA Modified with 2-amino-4-phenylbutyric acid (APBA) (HA-APBA)

The same procedure as in Example 1-5-1 was performed except that 2-amino-4-phenylbutyric acid ethyl ester hydrochloride (APBA-OEt.HCl, Sigma-Aldrich) was used instead of AMCHCA-OMe.HCl; thereby, the product of interest (HA-APBA) was given as a white solid. The addition ratio of the reagents is shown in Table 2.

FIG. 4-4 shows the $^1$H-NMR spectrum obtained by analyzing in D$_2$O the product synthesized using HA-Na with a MW of 99 kDa in the presence of the reagents at the ratio of HA-TBA unit/DMT-MM/APBA-OEt.HCl=1/3/5. The modification degree of the HA unit with APBA was calculated from the integrated value of the peak derived from acetyl in HA glucosamine (—COCH$_3$, 2.0 ppm; 3H) and the integrated value of the peaks derived from phenyl belonging to APBA (—C$_6$H$_5$, 7.2-7.4 ppm; 514) using the same procedure as in Example 1-4-1 (Table 2).

Example 1-5-5

Synthesis of Derivatives of HA Modified with cyclohexyl-L-alanine (Cha) (HA-Cha)

The same procedure as in Example 1-5-1 was performed except that cyclohexyl L alanine methyl ester hydrochloride (Cha-OMe.HCl, Watanabe Chemical Industries, Ltd.) was used instead of AMCHCA-OMe.HCl; thereby, the products of interest (HA-Cha) were given as a white solid. The addition ratios of the reagents are shown in Table 2.

FIG. 4-5 shows the $^1$H-NMR spectrum of a representative example of the products, which was obtained by analyzing in D$_2$O the product synthesized using HA-Na with a MW of 99 kDa in the presence of the reagents at the ratio of HA-TBA unit/DMT-MM/Cha-OMe.HCl=1/3/5. The modification degree of the HA unit with Cha was calculated from the integrated value of the peak derived from acetyl in HA glucosamine (—COCH$_3$, 2.0 ppm; 3H) and the integrated value of the peaks derived from cyclohexylmethyl belonging to Cha (—CH$_2$C$_6$H$_{11}$, 0.9-1.8 ppm; 13H) using the same procedure as in Example 1-4-1 (Table 2).

Example 1-5-6

Synthesis of Derivatives of HA Modified with 4-aminomethylbenzoic acid (AMBA) (HA-AMBA)

The same procedure as in Example 1-5-1 was performed except that 4-aminomethylbenzoic acid methyl ester hydrochloride (AMBA-OMe.HCl, Sigma-Aldrich) was used instead of AMCHCA-OMe.HCl; thereby, the products of interest (HA-AMBA) were given as a white solid. The addition ratios of the reagents are shown in Table 2, FIG. 4-6 shows the $^1$H-NMR spectrum of the product. The modification degree of the HA unit with AMBA was calculated from the integrated value of the peak derived from acetyl in glucosamine (—COCH$_3$, 2.0 ppm; 3H) and the integrated value of the peaks derived from phenyl belonging to AMBA (—CH$_2$C$_6$H$_4$COOH, 7.4, 7.9 ppm; 41-1) using the same procedure as in Example 1-4-1 (Table 2).

Example 1-5-7

Synthesis of Derivatives of HA Modified with 3-aminomethylbenzoic acid (3AMBA) (HA-3AMBA)

The same procedure as in Example 1-5-1 was performed except that 3-aminomethylbenzoic acid methyl ester hydrochloride (AMBA-OMe.HCl; Fluorochem) was used instead of AMCHCA-OMe.HCl; thereby, the products of interest (HA-3AMBA) were given as a white solid. The addition ratios of the reagents are shown in Table 2.

FIG. 4-7 shows the $^1$H-NMR spectrum of a representative example of the products, which was obtained by analyzing in D$_2$O the product synthesized using HA-Na with a MW of 99 kDa in the presence of the reagents at the ratio of HA-TBA unit/DMT-MM/3AMBA-OMe.HCl=1/3/5. The modification degree of the HA unit with 3AMBA was calculated from the integrated value of the peak derived from acetyl in HA glucosamine (—COCH$_3$, 2.0 ppm; 3H) and the integrated value of the peaks derived flora phenyl belonging to 3AMBA (—C$_6$H$_4$COOH, 7.4-7.9 ppm; 4H) using the same procedure as in Example 1-4-1 (Table 7).

Example 1-5-8

Synthesis of Derivatives of HA Modified with 3-amino-2-phenylpropionic acid (APhPA) (HA-APhPA)

The same procedure as in Example 1-5-1 was performed except that 3-amino-2-phenylpropionic acid ethyl ester hydrochloride (APhPA-OEt.HCl, Tyger) was used instead of AMCHCA-OMe.HCl; thereby, the products of interest (HA-APhPA) were given as a white solid. The addition ratios of the reagents are shown in Table 2.

FIG. 4-8 shows the $^1$H-NMR spectrum of a representative example of the products, which was obtained by analyzing in D$_2$O the product synthesized using HA-Na with a MW of 99 kDa in the presence of the reagents at the ratio of HA-TBA unit/DMT-MM/APhPA-OEt.HCl=1/3/5. The modification degree of the HA unit with APhPA was calculated from the integrated value of the peak derived from acetyl in HA glucosamine (—COCH$_3$, 2.0 ppm; 3H) and the integrated value of the peak derived from phenyl belonging to APhPA (—C$_6$H$_5$, 7.4 ppm; 5H) using the same procedure as in Example 1-4-1 (Table 2).

Example 1-5-9

Synthesis of Derivatives of HA Modified with 4-(2-aminoethyl)benzoic acid (AEBA) (HA-AEBA)

The same procedure as in Example 1-5-1 was performed except that 4-(2-aminoethyl)benzoic acid methyl ester hydrochloride (AEBA-OMe.HCl, Enamine) was used instead of AMCHCA-OMe.HCl; thereby, the products of interest (HA-AEBA) were given as a white solid. The addition ratios of the reagents are shown in Table 2.

FIG. 4-9 shows the $^1$H-NMR spectrum of a representative example of the products, which was obtained by analyzing in D$_2$O the product synthesized using HA-Na with a MW of 99 kDa in the presence of the reagents at the ratio of HA-TBA unit/DMT-MM/APhPA-OEt.HCl=1/3/5. The modification degree of the HA unit with AEBA was calculated from the integrated value of the peak derived from acetyl in HA glucosamine (—COCH$_3$, 2.0 ppm; 3H) and the integrated value of the peaks derived from phenyl belonging to AEBA (—C$_6$H$_4$COOH, 7.3, 7.9 ppm; 4H) using the same procedure as in Example 1-4-1 (Table 2).

Example 1-5-10

Synthesis of Derivatives of HA Modified with 4-aminomethyl-3-chlorobenzoic acid (AMClBA) (HA-AMClBA)

The same procedure as in Example 1-5-1 was performed except that 4-aminomethyl-3-chlorobenzoic acid methyl ester hydrochloride (AMClBA-OMe.HCl, Anichem) was used instead of AMCHCA-OMe.HCl; thereby, the products of interest (HA-AMClBA) were given as a white solid. The addition ratios of the reagents are shown in Table 2.

FIG. 4-10 shows the $^1$H-NMR spectrum of a representative example of the products, which was obtained by analyzing in D$_2$O the product synthesized using HA-Na with a MW of 99 kDa in the presence of the reagents at the ratio of HA-TBA unit/DMT-MM/AMClBA-OMe.HCl=1/3/5. The modification degree of the HA unit with AMClBA was calculated from the integrated value of the peak derived from acetyl in HA glucosamine (—COCH$_3$, 2.0 ppm; 3H) and the integrated value of the peaks derived from phenyl belonging to AMClBA (—C$_6$H$_3$(Cl)COOH, 7.5, 7.8, 7.9 ppm; 314) using the same procedure as in Example 1-4-1 (Table 2).

Example 1-5-11

Synthesis of Derivatives of HA Modified with 5-aminomethylsalicylic acid (AMSA) (HA-AMSA)

The same procedure as in Example 1-5-1 was performed except that 5-aminomethylsalicylic acid methyl ester hydrochloride (AMSA-OMe.HCl, Oakwood) was used instead of AMCHCA-OMe.HCl; thereby, the products of interest (HA-AMSA) were given as a white solid. The addition ratios of the reagents are shown in Table 2.

FIG. 4-11 shows the $^1$H-NMR spectrum of a representative example of the products, which was obtained by analyzing in D$_2$O the product synthesized using HA-Na with a MW of 99 kDa in the presence of the reagents at the ratio of HA-TBA unit/DMT-MM/AMSA-OMe.HCl=1/3/5. The modification degree of the HA unit with AMSA was calculated from the integrated value of the peak derived from acetyl n HA glucosamine (—COCH$_3$, 2.0 ppm; 3H) and the integrated value of the peaks derived from phenyl belonging to AMSA (—C$_6$H$_3$(OH)COOH, 6.9-7.9 ppm; 3H) using the same procedure as in Example 1-4-1 (Table 2).

Example 1-5-12

Synthesis of a Derivative of HA Modified with trans-4-aminomethylcyclohexanoic acid (4AMCHCA) (HA-4AMCHCA)

The same procedure as in Example 1-5-1 was performed except that trans-4-aminomethylcyclohexanoic acid methyl ester hydrochloride (4AMCHCA-OMe.HCl, AK Scientific) was used instead of AMCHCA-OMe.HCl; thereby, the product of interest (HA-4AMCHCA) was given as a white solid. The addition ratio of the reagents is shown in Table 2.

FIG. 4-12 shows the $^1$H-NMR spectrum obtained by analyzing in DA) the product synthesized using HA-Na with a MW of 25 kDa in the presence of the reagents at the ratio of HA-TBA unit/DMT-MM/4AMCHCA-OMe.HCl=1/3/5. The modification degree of the HA unit with 4AMCHCA was calculated from the integrated value of the peak derived from acetyl in HA glucosamine (—COCH$_3$, 2.0 ppm; 3H) and the integrated value of the peaks derived from cyclohexane belonging to 4AMCHCA (—CH$_2$CH(CH$_2$CH$_2$)$_2$CH—, 1.2-1.9 ppm; 9H) using the same procedure as in Example 1-4-1 (Table 2).

Example 1-5-13

Synthesis of Derivatives of HA Modified with L-cyclohexylglycine (Chg) (HA-Chg)

The same procedure as in Example 1-5-1 was performed except that L-cyclohexylglycine methyl ester hydrochloride (Chg-OMe.HCl, INDOFINE Chemical Company) was used instead of AMCHCA-OMe.HCl; thereby, the products of interest (HA-Chg) were given as a white solid. The addition ratios of the reagents are shown in Table 2.

FIG. 4-13 shows the $^1$H-NMR spectrum of a representative example of the products, which was obtained by analyzing in D$_2$O the product synthesized using HA-Na with a MW of 25 kDa in the presence of the reagents at the ratio of HA-TBA unit/DMT-MM/Chg-OMe.HCl=1/3/5. The modification degree of the HA unit with Chg was calculated from the integrated value of the peak derived from acetyl in HA glucosamine (—COCH$_1$, 2.0 ppm; 3H) and the integrated value of the peaks derived from cyclohexyl belonging to Chg (—C$_6$H$_{11}$, 1.0-1.8 ppm; 11H) using the same procedure as in Example 1-4-1 (Table 2).

Example 1-5-14

Synthesis of Derivatives of HA Modified with (R)-amino-(4-hydroxyphenyl)acetic acid (pHPhg) (HA-pHPhg)

The same procedure as in Example 1-5-1 was performed except that (R)-amino-(4-hydroxyphenyl)acetic acid methyl ester hydrochloride (pHPhg-OMe.HCl, Sigma-Aldrich) was used instead of AMCHCA-OMe.HCl; thereby, the products of interest (HA-pHPhg) were given as a white solid. The addition ratios of the reagents are shown in Table 2.

FIG. 4-14 shows the $^1$H-NMR spectrum of a representative example of the products, which was obtained by analyzing in D$_2$O the product synthesized using HA-Na with a MW of 99 kDa in the presence of the reagents at the ratio of HA-TBA unit/DMT-MM/pHPhg-OMe.HCl=1/3/5. The modification degree of the HA unit with pHPhg was calculated from the integrated value of the peak derived from acetyl in HA glucosamine (—COCH$_3$, 2.0 ppm; 3H) and the integrated value of the peaks derived from phenyl belonging to pHPhg (—C$_6$H$_4$OH, 6.9, 7.3 ppm; 4H) using the same procedure as in Example 1-4-1 (Table 2).

TABLE 2

Amounts of the reagents used to synthesize HA derivatives, and synthesis results

| Example No. | Modification compound | HA molecular weight | Molar addition ratio of modification compound and DMT-MM (HA-TBA unit/DMT-MM/modification compound) | Modification degree (%) |
|---|---|---|---|---|
| 1-5-1 | AMCHCA | 99 kDa | 1/3/5 | 94 |
|  | AMCHCA | 99 kDa | 1/0.33/5 | 27 |
|  | AMCHCA | 25 kDa | 1/3/5 | 93 |
|  | AMCHCA | 25 kDa | 1/0.33/5 | 31 |
| 1-5-2 | pcACHCA | 99 kDa | 1/3/5 | 90 |
| 1-5-3 | NaI | 99 kDa | 1/3/5 | 106 |
|  | NaI | 99 kDa | 1/0.55/5 | 31 |
|  | NaI | 99 kDa | 1/0.33/5 | 16 |
|  | NaI | 25 kDa | 1/3/5 | 105 |
|  | NaI | 25 kDa | 1/0.55/5 | 36 |
|  | NaI | 25 kDa | 1/0.33/5 | 18 |
| 1-5-4 | APBA | 99 kDa | 1/3/5 | 99 |
| 1-5-5 | Cha | 99 kDa | 1/3/5 | 99 |
|  | Cha | 99 kDa | 1/0.33/5 | 26 |
|  | Cha | 25 kDa | 1/3/5 | 99 |
|  | Cha | 25 kDa | 1/0.33/5 | 29 |
| 1-5-6 | AMBA | 99 kDa | 1/3/5 | 102 |
|  | AMBA | 25 kDa | 1/3/5 | 101 |
| 1-5-7 | 3AMBA | 99 kDa | 1/3/5 | 100 |
|  | 3AMBA | 25 kDa | 1/3/5 | 101 |
| 1-5-8 | APhPA | 99 kDa | 1/3/5 | 101 |
|  | APhPA | 25 kDa | 1/3/5 | 100 |
| 1-5-9 | AEB | 99 kDa | 1/3/5 | 99 |
|  | AEB | 99 kDa | 1/0.33/5 | 26 |
|  | AEB | 25 kDa | 1/3/5 | 101 |
|  | AEB | 25 kDa | 1/0.33/5 | 33 |
| 1-5-10 | AMClBA | 99 kDa | 1/3/5 | 99 |
|  | AMClBA | 99 kDa | 1/0.33/5 | 22 |
|  | AMClBA | 25 kDa | 1/3/5 | 97 |
|  | AMClBA | 25 kDa | 1/0.33/5 | 22 |
| 1-5-11 | AMSA | 99 kDa | 1/3/5 | 97 |
|  | AMSA | 25 kDa | 1/3/5 | 95 |
| 1-5-12 | 4AMCHCA | 25 kDa | 1/3/5 | 105 |
| 1-5-13 | Chg | 25 kDa | 1/3/5 | 103 |
|  | Chg | 25 kDa | 1/0.33/5 | 32 |
| 1-5-14 | pHPhg | 99 kDa | 1/3/5 | 103 |
|  | pHPhg | 99 kDa | 1/0.33/5 | 28 |

Comparative Example 1-1

Synthesis of FL-Labeled HA Derivatives from HA-TBA or HA-FL/TBA

Comparative Example 1-1-1

Synthesis of a FL-Labeled HA (HA-FL)

An anhydrous DMSO solution (5 mg/mL) of HA-TBA synthesized using HA-Na (99 kDa) as a starting material in Example 1-2 was prepared. Then, 2,2'-(ethylenedioxy)bis (ethylamine) (EDOBEA, Sigma-Aldrich) and BOP (Wako Pure Chemical Industries, Ltd.) were added in this order at an equivalent ratio of HA unit/BOP/EDOBEA=Jan. 2, 1950 (mol/mol/mol), and stirring was performed at room temperature overnight. The reaction solution was dialyzed (Spectra/Por 4, molecular weight cutoff (MWCO): 12-14 kDa) against an aqueous solution of 0.3 M NaCl and ultrapure water in this order, and then the dialyzate was freeze-dried to give HA-EDOBEA with a low modification degree.

FIG. 5-1 shows the $^1$H-NMR spectrum obtained by analyzing HA-EDOBEA with a low modification degree under the same conditions as described in Example 1-3. The modification degree of the HA unit with EDOBEA was calculated from the integrated value of the peak derived from acetyl in HA glucosamine (—COCH$_3$, 2.0 ppm; 3H) and the integrated value of the peak derived from terminal methylene in EDOBEA (—CH$_2$NH$_2$, 3.2 ppm; 2H) using the same procedure as in Example 1-3 (Table 3).

Next, the resulting HA-EDOBEA with a low modification degree was dissolved in ultrapure water to give a concentration of 10 mg/mL, and then the solution was diluted 2-fold with a 100 mM phosphate buffer solution (pH 74) to prepare a 5 mg/mL solution. NHS-fluorescein (5/6-carboxyfluorescein succinimidyl ester, NHS-FL, PIERCE) was added as a DMSO solution to this solution in an amount of 0.1 molar equivalents relative to the HA unit, and stirring was performed at room temperature for an hour. Thereafter, succinic anhydride (Wako Pure Chemical Industries, Ltd.) was added as a DMSO solution in an amount of 40 molar equivalents relative to the HA unit and further stirring was performed for an hour to treat terminal amino in excess EDOBEA with succinic acid. The reaction solution was dialyzed (Spectra/Por 4, molecular weight cutoff (MWCO): 12-14 kDa) against an aqueous solution of 0.3 M NaCl and ultrapure rate in this order under shaded conditions, and then the dialyzate was freeze-dried to give HA-FL (HA with a low modification degree) as a yellow solid.

FIG. 5-1 also shows the $^1$H-NMR spectrum obtained by analyzing this product under the same conditions as described in Example 1-3.

The product was dissolved in a 50 mM carbonate buffer solution (pH 9.0) at a concentration of 0.05 mg/mL, and the FL content per weight was quantified from the absorbance at 491 nm, thereby calculating the modification degree of the HA unit with FL (Table 3).

Comparative Example 1-1-2

Synthesis of a Derivative of HA Modified with EDOBEA (HA-EDOBEA-Ac/FL)

The same procedure as in Comparative Example 1-1-1 was performed except that the reagents were added at a ratio of HA unit/BOP/EDOBEA 1/2.5/50 (mol/mol/mol); thereby, HA-EDOBEA with a high modification degree was obtained.

FIG. 5-2 shows the $^1$H-NMR spectrum obtained by analyzing HA-EDOBEA with a high modification degree under the same conditions as described in Example 1-3. For analyzing the solution, NaOD was added at a concentration of 0.0046N so as to make the solution alkaline. The modification degree of the HA unit with EDOBEA was calculated from the integrated value of the peak derived from acetyl in HA glucosamine 2.0 ppm; 3H) and the integrated value of the peak derived from terminal methylene in EDOBEA (—CH$_2$NH$_2$, 2.8 ppm; 2H) using the same procedure as in Example 1-3 (Table 3).

Next, the resulting HA-EDOBEA with a high modification degree was dissolved in ultrapure water to give a concentration of 10 mg/mL, and then the solution was diluted 2-fold with a 100 mM phosphate buffer solution (pH 7.4) to prepare a 5 mg/mL solution. NHS-fluorescein was added as a DMSO solution to this solution in an amount of 0.04 molar equivalents relative to the HA unit, and stirring was performed at room temperature for an hour. Thereafter, acetic anhydride (Wako Pure Chemical Industries, Ltd.) was added in an amount of 40 molar equivalents relative to the HA unit and further stirring was performed for an hour to acetylate terminal amino in excess EDOBEA. The reaction solution was dialyzed (Spectra/Por 4, molecular weight cutoff (MWCO): 12-14 kDa) against an aqueous solution of 0.3 M NaCl and ultrapure water in this order under shaded conditions, and then the dialyzate was freeze-dried to give HA-EDOBEA-Ac/FL as a yellow solid.

FIG. 5-2 also shows the $^1$H-NMR spectrum obtained by analyzing this product under the same conditions as described in Example 1-3. The modification degree of the HA unit of this product with FL was determined by the same procedure as in Comparative Example 1-1-1 (Table 3).

TABLE 3

Amounts of the reagents used to synthesize HA derivatives, and synthesis results

| Com. Ex. No. | Product of interest | Addition ratio of the reagents used to synthesize HA-EDOBEA (HA unit/BOP/EDOBEA) | Modification degree with EDOBEA (%) | Modification degree with FL (%) |
|---|---|---|---|---|
| 1-1-1 | HA-FL | 1/0.2/50 | 13 | 7 |
| 1-1-2 | HA-EDOBEA-Ac/FL | 1/2.5/50 | 82 | 3 |

Comparative Example 1-1-3

Synthesis of a Derivative of HA Modified with L-phenylalanine (Phe) (HA-Phe/FL)

The same procedure as in Example 1-4-1 was performed except that L-phenylalanine ethyl ester hydrochloride (Sigma-Aldrich) was used instead of L-alanine ethyl ester hydrochloride; thereby, HA-Phe/FL was given as a yellow solid.

FIG. 5-3 shows the $^1$H-NMR spectrum obtained by analyzing this product under the same conditions as described in Example 1-3. The modification degree of the HA unit with phenylalanine was calculated from the integrated value of the peak derived from acetyl in HA glucosamine (—COCH$_3$, 2.0 ppm; 3H) and the integrated value of the peaks derived from phenyl in phenylalanine (—C$_6$H$_5$, 7.2-7.4 ppm; 5H) using the same procedure as in Example 1-4-1 (Table 4).

Comparative Example 1-1-4

Synthesis of a Derivative of HA Modified with L-thyrosine (Tyr) (HA-Tyr/FL)

The same procedure as in Example 1-4-4 was performed except that L-thyrosine ethyl ester hydrochloride (Wako Pure Chemical Industries, Ltd.) was used instead of glycine ethyl ester hydrochloride; thereby, HA-Tyr/FL was given as a yellow solid.

FIG. 5-4 shows the $^1$H-NMR spectrum obtained by analyzing the product under the same conditions as described in Example 1-3. The modification degree of the HA unit with thyrosine was calculated from the integrated value of the peak derived from acetyl in HA glucosamine (—COCH$_3$, 2.0 ppm; 3H) and the integrated value of the peaks derived from hydroxyphenyl in thyrosine (—C$_6$H$_4$OH, 6.8, 7.2 ppm; 4H) using the same procedure as in Example 1-4-1 (Table 4).

Comparative Example 1-1-5

Synthesis of a Derivative of HA Modified with α-methyl-DL-phenylalanine (MePhe) (HA-MePhe/FL)

The same procedure as in Example 1-4-4 was performed except that MePhe methyl ester hydrochloride (Watanabe Chemical Industries, Ltd.) was used instead of glycine ethyl ester hydrochloride and that carboxy deprotection was carried out using 5N NaOH at pH 13.2; thereby, HA-MePhe/FL was given as a yellow solid.

FIG. 5-5 shows the $^1$H-NMR spectrum obtained by analyzing the product under the same conditions as described in Example 1-3. The modification degree of the HA unit with MePhe was calculated from the integrated value of the peak derived from acetyl in HA glucosamine (—$COCH_3$, 2.0 ppm; 3H) and the integrated value of the peak derived from methyl in MePhe (—$CH_3$, 1.5 ppm; 3H) using the same procedure as in Example 1-4-1 (Table 4).

Comparative Example 1-1-6

Synthesis of a Derivative of HA Modified with
L-proline methyl ester (Pro-OMe)
(HA-Pro-OMe/FL)

The same procedure as in Example 1-4-4 was performed except that Pro-OMe hydrochloride (Sigma-Aldrich) was used instead of glycine ethyl ester hydrochloride and that no carboxy deprotection was carried out; thereby, HA-Pro-OMe/FL was given as a yellow solid.

FIG. 5-6 shows the $^1$H-NMR spectrum obtained by analyzing the product under the same conditions as described in Example 1-3. The modification degree of the HA unit with Pro-OMe was calculated from the integrated value of the peak derived from acetyl in HA glucosamine (—$COCH_3$, 2.0 ppm; 3H) and the integrated value of the peak for 1H derived from the pyrrolidine ring in Pro-OMe (—CHCOO—, 2.4 ppm; 1H) using the same procedure as in Example 1-4-1 (Table 4). Since the peak derived from acetyl in HA glucosamine overlapped with the peaks for the other hydrogens on the pyrrolidine group (3H), the integrated value of the peak at 2.4 ppm as multiplied by 3 was subtracted from the integrated value of the peaks at 1.8 to 2.2 ppm, and the resulting value was taken as the peak derived from acetyl in HA glucosamine and used for modification degree calculation.

Comparative Example 1-1-7

Synthesis of Derivatives of HA Modified with
glysinamide (Gly-$NH_2$) (HA-Gly-$NH_2$ and
HA-Gly-$NH_2$/Rh)

The same procedure as in Example 1-4-15 was performed except that glycinamide hydrochloride (Watanabe Chemical Industries, Ltd.) was used instead of L-alaninamide hydrochloride; thereby, HA-Gly-$NH_2$ was given as a white solid, or HA-Gly-$NH_2$/Rh as a red solid.

FIG. 5-7 shows the $^1$H-NMR spectrum obtained by analyzing the product under the same conditions as described in Example 1-3. The modification degree of the HA unit with glycinamide was calculated from the integrated value of the peak derived from acetyl in HA glucosamine (—$COCH_3$, 2.0 ppm; 3H) and the integrated value of the peak derived from methylene in glycinamide (—$CH_2$—; 2H) using the same procedure as in Example 1-4-1 (Table 4). Since the peak derived from methylene in glycinamide overlapped with the peaks for positions 2-5 of glucuronic acid (4H), those for positions 2-6 of glucosamine (6H), and those derived from EDOBEA (12H), the integrated value of the peak at 2.0 ppm as multiplied by 10/3 as well as the integrated value of the peak at 2.0 ppm as multiplied by (EDOBEA modification degree) times 12/3 were subtracted from the integrated value of the peaks at 3.2 to 4.2 ppm, and the resulting value was taken as the peak derived from methylene in glycinamide and used for modification degree calculation. The EDOBEA modification degree was calculated by the same procedure as in Comparative Example 1-1-2.

Comparative Example 1-1-8

Synthesis of Derivatives of HA Modified with
L-serinamide (Ser-$NH_2$) (HA-Ser-$NH_2$ and
HA-Ser-$NH_2$/Rh)

The same procedure as in Example 1-4-15 was performed except that L-serinamide hydrochloride (Watanabe Chemical Industries, Ltd.) was used instead of L-alaninamide hydrochloride; thereby, HA-Ser-$NH_2$ was given as a white solid, or HA-Ser-$NH_2$/Rh as a red solid.

FIG. 5-8 shows the $^1$H-NMR, spectrum Obtained by analyzing the product under the same conditions as described in Example 1-3. The modification degree of the HA unit with serinamide was calculated from the integrated value of the peak derived from acetyl in HA glucosamine (—$COCH_3$, 2.0 ppm; 3H) and the integrated value of the peak derived from methylene in serinamide (—$CH_2$—; 2H) using the same procedure as in Example 1-4-1 (Table 4). Since the peak derived from methylene in serinamide overlapped with the peaks for positions 2-5 of glucuronic acid (4H), those for positions 2-6 of glucosamine (6H), and those derived from EDOBEA (12H), the integrated value of the peak derived from methylene in serinamide was calculated by the same procedure as in Comparative Example 1-1-7.

Comparative Example 1-1-9

Synthesis of Derivatives of HA Modified with
L-leucinamide (Leu-$NH_2$) (HA-Leu-$NH_2$ and
HA-Leu-$NH_2$/Rh)

The same procedure as in Example 1-4-15 was performed except that L-leucinamide hydrochloride (Tokyo Chemical Industry Co., Ltd.) was used instead of L-alaninamide hydrochloride; thereby, HA-Leu-$NH_2$ was given as a white solid, or HA-Leu-$NH_2$/Rh as a red solid.

FIG. 5-9 shows the $^1$H-NMR spectrum obtained by analyzing the product under the same conditions as described in Example 1-3. The modification degree of the HA unit with leucinamide was calculated from the integrated value of the peak derived from acetyl in HA glucosamine (—$COCH_3$, 2.0 ppm; 3H) and the integrated value of the peak derived from two methyls in leucinamide (—$CH(CH_3)_2$, 0.9 ppm; 6H) using the same procedure as in Example 1-4-1 (Table 4).

Comparative Example 1-1-10

Synthesis of Derivatives of HA Modified with
L-isoleucinamide (Ile-$NH_2$) (HA-Ile-$NH_2$ and
HA-Ile-$NH_2$/Rh)

The same procedure as in Example 1-4-15 was performed except that L-isoleucinamide hydrochloride (Tokyo Chemical Industry Co., Ltd.) was used instead of L-alaninamide hydrochloride; thereby, HA-Ile $NH_2$ was given as a white solid, or HA-Ile-$NH_2$/Rh as a red solid.

FIG. 5-10 shows the $^1$H-NMR spectrum obtained by analyzing the product under the same conditions as described in Example 1-3. The modification degree of the HA unit with L-isoleucinamide was calculated from the integrated value of the peak derived from acetyl in HA glucosamine (—$COCH_3$, 2.0 ppm; 3H) and the integrated value of the peak derived from two methyls in isoleucinamide (—$CH(CH_3)CH_2CH_3$, 0.9 ppm; 6H) using the same procedure as in Example 1-4-1 (Table 4). Since the peak derived from acetyl in HA glucosamine overlapped with the peak for the hydrogen at position 3 of isoleucinamide (—CH(CH₃)CH₂CH₃, 1.9 ppm; 1H), the integrated value of the peak at 0.9 ppm as multiplied by ⅙ was subtracted from the integrated value of the peaks at 1.8 to 2.2 ppm, and the resulting value was taken as the peak derived from acetyl in HA glucosamine and used for modification degree calculation.

Comparative Example 1-1-11

Synthesis of Derivatives of HA Modified with L-threoninamide (Thr-NH₂) (HA-Thr-NH₂ and HA-Thr-NH₂/Rh)

The same procedure as in Example 1-4-15 was performed except that L-threoninamide hydrochloride (Watanabe Chemical Industries, Ltd.) was used instead of L-alaninamide hydrochloride; thereby, HA-Thr-NH₂ was given as a white solid, or HA-Thr-NH₂/Rh as a red solid.

FIG. 5-11 shows the ¹H-NMR spectrum obtained by analyzing the product under the same conditions as described in Example 1-3. The modification degree of the HA unit with threoninamide was calculated from the integrated value of the peak derived from acetyl in HA glucosamine (—COCH₃, 2.0 ppm; 3H) and the integrated value of the peak derived from methyl in threoninamide (—CH₃, 1.2 ppm; 3H) using the same procedure as in Example 1-4-1 (Table 4).

Comparative Example 1-1-12

Synthesis of Derivatives of HA Modified with L-glutaminamide (Gln-NH₂) (HA-Gln-NH₂ and HA-Gln NH₂/Rh)

The same procedure as in Example 1-4-15 was performed except that L-glutaminamide hydrochloride (Kokusan Chemical Co., Ltd.) was used instead of L-alaninamide hydrochloride; thereby, HA-Gln-NH, was given as a white solid, or HA-Gln-NH₂/Rh as a red solid.

FIG. 5-12 shows the ¹H-NMR spectrum obtained by analyzing the product under the same conditions as described in Example 1-3. The modification degree of the HA unit with glutaminamide was calculated from the integrated value of the peak derived from acetyl in HA glucosamine (—COCH₃, 2.0 ppm; 3H) and the integrated value of the peak derived from methylene in glutaminamide (—CH₂CH₂CONH₂, 2.4 ppm; 2H) using the same procedure as in Example 1-4-1 (Table 4). Since the peak derived from acetyl in HA glucosamine overlapped with the peak for methylene in glutaminamide (—CH₂CONH₂, 2.1 ppm 2H), the integrated value of the peak at 2.4 ppm was subtracted from the integrated value of the peaks at 1.8 to 2.2 ppm, and the resulting value was taken as the peak derived from acetyl in HA glucosamine and used for modification degree calculation.

TABLE 4

Degrees of modification of synthesized HA derivatives (99 kDa)

| Com. Ex. No. | Modification compound | Modification degree with amino-carboxylic acid derivative (%) |
|---|---|---|
| 1-1-3 | Phe/FL | 88 |
| 1-1-4 | Tyr/FL | 97 |
| 1-1-5 | MePhe/FL | 80 |
| 1-1-6 | Pro-OMe/FL | 78 |
| 1-1-7 | Gly-NH₂ | 99 |
|  | Gly-NH₂/Rh | 93 |

TABLE 4-continued

Degrees of modification of synthesized HA derivatives (99 kDa)

| Com. Ex. No. | Modification compound | Modification degree with amino-carboxylic acid derivative (%) |
|---|---|---|
| 1-1-8 | Ser-NH₂ | 98 |
|  | Ser-NH₂/Rh | 93 |
| 1-1-9 | Leu-NH₂ | 98 |
|  | Leu-NH₂/Rh | 83 |
| 1-1-10 | Ile-NH₂ | 95 |
|  | Ile-NH₂/Rh | 83 |
| 1-1-11 | Thr-NH₂ | 97 |
|  | Thr-NH₂/Rh | 85 |
| 1-1-12 | Gln-NH₂ | 93 |
|  | Gln-NH₂/Rh | 81 |

Comparative Example 1-2

Synthesis of HA Derivatives from HA-TBA

Comparative Example 1-2-1

Synthesis of Derivatives of HA Modified with L-norleucine (Nle) (HA-Nle)

The same procedure as in Example 1-5-1 was performed except that L-norleucine methyl ester hydrochloride (Nle-OMe.HCl, Bachem) was used instead of AMCHCA-OMe.HCl; thereby, the products of interest (HA-Nle) were given as a white solid. The addition ratios of the reagents were shown in Table 5.

FIG. 6-1 shows the ¹H-NMR spectrum of a representative example of the products, which was obtained by analyzing in D₂O the product synthesized using HA-Na with a MW of 99 kDa in the presence of the reagents at the ratio of HA-TBA unit/DMT-MM/Cha-OMe.HCl=1/3/5. The modification degree of the HA unit with Me was calculated from the integrated value of the peak derived from acetyl in HA glucosamine (—COCH₃, 2.0 ppm; 3H) and the integrated value of the peak derived from methyl in Nle (—CH₃, 0.9 ppm; 3H) using the same procedure as in Example 1-4-1 (Table 5).

Comparative Example 1-2-2

Synthesis of a Derivative of HA Modified with L-tertiary leucine (tLeu) (HA-tLeu)

The same procedure as in Example 1-5-1 was performed except that L-tertiary leucine methyl ester hydrochloride (tLeu-OMe.HCl, Fluka) was used instead of AMCHCA-OMe.HCl; thereby, the products of interest (HA-tLeu) were given as a white solid. The addition ratios of the reagents were shown in Table 5.

FIG. 6-2 shows the ¹H-NMR spectrum of a representative example of the products, which was obtained by analyzing in D₂O the product synthesized using HA-Na with a MW of 99 kDa in the presence of the reagents at the ratio of HA-TBA unit/DMT-MM/Cha-OMe.HCl=1/3/5. The modification degree of the HA unit with tLeu was calculated from the integrated value of the peak derived from acetyl in HA glucosamine (—COCH₃, 2.0 ppm; 31-1) and the integrated value of the peak derived from three methyls in tLeu (—C(CH₃)₃, 1.0 ppm; 9H) using the same procedure as in Example 1-4-1 (Table 5).

Comparative Example 1-2-3

Synthesis of Derivatives of HA Modified with para-fluorophenylalanine (pF-Phe) (HA-pFPhe)

The same procedure as in Example 1-5-1 was performed except that para-fluorophenylalanine ethyl ester hydrochloride (pFPhe-OEt.HCl, Bachem) was used instead of AMCHCA-OMe.HCl and that carboxy deprotection was carried out using 5N NaOH pH 13.2; thereby, the products of interest (HA-pFPhe) were given as a white solid.

FIG. 6-3 shows the $^1$H-NMR spectrum of a representative example of the products, which was obtained by analyzing in $D_2O$ the product synthesized using HA-Na with a MW of 99 kDa in the presence of the reagents at the ratio of HA-TBA unit/DMT-MM/Phe-OEt.HCl 1/3/5. The modification degree of the HA unit with pFPhe was calculated from the integrated value of the peak derived from acetyl in HA glucosamine (—COCH$_3$, 2.0 ppm; 3H) and the integrated value of the peaks derived from the aromatic ring in pFPhe (—C$_6$H$_4$F, 7.1, 7.3 ppm; 4H) using the same procedure as in Example 1-4-1 (Table 5).

Comparative Example 1-2-4

Synthesis of Derivatives of HA Modified with (s)-(+)-2-phenylglycine (Phg) (HA-Phg)

The same procedure as in Example 1-5-1 was performed except that (s)-(+)-2-phenylglycine methyl ester hydrochloride (Phg-OMe.HCl, Sigma-Aldrich) was used instead of AMCHCA-OMe.HCl; thereby, the products of interest (HA-Phg) were given as a white solid.

FIG. 6-4 shows the $^1$H-NMR spectrum of a representative example of the products, which was obtained by analyzing in $D_2O$ the product synthesized using HA-Na with a MW of 99 kDa in the presence of the reagents at the ratio of HA-TBA unit/DMT-MM/Phg-OMe.HCl=1/3/5. The modification degree of the HA unit with Phg was calculated from the integrated value of the peak derived from acetyl in HA glucosamine (—COCH$_3$, 2.0 ppm; 3H) and the integrated value of the peaks derived from the aromatic ring in Phg (—C$_6$H$_5$, 7.3-7.5 ppm; 5H) using the same procedure as in Example 1-4-1 (Table 5).

TABLE 5

Amounts of the reagents used to synthesize HA derivatives, and synthesis results

| Com. Ex. No. | Modification compound | HA molecular weight | Molar addition ratio of modification compound and DMT-MM (HA-TBA unit/DMT-MM/ modification compound) | Modification degree (%) |
| --- | --- | --- | --- | --- |
| 1-2-1 | Nle | 99 kDa | 1/3/5 | 103 |
|  | Nle | 25 kDa | 1/3/5 | 100 |
| 1-2-2 | tLeu | 99 kDa | 1/3/5 | 105 |
|  | tLeu | 25 kDa | 1/3/5 | 107 |
| 1-2-3 | pFPhe | 99 kDa | 1/3/5 | 108 |
|  | pFPhe | 25 kDa | 1/3/5 | 109 |
| 1-2-4 | Phg | 99 kDa | 1/3/5 | 97 |
|  | Phg | 25 kDa | 1/3/5 | 103 |

Comparative Example 1-3

Synthesis of a FL-Labeled PEG Derivative (PEG-FL)

PEG (MEPA-30T NOF Corporation) was dissolved in ultrapure water to give a concentration of 10 mg/ml, and then the solution was diluted 2-fold with a 100 mM phosphate buffer solution (pH 7.4) to prepare a 5 mg/mL solution. NHS fluorescein (NHS-FL, PIERCE) was added as a DMSO solution to this solution in an amount of 15 molar equivalents relative to the terminal end of PEG, and stirring was performed at room temperature overnight. After the reaction solution was reprecipitated with diethyl ether, the precipitate was collected by filtration, and dissolved again in ultrapure water, the solution was dialyzed (Spectra/Por 4, molecular weight cutoff (MWCO): 12-14 kDa) against large excess ultrapure water, and the dialyzate was freeze-dried to give the product of interest (PEG-FL) as a yellow solid.

FIG. 7 shows the $^1$H-NMR spectrum obtained by analyzing the product under the same conditions as described in Example 1-3. The findings of the peak derived from the one terminal end of PEG (—OCH$_3$, 3.4 ppm, 3H) and the peaks derived from fluorescein (7-8 ppm) demonstrated the modification of the terminal end of PEG with FL.

Example 2

In Vitro Confirmation of Biodegradability

The resistances of the samples incubated under certain conditions to Hyaluronidase SD (Hyase, Seikagaku Corporation) were confirmed.

Some of the products obtained in Example 1-4 and Comparative Example 1-1 were determined. Five (5) or 20 mg/mL aqueous solutions of the products were used as the analysis samples, and a 5 mg/mL aqueous solution of HA-Na was used as a standard sample. The samples were diluted 10-fold with PBS or rat plasma. The PBS-diluted samples were each incubated at 37° C. for 0 hour, 24 hours, or 1 week, respectively, and the plasma-diluted samples were incubated at 37° C. for 24 hours. Each of the samples was divided into two aliquots. One aliquot was mixed at a ratio of sample/ultrapure water/ 0.2 M phosphate buffer solution (pH 6.2)/0.2 M phosphate buffer solution (pH 6.2) containing Hyase (0.5 U/mL)=2/1/ 2/1, and the resulting mixture was put to use as a Hyase-treated sample. The other aliquot was mixed at a ratio of sample/ultrapure water/0.2M phosphate buffer solution (pH 6.2)=2/1/3, and the resulting mixture was put to use as a non-Hyase-treated sample. After the respective samples were incubated at 37° C. overnight, the contents of reducing terminal N-acetylglucosamine in the samples were quantified by the Reissig method described below. The samples derived from the standard sample were diluted 1, 3, 10, 30, 100, and 300-fold, respectively, so as to ensure that the makeups of the solvents were not changed. Then, the respective resulting samples, put to use as calibration curve samples, were subjected to coloration by the same procedure.

The thus-obtained Hyase-treated samples, non-Hyase-treated samples, and calibration curve samples were each mixed at a ratio sample/0.8M borate buffer solution (pH 9.1)/1N KOH=25/5/2. The resulting mixtures were each heated in a boiling water bath for 3 minutes and then placed on ice immediately. Next, p-dimethylaminobenzaldehyde was dissolved in a (1:70) mixed solution of 10N HCl and acetic acid to provide a reagent (10 mg/mL). The foregoing samples were each mixed with the reagent at a ratio of 32:150, and the resulting mixtures were each incubated at 37'C for 20 minutes and then placed on ice immediately. After the temperatures of the samples were returned to room temperature, they were determined for the absorbance at 544 nm immediately. Using the values obtained by subtracting the absorbances of the non-Hyase-treated samples from those of the Hyase-treated samples, a calibration curve was constructed to calculate the concentrations of reducing terminal N-acetylglucosamine in the respective samples, whereby the degradation degrees were determined from the following equation (Table 6):

thus confirming no biodegradability, and these test results also showed no degradability with Hyase. On the other hand, all of the other HA derivatives showed degradability.

In particular, the samples of Examples 1-4-1 to 1-4-6, 1-4-8 to 1-4-11, 1-4-14 to 1-4-16, 1-4-18, and 1-4-19 which were treated with rat plasma for one day showed enhanced degradability as compared with those samples which were treated with PBS for one day; this made it conceivable that these derivatives were altered to the forms more sensitive to Hyase-mediated degradation by releasing modification compounds in a biological environment.

TABLE 6

Results of in vitro evaluation of the biodegradabilities of HA derivatives

| Example No./ Com. Ex. No. | Modification compound | Initial degradation degree (%) | Degradation degree after treatment with PBS for one day (%) | Degradation degree after treatment with PBS for 7 days (%) | Degradation degree after treatment with rat plasma for one day (%) |
|---|---|---|---|---|---|
| Ex. 1-4-1 | Ala/FL | 0.92 | 0.96 | 0.92 | 3.19 |
| Ex. 1-4-2 | Ser/FL | 0.63 | 0.61 | 0.54 | 2.17 |
| Ex. 1-4-3 | Glu/FL | 2.45 | 2.54 | 2.40 | 6.92 |
| Ex. 1-4-4 | Gly | 1.06 | 1.09 | 1.21 | 2.73 |
| Ex. 1-4-5 | Val | 0.27 | 0.23 | 0.26 | 0.61 |
| Ex. 1-4-6 | Leu | 3.43 | 2.81 | 3.24 | 6.01 |
| Ex. 1-4-7 | Ile | 0.42 | 0.34 | 0.59 | n.d. |
| Ex. 1-4-8 | Thr | 0.11 | 0.12 | 0.23 | 1.02 |
| Ex. 1-4-9 | Asp | 0.26 | 0.29 | 0.22 | 0.88 |
| Ex. 1-4-10 | cACHCA/FL | 0.54 | 0.36 | 0.19 | 1.11 |
| Ex. 1-4-11 | tACHCA-OEt/FL | 1.14 | 0.85 | 0.65 | 1.69 |
| Ex. 1-4-12 | Aib/FL | 3.57 | 3.56 | 3.18 | 3.03 |
| Ex. 1-4-13 | ACBuCA-OEt/FL | 0.30 | 0.19 | 0.44 | n.d. |
| Ex. 1-4-14 | Asn | 0.26 | 0.10 | n.d. | 0.90 |
| Ex. 1-4-15 | Ala-$NH_2$ | n.d. | 0.22 | n.d. | 2.07 |
| Ex. 1-4-16 | Val-$NH_2$ | n.d. | 0.88 | 0.72 | 2.28 |
| Ex. 1-4-17 | Asn-$NH_2$ | n.d. | n.d. | 0.23 | n.d. |
| Ex. 1-4-18 | Me | 0.31 | 0.33 | 0.32 | 0.68 |
| Ex. 1-4-19 | Pr | 0.19 | 0.09 | 0.10 | 0.46 |
| Com. Ex. 1-1-2 | EDOBEA-Ac/FL | n.d. | n.d. | n.d. | n.d. |
| Com. Ex. 1-1-3 | Phe/FL | 1.74 | 1.84 | 1.82 | 4.75 |
| Com. Ex. 1-1-4 | Tyr/FL | 0.23 | 0.13 | 0.19 | 0.98 |
| Com. Ex. 1-1-5 | MePhe/FL | 7.49 | 5.57 | 6.06 | 5.25 |
| Com. Ex. 1-1-6 | Pro-OMe/FL | 8.12 | 10.03 | 8.94 | 7.92 |
| Com. Ex. 1-1-7 | Gly-$NH_2$ | 1.04 | 0.11 | 0.30 | 1.58 |
| Com. Ex. 1-1-8 | Ser-$NH_2$ | n.d. | 0.91 | n.d. | 2.23 |
| Com. Ex. 1-1-9 | Leu-$NH_2$ | 0.50 | 0.92 | 0.79 | 2.17 |
| Com. Ex. 1-1-10 | Ile-$NH_2$ | n.d. | 0.93 | 0.34 | 3.53 |
| Com. Ex. 1-1-11 | Thr-$NH_2$ | 1.29 | n.d. | 0.24 | 1.52 |
| Com. Ex. 1-1-12 | Gln-$NH_2$ | n.d. | 0.17 | n.d. | 0.91 |

* "n.d. (not determined)" represents that the degradation degree could not be calculated because the concentration of reducing terminal N-acetylglucosamine was below the lower limit of quantitation.

$$(\text{Degradation degree}) = \frac{\left(\begin{array}{c}\text{Concentration of reducing}\\\text{terminal } N\text{-acetylglucosamine}\end{array}\right)}{\left(\begin{array}{c}\text{Concentration of disaccharide repeating}\\\text{units determined by } {}^1H\text{-}NMR\end{array}\right)} * 100 \quad [\text{Formula 27}]$$

Additionally, the standard sample HA-Na degraded completely (100%) under these conditions. At the degradation degree of 1%, it is estimated that HA with a MW of 100 kDa is cleaved at 2.5 positions per molecule, thereby resulting in a decrease in molecular weight down to 40 kDa.

As for HA-EDOBEA-Ac/FL (Comparative Example 1-1-2), size exclusion chromatography analysis was performed as described in Example 3-3-2, but no injected compound with reduced molecular weight was observed in the urine sample, Example 3

In Vivo Confirmation of Retentivity in Blood and Biodegradability

Example 3-1

Biological Samples from HA Derivative-Treated Rats

The compounds obtained in Example 1-4 and Comparative Example 1-1, and the compounds obtained in Comparative Example 1-3 were intravenously administered to rats at single doses of 20 and 10 mg/kg, respectively. Five (5) minutes, and 2, 7, 24, 48, 72, 168, 240 and 336 hours after treatment, blood samples were collected from jugular vein using syringes treated with sodium heparin and were subjected to centrifugation to obtain plasma. The plasma samples were cryopreserved below −20° C. until analysis. The urine samples were collected using metabolic cages from 0 to 24 hours, 24 to 48 hours, 48 to 72 hours, 72 to 96 hours, 168 to 192 hours, 240 to 264 hours, and 336 to 360 hours after treatment. The amounts of urine were measured, and a portion of the respective samples were cryopreserved below −20° C. until analysis.

Example 3-2

Analysis of the Plasma Samples from the HA Derivative-Treated Rats

Example 3-2-1

Preparation of Analysis Samples

The plasma samples were thawed, stirred, and centrifuged to collect the supernatants. The supernatants were diluted with a buffer solution (FL-labeled HAs: phosphate buffer solution (pH 8.0, I=0.15); Rh-labeled HAs: PBS). The administration solutions were diluted with a (3:1) mixed solution of a buffer solution and rat blank plasma to prepare calibration curve samples.

Example 3-2-2

Concentration Determination

The samples prepared in Example 3-2-1 were determined for their fluorescence intensity using a plate reader (SPECTRAmax GEMINI, Molecular Devices) (FL-labeled HAs: excitation wavelength 495 nm, fluorescence wavelength 520 nm; Rh-labeled HAs: excitation wavelength 552 nm, fluorescence wavelength 595 nm). A calibration curve for each compound was constructed from the measured values of the calibration curve samples, whereby the concentrations of compounds in plasma of the respective individuals at the respective time points were calculated. The averages of the plasma concentrations are shown in FIG. 8, and the charts for the time courses of said averages are shown in FIG. 9.

Example 3-2-3

Calculation of Pharmacokinetic Parameters

The pharmacokinetic parameters were calculated using WinNonlin Ver 4.0.1/Ver 6.1 (Pharsight). The average data for each group calculated in Example 3-2-2 was subjected to model-independent analysis to calculate a clearance (CL) (Table 7). As a results, in comparison with PEG having practical retentivity in blood, all of the HA derivatives of Examples 1-4-1 to 1-4-19 showed lower CL values, thereby demonstrating that they have practical retentivity in blood. Also, some of the HA derivatives of Comparative Examples showed higher CL values than PEG, thereby revealing that HA derivatives showing different retentivities in blood depending on the type of the modification compound can be synthesized.

TABLE 7

Evaluation of the clearances of HA derivatives and PEG from the blood

| Ex. No./<br>Com. Ex. No. | Compound | CL<br>(mL/hr/kg) |
| --- | --- | --- |
| Example 1-4-1 | HA-Ala/FL | 1.0 |
| Example 1-4-2 | HA-Ser/FL | 1.1 |

TABLE 7-continued

Evaluation of the clearances of HA derivatives and PEG from the blood

| Ex. No./<br>Com. Ex. No. | Compound | CL<br>(mL/hr/kg) |
| --- | --- | --- |
| Example 1-4-3 | HA-Glu/FL | 3.0 |
| Example 1-4-4 | HA-Gly/FL | 1.4 |
| Example 1-4-5 | HA-Val/FL | 1.2 |
| Example 1-4-6 | HA-Leu/FL | 1.3 |
| Example 1-4-7 | HA-Ile/FL | 1.3 |
| Example 1-4-8 | HA-Thr/FL | 1.0 |
| Example 1-4-9 | HA-Asp/FL | 2.8 |
| Example 1-4-10 | HA-cACHCA/FL | 1.1 |
| Ex. 1-4-11 | HA-tACHCA-OEt/FL | 1.3 |
| Ex. 1-4-12 | HA-Aib/FL | 1.1 |
| Example 1-4-13 | HA-AcBuCA-OEt/FL | 0.8 |
| Example 1-4-14 | HA-Asn/Rh | 1.8 |
| Example 1-4-15 | HA-Ala-NH$_2$/Rh | 2.0 |
| Example 1-4-16 | HA-Val-NH$_2$/Rh | 2.5 |
| Ex. 1-4-17 | HA-Asn-NH$_2$/Rh | 2.4 |
| Ex. 1-4-18 | HA-Me/FL | 1.1 |
| Ex. 1-4-19 | HA-Pr/FL | 0.9 |
| Com. Ex. 1-1-1 | HA-FL | 8.4 |
| Com. Ex. 1-1-2 | HA-EDOBEA-Ac/FL | 0.6 |
| Com. Ex. 1-1-3 | HA-Phe/FL | 6.0 |
| Com. Ex. 1-1-4 | HA-Tyr/FL | 14.8 |
| Com. Ex. 1-1-5 | HA-MePhe/FL | 12.9 |
| Com. Ex. 1-1-6 | HA-Pro-OMe/FL | 3.7 |
| Com. Ex. 1-1-7 | HA-Gly-NH$_2$/Rh | 6.6 |
| Com. Ex. 1-1-8 | HA-Ser-NH$_2$/Rh | 29.3 |
| Com. Ex. 1-1-9 | HA-Leu-NH$_2$/Rh | 3.6 |
| Com. Ex. 1-1-10 | HA-Ile-NH$_2$/Rh | 3.2 |
| Com. Ex. 1-1-11 | HA-Thr-NH$_2$/Rh | 47.9 |
| Com. Ex. 1-1-12 | HA-Gln-NHa/Rh | 10.6 |
| Com. Ex. 1-3 | PEG-FL | 3.0 |

Example 3-3

Analysis of the Urines from HA Derivative-Treated Rats

Example 3-3-1

Preparation of Analysis Samples

The urine samples were thawed, stirred, and passed through a 0.22 μm filter to collect the filtrates. The filtrates were diluted with a buffer solution (FL-labeled HAs: phosphate buffer solution (pH 6.5, I=0.15): Rh-labeled HAs: PBS). The administration solutions were diluted with a (1:1) mixed solution of a buffer solution and rat blank urine prepare standard samples.

Example 3-3-2

Size Exclusion Chromatography Analysis

The samples prepared in Example 3-3-1 were subjected to size exclusion chromatography to observe the changes in molecular weight distribution. The size exclusion chromatography analysis was made using the Alliance HPLC system (Nihon Waters K.K.). The analysis conditions are as follows.
  Size Exclusion Chromatography Analysis Conditions
  Analysis column: TSKgel G5000PWXL (Tosoh Corporation)
  Column temperature: 25° C.
  Mobile phase: Phosphate buffer solution (pH 6.5, I=0.15) (for FL-labeled HAs)
  PBS (for Rh-labeled HAs)
  Flow rate: 0.5 mL/min
  Detection: Ex 495 nm/Em 520 nm (FL-labeled HAs)
  Ex 552 nm/Em 595 nm (Rh-labeled HAs)

The results are shown in FIG. 10. For each figure, the left panel shows the chromatograms over the same range at the respective time points, and the right panel shows the chromatograms at the respective time points which were normalized by the strongest peak.

As for the HA derivative of Comparative Example 1-1-2, no injected compound with reduced molecular weight was observed in the urine samples. On the other hand, as for all of the HA derivatives of Examples, those injected compounds with reduced molecular weight were detected in the urine samples. This indicates that the HA derivatives of the present invention have biodegradability and are excreted from the body after treatment.

Example 4

Verification of Membrane Disruptive Property Using Liposome

Example 4-1

Preparation of a Liposome Encapsulating a Phosphor and a Quencher

First, 8-hydroxypyrene-1,3,6-trisulfonic acid trisodium salt (pyramine) (Sigma-Aldrich) was dissolved in distilled water at a concentration of 60 μmol/mL, and then p-xylene-bis-(N-pyridinium bromide) (DPX) (Sigma-Aldrich) was dissolved in distilled water at a concentration of 85.7 μmol/mL; thereafter, these solutions were mixed in equivalent amounts to prepare an aqueous pyramine/DPX solution.

The resulting pyramine/DPX solution (2 mL) was added to a COATSOME EL-11A vial (NOF Corporation) and the components were mixed, whereby a liposome solution was prepared.

Thereafter, in order to remove non-encapsulated pyramine and DPX, the solution was subjected to purification with PD-10 columns and purification by dialysis (Spectra/Por 4, molecular weight cutoff (MWCO): 12-14 kDa) against 500 mL of physiological saline three times, whereby a liposome solution was given.

The liposome solution was diluted 5-fold with a phosphate buffer solution an inonic strength of 0.15 and a pH of 6 or 7.4; thereby a liposome solution with each pH was prepared.

Example 4-2

Evaluation of Liposomal Membrane Disruptive Property

The HA derivatives obtained in Example 1-5 and Comparative Example 1-2 were each dissolved in physiological saline to give HA-Na concentration of 10 mg/mL, and the respective solutions were sequentially diluted with physiological saline to adjust the concentrations to 10, 5, 1, 0.5, 0.1, 0.05, and 0.01 mg/mL. As a positive control, a solution of TritonX in 10 mg/mL physiological saline was prepared. As a negative control, physiological saline was used. In addition, poly-L-lysine hydrobromide (PLL, MW 15-30 kDa, Wako Pure Chemical Industries, Ltd.) was selected as a positive control substance having a membrane disruptive property, and was dissolved in physiological saline to give a concentration of 10 mg/mL.

After 25 μL of the liposome solution was added to 200 μL of the phosphate buffer solution with pH 7.4 or pH 6.0, 25 μL of the samples were each added thereto. After incubation at 37° C. for 3 hours, the mixtures were each passed through a 0.22 μL filter, and 100 μL of the filtrates were determined for their fluorescence intensity using a plate reader (SPECTRAmax GEMINI) (excitation wavelength 450 nm, emission wavelength 510 PLL was determined only at pH 7.4.

The indicator for a membrane disruptive property was calculated as a liposome degradation degree according to the following equation.

$$\text{(Liposome degradation degree)} = \frac{\text{(Fluorescence intensity of } HA\text{-added sample)} - \text{(Flurorescence intensity of } saline\text{-added sample)}}{\text{(Flurorescence intensity of } TritonX\text{-added sample)} - \text{(Fluorescence intensity of } saline\text{-added sample)}} \times 100 \quad \text{[Formula 28]}$$

The results are shown in FIG. 11. The samples HA-Nle, HA-tLeu, and HA-pFPhe used as Comparative Examples showed no membrane disruptive property at either pH, whereas the samples used in Examples showed a higher membrane disruptive property at pH 6.0 than pH 7.4. In particular, HA-pcACHCA, HA-Nal, HA-APBA, HA-Cha, HA-AMBA, HA-3AMBA, HA-APhPA, HA-AEB, HA-AMClBA, HA-AMSA, HA-4AMCHCA, HA-Chg and HA-pHPhg did not show any membrane disruptive property at pH 7.4 but showed it only at pH 6.0. Moreover, since PLL showed a liposome degradation degree of 6.6% at pH 7.4, it can be judged that any derivative adequately functions as a substance having a membrane disruptive property if it shows a liposome degradation degree of at least a few percent, and it was thus demonstrated that the HA derivatives of the present invention have a membrane disruptive property at pH 6.0.

Example 5

Synthesis of HA-Ala Derivative/PTH Analogue Conjugates

Example 5-1

Synthesis of a TBA Salt of HA-Ala (HA-Ala-TBA)

An anhydrous DMSO solution (5 mg/mL) of HA-TBA synthesized using HA-Na (99 kDa) as a starting material in Example 1-2 was prepared. Then, L-alanine ethyl ester hydrochloride was added in an amount of 3 molar equivalents relative to the HA unit. Next, DMT-MM was added in an amount of 3 molar equivalents relative to the HA unit, and stirring was performed at room temperature overnight. The reaction solution was dialyzed (Spectra/Por 4, molecular weight cutoff (MWCO): 12-14 kDa) against an aqueous solution of 0.3 M NaCl and distilled water in this order. 5N NaOH solution was added to the resulting dialyzate to adjust the pH to at least 12.5, and stirring was performed for an hour to perform carboxy deprotection via ethyl ester hydrolysis. Thereafter, the mixture was neutralized with 5N HCl solution and further dialyzed against distilled water and ultrapure water in this order. The suspension of the cation exchange resin converted to a TBA salt in Example 1-1 was added to the resulting dialyzate in an amount of 5 molar equivalents relative to the HA unit as calculated for the ion exchange capacity of the resin. After stirring for 15 minutes, the mixture was passed through a 0.45 μm filter, and the filtrate was freeze-dried to give HA-Ala-TBA as a while solid. A portion of the product was taken and dialyzed against an aqueous solution of 0.3 M NaCl and distilled water in this order, and the dialyzate was freeze-dried for use as a sample for calculating the modification degree with alanine.

FIG. 12-1 shows the $^1$H-NMR spectra obtained by analyzing the sample for calculating the modification degree with alanine, and the product under the same conditions as described in Example 1-3. The modification degree of the HA unit with alanine was calculated to be 98% by the same procedure as in Example 1-4-1. The content of HA units per weight in HA-Ala-TBA was quantified by the same procedure as in Example 1-3.

Example 5-2

Synthesis of HA-Ala-EDOBEA

EDOBEA and BOP were added in this order to the anhydrous DMSO solution (5 mg/mL) of HA-Ala-TBA synthesized in Example 5-1 in amounts of 50 and 0.15 molar equivalents, respectively, relative to the HA unit, and stirring was performed at room temperature for 6 hours. The reaction solution was dialyzed (Spectra/Por 4, molecular weight cut-off (MWCO): 12-14 kDa) for purification against an aqueous solution of 0.3 M NaCl, and distilled water in this order, and the dialyzate was freeze-dried to give HA-Ala-EDOBEA as a white solid.

The product was subjected to $^1$H-NMR analysis by the same procedure as described in Comparative Example 1-1-2 and, as a result, the modification degree with EDOBEA was found to be 9.4%. The content of HA units was quantified by the same procedure as in Example 1-3. FIG. 12-2 shows the $^1$H-NMR spectrum of the product.

Example 5-3

Synthesis of HA-Ala-EDOBEA-Rh

The aqueous solution (10 mg/mL) of HA-Ala-EDOBEA synthesized in Example 5-2 was diluted 2-fold with a 100 mM phosphate buffer solution (pH 7.4), NHS-rhodamine was added as a 5 mg/mL DMSO solution in an amount of 0.07 molar equivalents relative to HA unit, and stirring was performed at room temperature for 2 hours. The reaction solution was purified on a desalting column (PD-10, GE Healthcare) equilibrated with ultrapure water, and the HA fraction was freeze-dried to give HA-Ala-EDOBEA-Rh as a red solid.

FIG. 12-3 shows the $^1$H-NMR spectrum obtained by analyzing the product in $D_2O$. The content of HA units per weight was quantified by the same procedure as in Example 1-3. Also, the product was dissolved in a 100 mM carbonate buffer solution (pH 9.0) at a concentration of 0.042 mg/mL, and the Rh content per weight was quantified from the absorbance at 552 nm, whereby the modification degree of the HA unit with Rh was calculated to be 3.1%. Furthermore, the molar absorption coefficient of the resulting product was calculated to be 2,690 $M^{-1}$ $cm^{-1}$.

Example 5-4

Synthesis of a Bromoacetyl Derivative of HA (HA-Ala-EDOBEA-BA/Rh/Ac)

The aqueous solution (20 mg/mL) of HA-Ala-EDOBEA-Rh synthesized in Example 5-3 was used as a starting material. The solution was diluted 2-fold with a 100 mM phosphate buffer solution (pH 7.4), NHS-bromoacetate (NHS-BA, Sigma-Aldrich) was added as a 50 mg/mL acetonitrile solution in an amount of 0.5 molar equivalents relative to the HA unit, and stirring was performed at room temperature for 2 hours. Thereafter, acetic anhydride was added in an amount of 20 molar equivalents relative to the HA unit and further stirring was performed for an hour to acetylate terminal amino in excess EDOBEA. The reaction solution was purified on a desalting column (PD-10) equilibrated with ultrapure water, and the fractionated HA fraction was concentrated about 2-fold by centrifugal ultrafiltration (Macrosep, MWCO 3000, Paul Life Science) to give HA-Ala-EDOBEA-BA/16/Ac as an aqueous solution. The aqueous solution was cryopreserved at −20° C. until later use. After being freeze-dried, an aliquot was measured for its weight to calculate the concentration of solids in the solution.

Example 5-5

Synthesis of a HA-Ala/PTH Analogue Conjugate (HA-Ala-PTH/Rh)

The aqueous solution of HA-Ala-EDOBEA-BA/Rh/Ac synthesized in Example 5-4 was used as a starting material. PTH-Cys (SVSEIQLMHNLGKHLNSMERVEWL-RKKLQDVHNFC, American Peptide Company) which was obtained by introducing cysteine to the C terminus of human PTH(1-34) was used as a PTH analogue. A 3/10 volume of acetonitrile and a 1/10 volume of a 1M phosphate buffer solution (pH 7.4) were added to the HA-Ala-EDOBEA-BA/Rh/Ac solution. After PTH-Cys was dissolved in a 10 mM citrate buffer solution (pH 4.5) at a concentration of 5 mg/mL, the resulting solution was added to the HA-Ala-EDOBEA-BA/Rh/Ac solution in an amount of 0.03 molar equivalents relative to the HA unit, and the mixture was incubated at 37° C. overnight. Cysteine hydrochloride monohydrate (Wako Pure Chemical Industries, Ltd.) was added as a 20 mg/mL, aqueous solution in an amount of 1 molar equivalent relative to the HA unit, and the mixture was further incubated at 37° C. for 3 hours, and then the pH of the mixture was adjusted to 4.5 with an aqueous solution of 1N sodium hydroxide. The content of HA units per weight was specified to be 1.5 μmol/mg, and this value was used for calculating the HA unit.

Next, the reaction solution was purified through centrifugal ultrafiltration (Macrosep, MWCO10000) by repeating dilution with a 2 mM citrate buffer solution (pH 4.5) and concentration four times to prepare a HA-Ala-PTH/Rh concentrate. The resulting concentrate was diluted 100-fold with a 100 mM carbonate buffer solution (pH 9.0), and the dilution was determined for its absorbance at 552 nm, whereby the HA concentration was calculated to be 24.3 μmol/mL using the absorption coefficient of HA-Ala-EDOBEA-Rh calculated in Example 5-3. Amino acid analysis was made by the AccQ•Tag method (Waters), whereby the PTH concentration was calculated to be 141.75 nmol/mL and the modification degree with PTH was determined to be 0.58%. In the amino acid analysis, hydrolysis and derivatization were conducted using the Pico•Tag workstation and the AccQ•Tag chemistry package pursuant to the manual accompanying the package. HPLC analysis was made using the Waters 2690 Separation Module and the Waters 474 Fluorescence Detector, and the analysis for calculating the amino acid concentration was based on the concentration of lysine residues.

Example 6

In Vivo Confirmation of Retentivity in Blood and Biodegradability of the HA-Ala Derivative/PTH Analogue Conjugate

Example 6-1

Biological Samples from HA Derivative-Treated Rats

The compound obtained in Example 5-5 was intravenously administered to rats at a single dose of 10 mg/kg, 5 minutes, and 2, 7, 24, 48, 72, 168, 240 and 312 hours after treatment, blood samples were collected from jugular vein using syringes treated with sodium heparin and were subjected to centrifugation to obtain plasmas. The plasma samples were cryopreserved below −20° C. until analysis. The urine samples were collected using metabolic cages from 0 to 24 hours, 24 to 48 hours, 48 to 72 hours, to 96 hours, 144-168 hours, 216-240 hours, and 288-312 hours after treatment. The amounts of urine were measured, and a portion of the respective samples were cryopreserved below −20° C. until analysis.

Example 6-2

Analysis of the Plasma Samples from the HA Derivative-Treated Rats

Example 6-2-1

Preparation of Analysis Samples

Analysis samples were prepared by the procedure described in Example 3-2-1,

Example 6-2-2

Concentration Determination

Using the samples prepared in Example 6-2-1, the concentrations of the compound in plasma of the respective individuals at the respective time points were calculated by the procedure described in Example 3-2-2. The averages of the plasma concentrations are shown in FIG. 13, and the charts for the time courses of said averages are shown in FIG. 14.

Example 6-2-3

Calculation of Pharmacokinetic Parameters

Using the average data calculated in Example 6-2-2, the clearance (CL) was calculated to be 1.0 by the procedure described in Example 3-2-3. The biodegradable hyaluronic acid derivative showed practical retentivity in blood also in the form of the conjugate with the drug.

Example 6-3

Analysis of the Urines Samples from the HA Derivative-Treated Rats

Example 6-3-1

Preparation of Analysis Samples

Analysis samples were prepared by the procedure described in Example 3-3-1.

Example 6-3-2

Size Exclusion Chromatography Analysis

FIG. 15 shows the results of the analysis of the samples prepared in Example 6-3-1 by the procedure described in Example 3-3-2. In this figure, the left panel shows the chromatograms over the same range at the respective time points, and the right panel shows the chromatograms at the respective time points which were normalized by the strongest peak.

A compound with reduced molecular weight was detected in the urine samples from the individuals treated with the compound of Example 5-5. This indicates that the conjugate between the biodegradable hyaluronic acid derivative and the drug maintains its biodegradability and is excreted from the body after treatment.

The invention claimed is:

1. A hyaluronic acid derivative comprising disaccharide units represented by Formula (I):

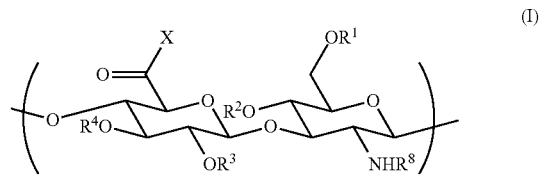

wherein
R$^1$, R$^2$, R$^3$, and R$^4$ are each independently selected from a hydrogen atom, C$_{1-6}$ alkyl, formyl and C$_{1-6}$ alkylcarbonyl;
R$^8$ is a hydrogen atom, formyl or C$_{1-6}$ alkylcarbonyl;
X is a group represented by —NHCH$_3$, —NH(CH$_2$)$_2$CH$_3$, —NR$^x$-A-B—COOR$^y$ or —NR$^x$—CHR$^c$—CONR$^{ya}$R$^{yb}$;
R$^x$ and R$^y$ are each independently selected from a hydrogen atom and C$_{1-6}$ alkyl;
A is selected from —CR$^a$R$^b$—, C$_{3-8}$ cycloalkylene, 2-cyclohexylethane-1,1-diyl, 2-(2-naphthyl)ethane-1,1-diyl, 3-phenylpropane-1,1-diyl, cyclohexylmethane-1,1-diyl, and 4-hydroxyphenylmethane-1,1-diyl, and B is a direct bond; or
A is —CH$_2$— or —CH$_2$—CH$_2$—, and B is selected from phenylene (wherein the phenylene may be substituted by one or more groups selected from hydroxy and halogen atoms), C$_{3-8}$ cycloalkylene and phenylmethane-1,1-diyl;
R$^a$ is selected from a hydrogen atom and C$_{1-6}$ alkyl;
R$^b$ is selected from a hydrogen atom and C$_{1-6}$ alkyl (wherein the C$_{1-6}$ alkyl may be substituted by one or more groups selected from hydroxy, carboxy and carbamoyl);
R$^c$ represents C$_{1-3}$-alkyl which may be substituted by carbamoyl;
R$^{ya}$ and R$^{yb}$ are each independently selected from a hydrogen atom, C$_{1-6}$ alkyl, formyl and C$_{1-6}$ alkylcarbonyl,
wherein, when X in Formula (I) is —NHCH$_3$, —NH(CH$_2$)$_2$CH$_3$, or —NR$^x$—CHR$^c$—CONR$^{ya}$R$^{yb}$, or when A in Formula (I) is —CR$^a$R$^b$— or C$_{3-8}$ cycloalkylene, the proportion of the disaccharide units of Formula (I) with respect to disaccharide units present is at least 70%.

2. The hyaluronic acid derivative according to claim 1, wherein X is —NHCH$_3$, —NH(CH$_2$)$_2$CH$_3$ or —NR$^x$—CHR$^c$—CONR$^{ya}$R$^{yb}$, or A is —CR$^a$R$^b$— or C$_{3-8}$ cycloalkylene.

3. The hyaluronic acid derivative according to claim 1, wherein

A is $C_{3-8}$ cycloalkylene, and B is a direct bond;

A is —$CH_2$— or —$CH_2$—$CH_2$—, and B is selected from phenylene (wherein the phenylene may be substituted by one or more groups selected from hydroxy and halogen atoms), $C_{3-8}$ cycloalkylene and phenylmethane-1,1-diyl; or A is selected from 2-cyclohexylethane-1,1-diyl, 2-(2-naphthyl)ethane-1,1-diyl, 3-phenylpropane-1,1-diyl, cyclohexylmethane-1,1-diyl and 4-hydroxyphenyl-methane-1,1-diyl, and B is a direct bond.

4. The hyaluronic acid derivative according to claim 1, wherein

A is —$CH_2$—, and B is selected from cyclohexane-1,1-diyl, benzene-1,4-diyl, benzene-1,3-diyl, 2-chlorobenzene-1,4-diyl and phenylmethane-1,1-diyl;

A is —$CH_2CH_2$—, and B is benzene-1,4-diyl; or

A is selected from 2-cyclohexylethane-1,1-diyl, 2-(2-naphthyl)ethane-1,1-diyl, and 3-phenylpropane-1,1-diyl; and B is a direct bond.

5. The hyaluronic acid derivative according to claim 1, further comprising disaccharide units represented by Formula (II):

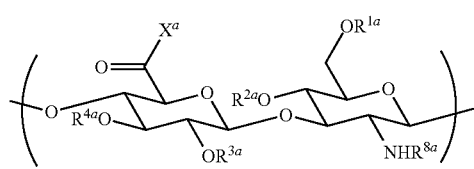

(II)

wherein $R^{1a}$, $R^{2a}$, $R^{3a}$, and $R^{4a}$ are each independently selected from a hydrogen atom, $C_{1-6}$ alkyl, formyl and $C_{1-6}$ alkylcarbonyl;

$R^{8a}$ is a hydrogen atom, formyl or $C_{1-6}$ alkylcarbonyl;

$X^a$ is selected from hydroxy and —O⁻Q⁺ wherein Q⁺ represents a countercation.

6. The hyaluronic acid derivative according to claim 1, further comprising disaccharide units represented by Formula (III):

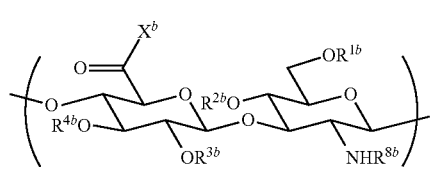

(III)

wherein $R^{1b}$, $R^{2b}$, $R^{3b}$, and $R^{4b}$ are each independently selected from a hydrogen atom, $C_{1-6}$ alkyl, formyl and $C_{1-6}$ alkylcarbonyl;

$R^{8b}$ is a hydrogen atom, formyl or $C_{1-6}$ alkylcarbonyl;

$X^b$ is a group represented by —$NR^e$—$Y^b$—$R^d$; wherein $R^e$ is a hydrogen atom or $C_{1-6}$ alkyl;

$R^d$ is a hydrogen atom, $C_{1-6}$ alkyl, —CO—C($R^7$)=$CH_2$, or —CO-$G^4$-$X^e$;

$R^7$ is a hydrogen atom or methyl;

$G^4$ is selected from phenylene, $C_{3-8}$ cycloalkylene, and -$G^5$-($C_{1-10}$ alkylene)-$G^6$-, wherein the $C_{1-10}$ alkylene moiety may have one to three phenylenes or $C_{3-8}$ cycloalkylenes inserted therein;

$G^5$ and $G^6$ are each independently selected from a direct bond, phenylene, or $C_{3-8}$ cycloalkylene;

$X^c$ is mercapto, a halogen atom or a group represented by the formula:

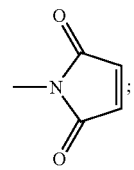

$Y^b$ is —$CH_2$—$(CHR^5)_{l-2}$—$CH_2$—NH—, —$CH_2$—$(CHR^6)_{p-2}$—$CH_2$—O~, —$(CH_2)_j$—S—, or —$(CH_2)_a$—$(Y^1$—$(CH_2)_b)_c$-G-;

l, p, and j are each independently an integer selected from 2 to 10, $R^5$ and $R^6$ are each independently a hydrogen atom or hydroxy;

a is an integer selected from 2 to 10;

each b is independently an integer selected from 2 to 10;

c is an integer selected from 1 to 200;

$Y^1$ is an oxygen atom or —$NR^n$—;

G is an oxygen atom, a sulfur atom or —NH—;

$R^n$ is a hydrogen atom, $C_{1-6}$ alkyl, —CO—$(CH_2)_d$—$R^o$, —$(CH_2)_e$—$R^p$ or —$(CH_2)_f$—$(Y^2$—$(CH_2)_g)_h$—$R^q$;

each g is independently an integer selected from 2 to 10;

d, e, f and h are each independently an integer selected from 2 to 10;

$R^o$, $R^p$ and $R^q$ are each independently a hydrogen atom, hydroxy, carboxy or —$NHR^r$;

$Y^2$ is an oxygen atom or —NH—;

$R^r$ is a hydrogen atom, formyl or $C_{1-6}$ alkylcarbonyl.

7. The hyaluronic acid derivative according to claim 1, which is prepared using hyaluronic acid composed exclusively of the disaccharide units each represented by Formula (II):

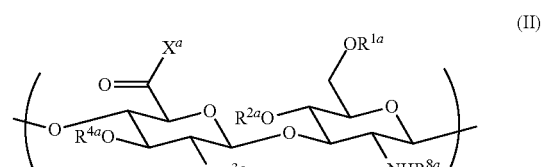

(II)

wherein, when $R^{1a}$, $R^{2a}$, $R^{3a}$, and $R^{4a}$ are all hydrogen atoms, $R^{8a}$ is acetyl, and $X^a$ is —O⁻Na⁺, the weight-average molecular weight is in the range of 20-120 kilodaltons.

8. The hyaluronic acid derivative according to claim 1, wherein an underivatized hyaluronic acid corresponding to the hyaluronic acid derivative in terms of backbone structure has a weight-average molecular weight of 20-120 kilodaltons, wherein the underivatized hyaluronic acid is hyaluronic acid composed exclusively of disaccharide units of Formula (II):

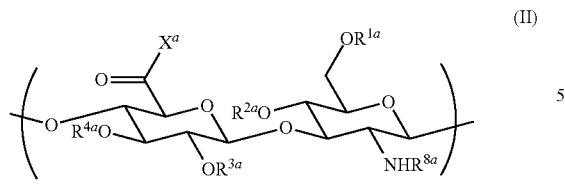 (II)

wherein $R^{1a}$, $R^{2a}$, $R^{3a}$, and $R^{4a}$ are hydrogen atoms, $R^{8a}$ is acetyl, and $X^a$ is —O$^-$Na$^+$.

9. A pharmaceutical composition comprising the hyaluronic acid derivative according to claim 1, as a carrier.

10. A hyaluronic acid derivative/drug conjugate wherein one or more drugs are conjugated to the hyaluronic acid derivative according to claim 1.

11. A biodegradable drug carrier comprising the hyaluronic acid derivative according to claim 1.

* * * * *